United States Patent
Zhang et al.

(10) Patent No.: US 10,934,531 B2
(45) Date of Patent: Mar. 2, 2021

(54) METHOD FOR ENANTIOSELECTIVE CARBENE C—H INSERTION USING AN IRON-CONTAINING PROTEIN CATALYST

(71) Applicant: California Institute of Technology, Pasadena, CA (US)

(72) Inventors: Ruijie Zhang, Los Angeles, CA (US); Lena Wohlschlager, Vienna (AT); Hans H. Renata, Jupiter, FL (US); Frances H. Arnold, La Canada, CA (US); Kai Chen, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 16/256,935

(22) Filed: Jan. 24, 2019

(65) Prior Publication Data
US 2019/0276805 A1 Sep. 12, 2019

Related U.S. Application Data

(60) Provisional application No. 62/621,749, filed on Jan. 25, 2018, provisional application No. 62/693,547, filed on Jul. 3, 2018, provisional application No. 62/734,059, filed on Sep. 20, 2018.

(51) Int. Cl.
| | |
|---|---|
| *C12N 9/00* | (2006.01) |
| *C12P 7/00* | (2006.01) |
| *C12P 9/00* | (2006.01) |
| *C12P 5/00* | (2006.01) |
| *C12P 13/00* | (2006.01) |
| *C12P 17/04* | (2006.01) |
| *C12P 13/02* | (2006.01) |
| *C12P 7/62* | (2006.01) |
| *C12P 17/06* | (2006.01) |
| *C12P 7/26* | (2006.01) |
| *B01J 31/00* | (2006.01) |
| *C12N 9/02* | (2006.01) |
| *C12P 17/12* | (2006.01) |
| *C12P 17/10* | (2006.01) |

(52) U.S. Cl.
CPC .......... *C12N 9/0042* (2013.01); *B01J 31/003* (2013.01); *C12N 9/0071* (2013.01); *C12P 5/005* (2013.01); *C12P 7/00* (2013.01); *C12P 7/26* (2013.01); *C12P 7/62* (2013.01); *C12P 7/625* (2013.01); *C12P 9/00* (2013.01); *C12P 13/00* (2013.01); *C12P 13/001* (2013.01); *C12P 13/02* (2013.01); *C12P 17/04* (2013.01); *C12P 17/06* (2013.01); *C12P 17/10* (2013.01); *C12P 17/12* (2013.01); *C12Y 106/02004* (2013.01); *C12Y 114/12017* (2013.01); *B01J 2231/46* (2013.01); *B01J 2531/842* (2013.01)

(58) Field of Classification Search
None
See application file for complete search history.

(56) References Cited

U.S. PATENT DOCUMENTS

| | | |
|---|---|---|
| 2016/0032330 A1 | 2/2016 | Renata et al. |
| 2017/0218346 A1 | 8/2017 | Kan et al. |

FOREIGN PATENT DOCUMENTS

| | | |
|---|---|---|
| WO | 2014/058729 A1 | 4/2014 |
| WO | 2014/058744 A2 | 4/2014 |
| WO | 2016/191612 A3 | 12/2016 |
| WO | 2017/066562 A2 | 4/2017 |

OTHER PUBLICATIONS

Zhang et al., "Supplementary Information—Enzymatic assembly of carbon-carbon bonds via iron-catalysed sp3 C—H functionalization", pp. 1-160. Nature, 2019, 565:67-72. Retreived from < https://www.nature.com/articles/s41586-018-0808-5#Sec3 > on Jul. 7, 2020.*
PCT/US2019/015027, "International Search Report and Written Opinion," dated May 14, 2019, 7 pages.
Bornscheuer et al., "Engineering the third wave of biocatalysis," *Nature,* 2012, vol. 485, pp. 185-194.
Brandenberg, et al., "Exploiting and engineering hemoproteins for abiological carbene and nitrene transfer reactions," *Curr Opin Biotechnol,* 2017, vol. 47, pp. 102-111.
Brandenberg, et al., "Stereoselective enzymatic synthesis of heteroatom-substituted cyclopropanes," *ACS Catal,* 2018, vol. 8, pp. 2629-2634.
Coelho, et al. "Olefin cyclopropanation via carbene transfer catalyzed by engineered cytochrome P450 enzymes." Science 339, 307-310 (2013).
Coelho, et al. "A serine-substituted P450 catalyzes highly efficient carbene transfer to olefins in vivo." Nat. Chem. Biol. 9, 485-487 (2013).
Dydio, et al., "An artificial metalloenzyme with the kinetics of native enzymes," *Science,* 2016, vol. 354, pp. 102-106.
Farwell, et al. "Enantioselective enzyme-catalyzed aziridination enabled by active-site evolution of a cytochrome P450," *ACS Cent Sci,* 2015, vol. 1, pp. 89-93.
Gilbert et al., "Synthesis of diverse 11- and 12-membered macrolactones from a common linear substrate using a single biocatalyst," *ACS Cent Sci,* 2017, vol. 3, pp. 1304-1310.

(Continued)

*Primary Examiner* — Suzanne M Noakes
(74) *Attorney, Agent, or Firm* — Kilpatrick Townsend & Stockton LLP

(57) ABSTRACT

Methods for catalyzing C—H insertion reactions using heme enzymes are described. The present disclosure provides a method for producing a C—H insertion product comprising providing an substrate having an sp$^3$-hybridized C—H bond, a carbene precursor such as a diazo reagent, and a heme enzyme, and admixing the components in a reaction for a time sufficient to produce the C—H insertion product. Heme enzyme variants useful for carrying out in vivo and in vitro C—H insertion reactions, as well as expression vectors and host cells expressing the heme enzymes, are also described.

16 Claims, 11 Drawing Sheets

Specification includes a Sequence Listing.

(56) References Cited

OTHER PUBLICATIONS

Griffin et al., "Catalytic C(sp3)-H Alkylation via an Iron Carbene Intermediate," *J Am Chem Soc*, Oct. 4, 2017, vol. 139, pp. 13624-13627.

Hernandez, et al. "Highly stereoselective biocatalytic synthesis of key Cyclopropane Intermediate to Ticagrelor," *ACS Catal*, 2016, vol. 6, pp. 7810-7813.

Hyster, et al., "Enzyme-controlled nitrogen-atom transfer enables regiodivergent C—H amination," *J Am. Chem Soc*, 2014, vol. 136, pp. 15505-15508.

Key, et al. "Abiological catalysis by artificial haem proteins containing noble metals in place of iron," *Nature*, 2016, vol. 534, pp. 534-537.

Knight, et al. "Diverse engineered heme proteins enable stereodivergent cyclopropanation of unactivated alkenes" *ACS Cent Sci*, 2018, vol. 4, pp. 372-377.

Liao, et al. "Site-selective and stereoselective functionalization of non-activate, tertiary C—H bonds." *Nature*, 2017, vol. 551, pp. 609-613.

Liao, et al. "Site-Selective Carbene-Induced C—H Functionalization Catalyzed by Dirhodium Tetrakis(triarylcyclopropanecarboxylate) Complexes." *ACS Catal*, Dec. 17, 2017, vol. 8, pp. 678-682.

Liao, et al. "Site-selective and stereoselective functionalization of unactivated C—H bonds," *Nature*, 2016, vol. 533, pp. 230-264.

Loskot et al., "Enantioselective total synthesis of nigelladine A via late-stage C—H oxidation enabled by an engineered P450 enzyme," *J Am Chem Soc*, 2017, vol. 139, pp. 10196-10199.

Mbuvi et al., "Catalytic C—H Insertions Using Iron(III) Porphyrin Complexes," *Organometallics*, Feb. 1, 2008, vol. 27, pp. 637-645.

Narayan, et al., "Enzymatic hydroxylation of an unactivated methylene C—H bond guided by molecular dynamics simulationsm," *Nat Chem*, 2015, vol. 7, pp. 653-660.

Onderko, et al., "Characterization of a selenocysteine-ligated P450 compound I reveals direct link between electron donation and reactivity," *Nat Chem*, 2017, vol. 9, pp. 623-628.

Prier et al., "Enantioselective, Intermolecular Benzylic C—H Amination Catalysed by an Engineered Iron-Haem Enzyme," *Nature Chemistry*, May 29, 2017, vol. 9, pp. 629-634.

Ren, et al., "Drug oxidation by cytochrome $P450_{BM3}$: Metabolite synthesis and discovering new P450 reaction types," *Chem Eur J*, 2015, vol. 21, pp. 15039-15047.

Ren, et al., "Synthesis of imidazolidin-4-ones via a cytochrome P450-catalyzed intramolecular C—H amination," *ACS Catal*, 2016, vol. 6, pp. 6833-6837.

Renata, et al. "Identification of mechanism-based inactivation in P450-catalyzed cyclopropanation facilitates engineering of improved enzymes." *J. Am. Chem. Soc.* 138, 12527-12533 (2016).

Sreenilayam, et al., "Metal substitution modulates the reactivity and extends the reaction scope of myoglobin carbene transfer catalysts," *Adv Synth Catal*, 2017, vol. 359, pp. 2076-2089.

Vargas, et al., "Myoglobin-catalyzed C—H functionalization of unprotected indoles," *Angew Chem Int Ed*, Jun. 15, 2018, vol. 57, pp. 9911-9915.

Yamaguchi, et al., "C—H bond functionalization: Emerging synthetic tools for natural products and pharmaceuticals," *Angew Chem Int Ed*, 2012, vol. 51, pp. 8960-9009.

Yang, et al., "Evolving artificial metalloenzymes via random mutagenesis," *Nat Chem* 2018, vol. 10, pp. 318-324.

Zhang et al., "Enzymatic Assembly of Carbon-Carbon Bonds via Iron-Catalysed Sp3 C—H Functionalization," *Nature*, Dec. 19, 2018, vol. 565, pp. 67-72.

* cited by examiner

FIG. 3A
FIG. 3B
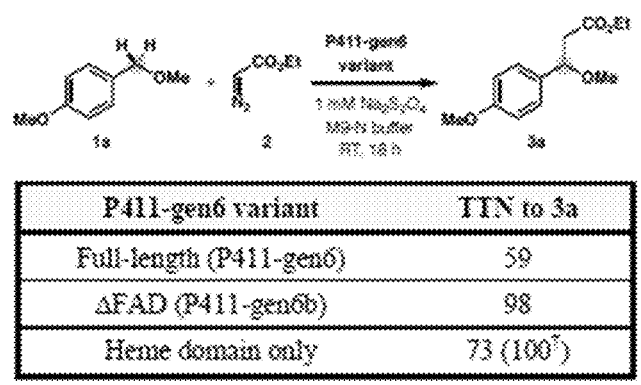
FIG. 4
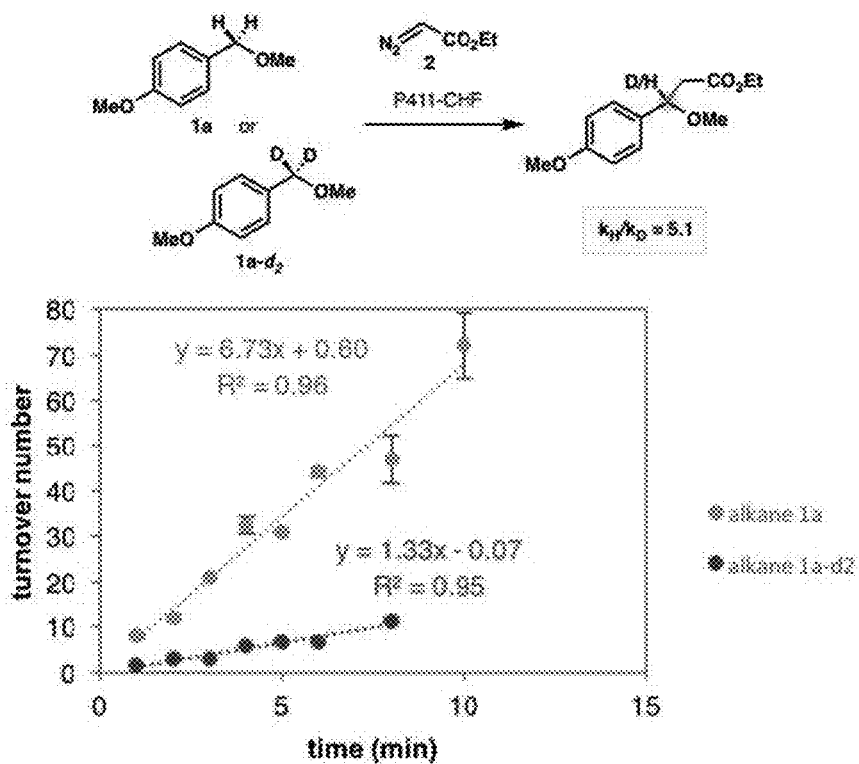

SEQUENCE LISTING

<160> NUMBER OF SEQ ID NOS: 18

<210> SEQ ID NO 1
<211> LENGTH: 664
<212> TYPE: PRT
<213> ORGANISM: Bacillus megaterium

<400> SEQUENCE: 1

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Val Arg Asp
65                  70                  75                  80

Phe Ala Gly Asp Gly Leu Phe Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Pro Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

```
Ile Lys Val Met Asn Asp Leu Val Asp Lys Ile Ile Ala Asp Arg Lys
210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
                260                 265                 270

Leu Ser Phe Ala Leu Tyr Phe Leu Val Lys Asn Pro His Val Leu Gln
            275                 280                 285

Lys Ala Ala Glu Glu Ala Ala Arg Val Leu Val Asp Pro Val Pro Ser
290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
                340                 345                 350

Leu Met Val Leu Ile Pro Gln Leu His Arg Asp Lys Thr Ile Trp Gly
            355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
                420                 425                 430

Ile Lys Glu Thr Leu Thr Leu Lys Pro Glu Gly Phe Val Val Lys Ala
            435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
                500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
                580                 585                 590

Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
610                 615                 620
```

```
Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr
                660
```

```
<210> SEQ ID NO 2
<211> LENGTH: 1048
<212> TYPE: PRT
<213> ORGANISM: Bacillus megaterium

<400> SEQUENCE: 2

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Arg Val
            35                  40                  45

Thr Arg Tyr Leu Ser Ser Gln Arg Leu Ile Lys Glu Ala Cys Asp Glu
50                  55                  60

Ser Arg Phe Asp Lys Asn Leu Ser Gln Ala Leu Lys Phe Val Arg Asp
65                  70                  75                  80

Phe Ala Gly Asp Gly Leu Phe Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Pro Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ala Asp Arg Lys
    210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Ala Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335
```

```
Glu Asp Thr Val Leu Gly Gly Glu Tyr Pro Leu Glu Lys Gly Asp Glu
                340                 345                 350

Leu Met Val Leu Ile Pro Gln Leu His Arg Asp Lys Thr Ile Trp Gly
            355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Glu
    450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
        675                 680                 685

Pro Lys Glu Ala Ser Tyr Gln Glu Gly Asp His Leu Gly Val Ile Pro
    690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
            740                 745                 750
```

Val Glu Leu Gln Asp Pro Val Thr Arg Thr Gln Leu Arg Ala Met Ala
    755                 760                 765

Ala Lys Thr Val Cys Pro Pro His Lys Val Leu Glu Ala Leu Leu
    770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Pro Arg Tyr Tyr Ser Ile Ser
            820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Glu Tyr Lys Gly Ile Ala
    850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
        915                 920                 925

Glu Ala His Leu Tyr Phe Gly Cys Arg Ser Pro His Glu Asp Tyr Leu
    930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
        995                1000                1005

Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys
    1025                1030                1035

Gly Arg Tyr Ala Lys Asp Val Trp Ala Gly
    1040                1045

<210> SEQ ID NO 3
<211> LENGTH: 664
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

```
Ser Arg Phe Asp Lys Glu Leu Ser Gln Pro Leu Lys Phe Leu Arg Asp
 65                  70                  75                  80

Phe Leu Gly Asp Gly Leu Ala Thr Ser Trp Thr His Glu Lys Asn Trp
                 85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Leu Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Arg Tyr
                245                 250                 255

Gln Ile Ile Thr Phe Leu Tyr Ala Gly Val Glu Gly Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
290                 295                 300

Tyr Lys Gln Val Lys Gln Leu Lys Tyr Val Gly Met Val Leu Asn Glu
305                 310                 315                 320

Ala Leu Arg Leu Trp Pro Thr Val Pro Tyr Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Val Trp Gly
        355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Ser
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Leu Leu Thr Leu Lys Pro Lys Gly Phe Val Val Lys Ala
        435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480
```

```
Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
            530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
                580                 585                 590

Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
            610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Asp Met Pro Leu Ala
                645                 650                 655

Lys Met His Gly Ala Phe Ser Thr
                660

<210> SEQ ID NO 4
<211> LENGTH: 145
<212> TYPE: PRT
<213> ORGANISM: Rhodothermus marinus

<400> SEQUENCE: 4

Met Ala Pro Thr Leu Ser Glu Gln Thr Arg Gln Leu Val Arg Ala Ser
1               5                   10                  15

Val Pro Ala Leu Gln Lys His Ser Val Ala Ile Ser Ala Thr Met Tyr
            20                  25                  30

Arg Leu Leu Phe Glu Arg Tyr Pro Glu Thr Arg Ser Leu Phe Glu Leu
        35                  40                  45

Pro Glu Arg Gln Ile His Lys Leu Ala Ser Ala Leu Leu Ala Tyr Ala
    50                  55                  60

Arg Ser Ile Asp Asn Pro Ser Ala Leu Gln Ala Ala Ile Arg Arg Met
65                  70                  75                  80

Val Leu Ser His Ala Arg Ala Gly Val Gln Ala Val His Tyr Pro Leu
                85                  90                  95

Val Trp Glu Cys Leu Arg Asp Ala Ile Lys Glu Val Leu Gly Pro Asp
            100                 105                 110

Ala Thr Glu Thr Leu Leu Gln Ala Trp Lys Glu Ala Tyr Asp Phe Leu
        115                 120                 125

Ala His Leu Leu Ser Thr Lys Glu Ala Gln Val Tyr Ala Val Leu Ala
    130                 135                 140

Glu
145

<210> SEQ ID NO 5
<211> LENGTH: 133
<212> TYPE: PRT
<213> ORGANISM: Methylacidiphilum infernorum
```

<400> SEQUENCE: 5

```
Met Ile Asp Gln Lys Glu Lys Glu Leu Ile Lys Glu Ser Trp Lys Arg
1               5                   10                  15

Ile Glu Pro Asn Lys Asn Glu Ile Gly Leu Leu Phe Tyr Ala Asn Leu
            20                  25                  30

Phe Lys Glu Glu Pro Thr Val Ser Val Leu Phe Gln Asn Pro Ile Ser
        35                  40                  45

Ser Gln Ser Arg Lys Leu Met Gln Val Leu Gly Ile Leu Val Gln Gly
    50                  55                  60

Ile Asp Asn Leu Glu Gly Leu Ile Pro Thr Leu Gln Asp Leu Gly Arg
65                  70                  75                  80

Arg His Lys Gln Tyr Gly Val Val Asp Ser His Tyr Pro Leu Val Gly
                85                  90                  95

Asp Cys Leu Leu Lys Ser Ile Gln Glu Tyr Leu Gly Gln Gly Phe Thr
            100                 105                 110

Glu Glu Ala Lys Ala Ala Trp Thr Lys Val Tyr Gly Ile Ala Ala Gln
        115                 120                 125

Val Met Thr Ala Glu
    130
```

<210> SEQ ID NO 6
<211> LENGTH: 140
<212> TYPE: PRT
<213> ORGANISM: Campylobacter jejuni

<400> SEQUENCE: 6

```
Met Thr Lys Glu Gln Ile Gln Ile Ile Lys Asp Cys Val Pro Ile Leu
1               5                   10                  15

Gln Lys Asn Gly Glu Asp Leu Thr Asn Glu Phe Tyr Lys Ile Met Phe
            20                  25                  30

Asn Asp Tyr Pro Glu Val Lys Pro Met Phe Asn Met Glu Lys Gln Ile
        35                  40                  45

Ser Gly Glu Gln Pro Lys Ala Leu Ala Met Ala Ile Leu Met Ala Ala
    50                  55                  60

Lys Asn Ile Glu Asn Leu Glu Asn Met Arg Ser Phe Val Asp Lys Val
65                  70                  75                  80

Ala Ile Thr His Val Asn Leu Gly Val Lys Glu Glu His Tyr Pro Ile
                85                  90                  95

Val Gly Ala Cys Leu Leu Lys Ala Ile Lys Asn Leu Leu Asn Pro Asp
            100                 105                 110

Glu Ala Thr Leu Lys Ala Trp Glu Val Ala Tyr Gly Lys Ile Ala Lys
        115                 120                 125

Phe Tyr Ile Asp Ile Glu Lys Lys Leu Tyr Asp Lys
    130                 135                 140
```

<210> SEQ ID NO 7
<211> LENGTH: 146
<212> TYPE: PRT
<213> ORGANISM: Vitreoscilla stercoraria

<400> SEQUENCE: 7

```
Met Leu Asp Gln Gln Thr Ile Asn Ile Ile Lys Ala Thr Val Pro Val
1               5                   10                  15

Leu Lys Glu His Gly Val Thr Ile Thr Thr Thr Phe Tyr Lys Asn Leu
            20                  25                  30
```

```
Phe Ala Lys His Pro Glu Val Arg Pro Leu Phe Asp Met Gly Arg Gln
             35                  40                  45

Glu Ser Leu Glu Gln Pro Lys Ala Leu Ala Met Thr Val Leu Ala Ala
 50                  55                  60

Ala Gln Asn Ile Glu Asn Leu Pro Ala Ile Leu Pro Ala Val Lys Lys
 65                  70                  75                  80

Ile Ala Val Lys His Cys Gln Ala Gly Val Ala Ala His Tyr Pro
                 85                  90                  95    Pro

Ile Val Gly Gln Glu Leu Leu Gly Ala Ile Lys Glu Val Leu Gly Asp
             100                 105                 110

Ala Ala Thr Asp Asp Ile Leu Asp Ala Trp Gly Lys Ala Tyr Gly Val
             115                 120                 125

Ile Ala Asp Val Phe Ile Gln Val Glu Ala Asp Leu Tyr Ala Gln Ala
             130                 135                 140

Val Glu
145
```

<210> SEQ ID NO 8
<211> LENGTH: 151
<212> TYPE: PRT
<213> ORGANISM: Mus musculus

<400> SEQUENCE: 8

```
Met Glu Arg Pro Glu Ser Glu Leu Ile Arg Gln Ser Trp Arg Val Val
 1               5                  10                  15

Ser Arg Ser Pro Leu Glu His Gly Thr Val Leu Phe Ala Arg Leu Phe
             20                  25                  30

Ala Leu Glu Pro Ser Leu Leu Pro Leu Phe Gln Tyr Asn Gly Arg Gln
             35                  40                  45

Phe Ser Ser Pro Glu Asp Cys Leu Ser Ser Pro Glu Phe Leu Asp His
 50                  55                  60

Ile Arg Lys Val Met Leu Val Ile Asp Ala Ala Val Thr Asn Val Glu
 65                  70                  75                  80

Asp Leu Ser Ser Leu Glu Glu Tyr Leu Thr Ser Leu Gly Arg Lys His
                 85                  90                  95

Arg Ala Val Gly Val Arg Leu Ser Ser Phe Ser Thr Val Gly Glu Ser
             100                 105                 110

Leu Leu Tyr Met Leu Glu Lys Cys Leu Gly Pro Asp Phe Thr Pro Ala
             115                 120                 125

Thr Arg Thr Ala Trp Ser Arg Leu Tyr Gly Ala Val Val Gln Ala Met
             130                 135                 140

Ser Arg Gly Trp Asp Gly Glu
145                 150
```

<210> SEQ ID NO 9
<211> LENGTH: 151
<212> TYPE: PRT
<213> ORGANISM: Homo sapiens

<400> SEQUENCE: 9

```
Met Glu Arg Pro Glu Pro Glu Leu Ile Arg Gln Ser Trp Arg Ala Val
 1               5                  10                  15

Ser Arg Ser Pro Leu Glu His Gly Thr Val Leu Phe Ala Arg Leu Phe
             20                  25                  30

Ala Leu Glu Pro Asp Leu Leu Pro Leu Phe Gln Tyr Asn Cys Arg Gln
             35                  40                  45
```

Phe Ser Ser Pro Glu Asp Cys Leu Ser Ser Pro Glu Phe Leu Asp His
    50                  55                  60

Ile Arg Lys Val Met Leu Val Ile Asp Ala Ala Val Thr Asn Val Glu
65                  70                  75                  80

Asp Leu Ser Ser Leu Glu Glu Tyr Leu Ala Ser Leu Gly Arg Lys His
                85                  90                  95

Arg Ala Val Gly Val Lys Leu Ser Ser Phe Ser Thr Val Gly Glu Ser
            100                 105                 110

Leu Leu Tyr Met Leu Glu Lys Cys Leu Gly Pro Ala Phe Thr Pro Ala
            115                 120                 125

Thr Arg Ala Ala Trp Ser Gln Leu Tyr Gly Ala Val Val Gln Ala Met
130                 135                 140

Ser Arg Gly Trp Asp Gly Glu
145                 150

<210> SEQ ID NO 10
<211> LENGTH: 154
<212> TYPE: PRT
<213> ORGANISM: Physeter catodon

<400> SEQUENCE: 10

Met Val Leu Ser Glu Gly Glu Trp Gln Leu Val Leu His Val Trp Ala
1               5                   10                  15

Lys Val Glu Ala Asp Val Ala Gly His Gly Gln Asp Ile Leu Ile Arg
            20                  25                  30

Leu Phe Lys Ser His Pro Glu Thr Leu Glu Lys Phe Asp Arg Phe Lys
        35                  40                  45

His Leu Lys Thr Glu Ala Glu Met Lys Ala Ser Glu Asp Leu Lys Lys
    50                  55                  60

His Gly Val Thr Val Leu Thr Ala Leu Gly Ala Ile Leu Lys Lys Lys
65                  70                  75                  80

Gly His His Glu Ala Glu Leu Lys Pro Leu Ala Gln Ser His Ala Thr
                85                  90                  95

Lys His Lys Ile Pro Ile Lys Tyr Leu Glu Phe Ile Ser Glu Ala Ile
            100                 105                 110

Ile His Val Leu His Ser Arg His Pro Gly Asp Phe Gly Ala Asp Ala
        115                 120                 125

Gln Gly Ala Met Asn Lys Ala Leu Glu Leu Phe Arg Lys Asp Ile Ala
    130                 135                 140

Ala Lys Tyr Lys Glu Leu Gly Tyr Gln Gly
145                 150

<210> SEQ ID NO 11
<211> LENGTH: 190
<212> TYPE: PRT
<213> ORGANISM: Homo sapiens

<400> SEQUENCE: 11

Met Glu Lys Val Pro Gly Glu Met Glu Ile Glu Arg Arg Glu Arg Ser
1               5                   10                  15

Glu Glu Leu Ser Glu Ala Glu Arg Lys Ala Val Gln Ala Met Trp Ala
            20                  25                  30

Arg Leu Tyr Ala Asn Cys Glu Asp Val Gly Val Ala Ile Leu Val Arg
        35                  40                  45

Phe Phe Val Asn Phe Pro Ser Ala Lys Gln Tyr Phe Ser Gln Phe Lys
    50                  55                  60

```
His Met Glu Asp Pro Leu Glu Met Glu Arg Ser Pro Gln Leu Arg Lys
 65                  70                  75                  80

His Ala Cys Arg Val Met Gly Ala Leu Asn Thr Val Val Glu Asn Leu
                 85                  90                  95

His Asp Pro Asp Lys Val Ser Ser Val Leu Ala Leu Val Gly Lys Ala
            100                 105                 110

His Ala Leu Lys His Lys Val Glu Pro Val Tyr Phe Lys Ile Leu Ser
        115                 120                 125

Gly Val Ile Leu Glu Val Val Ala Glu Glu Phe Ala Ser Asp Phe Pro
    130                 135                 140

Pro Glu Thr Gln Arg Ala Trp Ala Lys Leu Arg Gly Leu Ile Tyr Ser
145                 150                 155                 160

His Val Thr Ala Ala Tyr Lys Glu Val Gly Trp Val Gln Gln Val Pro
                165                 170                 175

Asn Ala Thr Thr Pro Pro Ala Thr Leu Pro Ser Ser Gly Pro
                180                 185                 190

<210> SEQ ID NO 12
<211> LENGTH: 338
<212> TYPE: PRT
<213> ORGANISM: Ascaris suum

<400> SEQUENCE: 12

Met Arg Ser Leu Leu Leu Leu Ser Ile Val Phe Phe Val Val Thr Val
  1               5                  10                  15

Ser Ala Asn Lys Thr Arg Glu Leu Cys Met Lys Ser Leu Glu His Ala
             20                  25                  30

Lys Val Asp Thr Ser Asn Glu Ala Arg Gln Asp Gly Ile Asp Leu Tyr
         35                  40                  45

Lys His Met Phe Glu Asn Tyr Pro Pro Leu Arg Lys Tyr Phe Lys Asn
     50                  55                  60

Arg Glu Glu Tyr Thr Ala Glu Asp Val Gln Asn Asp Pro Phe Phe Ala
 65                  70                  75                  80

Lys Gln Gly Gln Lys Ile Leu Leu Ala Cys His Val Leu Cys Ala Thr
                 85                  90                  95

Tyr Asp Asp Arg Glu Thr Phe Asn Ala Tyr Thr Arg Glu Leu Leu Asp
            100                 105                 110

Arg His Ala Arg Asp His Val His Met Pro Pro Glu Val Trp Thr Asp
        115                 120                 125

Phe Trp Lys Leu Phe Glu Glu Tyr Leu Gly Lys Lys Thr Thr Leu Asp
    130                 135                 140

Glu Pro Thr Lys Gln Ala Trp His Glu Ile Gly Arg Glu Phe Ala Lys
145                 150                 155                 160

Glu Ile Asn Lys His Gly Arg His Ala Val Arg His Gln Cys Met Arg
                165                 170                 175

Ser Leu Gln His Ile Asp Ile Gly His Ser Glu Thr Ala Lys Gln Asn
            180                 185                 190

Gly Ile Asp Leu Tyr Lys His Met Phe Glu Asn Tyr Pro Ser Met Arg
        195                 200                 205

Glu Ala Phe Lys Asp Arg Glu Asn Tyr Thr Ala Glu Asp Val Gln Lys
    210                 215                 220

Asp Pro Phe Phe Val Lys Gln Gly Gln Arg Ile Leu Leu Ala Cys His
225                 230                 235                 240

Leu Leu Cys Ala Ser Tyr Asp Asp Glu Glu Thr Phe His Met Tyr Val
                245                 250                 255
```

His Glu Leu Met Glu Arg His Glu Arg Leu Gly Val Gln Leu Pro Asp
            260                 265                 270

Gln His Trp Thr Asp Phe Trp Lys Leu Phe Glu Glu Phe Leu Glu Lys
            275                 280                 285

Lys Ser His Leu Cys Glu His Thr Lys His Ala Trp Ala Val Ile Gly
290                 295                 300

Lys Glu Phe Ala Tyr Glu Ala Thr Arg His Gly Lys Glu His His Glu
305                 310                 315                 320

His Lys Glu Glu His Lys Glu His Lys Glu Glu His Lys Glu Glu
            325                 330                 335

Gln His

<210> SEQ ID NO 13
<211> LENGTH: 132
<212> TYPE: PRT
<213> ORGANISM: Bacillus subtilis

<400> SEQUENCE: 13

Met Gly Gln Ser Phe Asn Ala Pro Tyr Glu Ala Ile Gly Glu Glu Leu
1               5                   10                  15

Leu Ser Gln Leu Val Asp Thr Phe Tyr Glu Arg Val Ala Ser His Pro
            20                  25                  30

Leu Leu Lys Pro Ile Phe Pro Ser Asp Leu Thr Glu Thr Ala Arg Lys
        35                  40                  45

Gln Lys Gln Phe Leu Thr Gln Tyr Leu Gly Gly Pro Pro Leu Tyr Thr
    50                  55                  60

Glu Glu His Gly His Pro Met Leu Arg Ala Arg His Leu Pro Phe Pro
65                  70                  75                  80

Ile Thr Asn Glu Arg Ala Asp Ala Trp Leu Ser Cys Met Lys Asp Ala
                85                  90                  95

Met Asp His Val Gly Leu Glu Gly Glu Ile Arg Glu Phe Leu Phe Gly
            100                 105                 110

Arg Leu Glu Leu Thr Ala Arg His Met Val Asn Gln Thr Glu Ala Glu
        115                 120                 125

Asp Arg Ser Ser
    130

<210> SEQ ID NO 14
<211> LENGTH: 195
<212> TYPE: PRT
<213> ORGANISM: Methanosarcina acetivorans

<400> SEQUENCE: 14

Met Ser Val Glu Lys Ile Pro Gly Tyr Thr Tyr Gly Glu Thr Glu Asn
1               5                   10                  15

Arg Ala Pro Phe Asn Leu Glu Asp Leu Lys Leu Leu Lys Glu Ala Val
            20                  25                  30

Met Phe Thr Ala Glu Asp Glu Glu Tyr Ile Gln Lys Ala Gly Glu Val
        35                  40                  45

Leu Glu Asp Gln Val Glu Glu Ile Leu Asp Thr Trp Tyr Gly Phe Val
    50                  55                  60

Gly Ser His Pro His Leu Leu Tyr Tyr Phe Thr Ser Pro Asp Gly Thr
65                  70                  75                  80

Pro Asn Glu Lys Tyr Leu Ala Ala Val Arg Lys Arg Phe Ser Arg Trp
                85                  90                  95

```
Ile Leu Asp Thr Cys Asn Arg Ser Tyr Asp Gln Ala Trp Leu Asp Tyr
                100                 105                 110

Gln Tyr Glu Ile Gly Leu Arg His His Arg Thr Lys Lys Asn Gln Thr
            115                 120                 125

Asp Asn Val Glu Ser Val Pro Asn Ile Gly Tyr Arg Tyr Leu Val Ala
        130                 135                 140

Phe Ile Tyr Pro Ile Thr Ala Thr Met Lys Pro Phe Leu Ala Arg Lys
145                 150                 155                 160

Gly His Thr Pro Glu Glu Val Glu Lys Met Tyr Gln Ala Trp Phe Lys
                165                 170                 175

Ala Thr Thr Leu Gln Val Ala Leu Trp Ser Tyr Pro Tyr Val Lys Tyr
            180                 185                 190

Gly Asp Phe
        195

<210> SEQ ID NO 15
<211> LENGTH: 195
<212> TYPE: PRT
<213> ORGANISM: Aeropyrum pernix

<400> SEQUENCE: 15

Met Thr Pro Ser Asp Ile Pro Gly Tyr Asp Tyr Gly Arg Val Glu Lys
1               5                   10                  15

Ser Pro Ile Thr Asp Leu Glu Phe Asp Leu Leu Lys Lys Thr Val Met
            20                  25                  30

Leu Gly Glu Lys Asp Val Met Tyr Leu Lys Lys Ala Cys Asp Val Leu
        35                  40                  45

Lys Asp Gln Val Asp Glu Ile Leu Asp Leu Trp Tyr Gly Trp Val Ala
    50                  55                  60

Ser Asn Glu His Leu Ile Tyr Tyr Phe Ser Asn Pro Asp Thr Gly Glu
65                  70                  75                  80

Pro Ile Lys Glu Tyr Leu Glu Arg Val Arg Ala Arg Phe Gly Ala Trp
                85                  90                  95

Ile Leu Asp Thr Thr Cys Arg Asp Tyr Asn Arg Glu Trp Leu Asp Tyr
                100                 105                 110

Gln Tyr Glu Val Gly Leu Arg His His Arg Ser Lys Lys Gly Val Thr
            115                 120                 125

Asp Gly Val Arg Thr Val Pro His Ile Pro Leu Arg Tyr Leu Ile Ala
        130                 135                 140

Phe Ile Tyr Pro Ile Thr Ala Thr Ile Lys Pro Phe Leu Ala Lys Lys
145                 150                 155                 160

Gly Gly Ser Pro Glu Asp Ile Glu Gly Met Tyr Asn Ala Trp Phe Lys
                165                 170                 175

Ser Val Val Leu Gln Val Ala Ile Trp Ser His Pro Tyr Thr Lys Glu
            180                 185                 190

Asn Asp Trp
        195

<210> SEQ ID NO 16
<211> LENGTH: 192
<212> TYPE: PRT
<213> ORGANISM: Pyrobaculum ferrireducens

<400> SEQUENCE: 16

Met Arg Glu Ile Pro Gly Tyr Glu Phe Gly Lys Val Pro Asp Ala Pro
1               5                   10                  15
```

Ile Ser Asp Glu Glu Phe Glu Leu Leu Lys Lys Ser Val Met Trp Thr
            20                  25                  30

Glu Glu Asp Glu Lys Tyr Arg Lys Leu Ala Cys Glu Val Leu Lys Gly
        35                  40                  45

Gln Val Glu Gln Ile Leu Asp Leu Trp Tyr Gly Trp Val Gly Ser Asn
    50                  55                  60

Pro His Leu Val Tyr Tyr Phe Gly Asp Arg Ser Gly Arg Pro Ile Pro
65                  70                  75                  80

Gln Tyr Leu Glu Ala Val Arg Lys Arg Phe Gly Gln Trp Ile Leu Asp
                85                  90                  95

Thr Val Cys Arg Ser Tyr Asp Arg Gln Trp Leu Asn Tyr Val Tyr Glu
            100                 105                 110

Ile Gly Leu Arg His His Arg Thr Lys Lys Gly Lys Thr Asp Gly Val
        115                 120                 125

Glu Thr Val Glu His Ile Pro Leu Arg Tyr Met Val Ala Phe Ile Ala
    130                 135                 140

Pro Ile Gly Leu Thr Ile Lys Pro Phe Leu Glu Lys Gly Gly His Pro
145                 150                 155                 160

Pro Asp Val Val Glu Lys Met Trp Ala Ala Trp Ile Lys Ser Val Val
                165                 170                 175

Leu Gln Val Ala Ile Trp Ser His Pro Tyr Ala Lys Pro Gly Glu Trp
            180                 185                 190

<210> SEQ ID NO 17
<211> LENGTH: 400
<212> TYPE: PRT
<213> ORGANISM: Cupriavidus necator

<400> SEQUENCE: 17

Met Leu Thr Gln Lys Thr Lys Asp Ile Val Lys Ala Thr Ala Pro Val
1               5                   10                  15

Leu Ala Glu His Gly Tyr Asp Ile Ile Lys Cys Phe Tyr Gln Arg Met
            20                  25                  30

Phe Glu Ala His Pro Glu Leu Lys Asn Val Phe Asn Met Ala His Gln
        35                  40                  45

Glu Gln Gly Gln Gln Gln Ala Leu Ala Arg Ala Val Tyr Ala Tyr
    50                  55                  60

Ala Glu Asn Ile Glu Asp Pro Asn Ser Leu Met Ala Val Leu Lys Asn
65                  70                  75                  80

Ile Ala Asn Lys His Ala Ser Leu Gly Val Lys Pro Glu Gln Tyr Pro
                85                  90                  95

Ile Val Gly Glu His Leu Leu Ala Ala Ile Lys Glu Val Leu Gly Asn
            100                 105                 110

Ala Ala Thr Asp Asp Ile Ile Ser Ala Trp Ala Gln Ala Tyr Gly Asn
        115                 120                 125

Leu Ala Asp Val Leu Met Gly Met Glu Ser Glu Leu Tyr Glu Arg Ser
    130                 135                 140

Ala Glu Gln Pro Gly Gly Trp Lys Gly Trp Arg Thr Phe Val Ile Arg
145                 150                 155                 160

Glu Lys Arg Pro Glu Ser Asp Val Ile Thr Ser Phe Ile Leu Glu Pro
                165                 170                 175

Ala Asp Gly Gly Pro Val Val Asn Phe Glu Pro Gly Gln Tyr Thr Ser
            180                 185                 190

Val Ala Ile Asp Val Pro Ala Leu Gly Leu Gln Gln Ile Arg Gln Tyr
        195                 200                 205

```
Ser Leu Ser Asp Met Pro Asn Gly Arg Ser Tyr Arg Ile Ser Val Lys
    210                 215                 220

Arg Glu Gly Gly Gly Pro Gln Pro Gly Tyr Val Ser Asn Leu Leu
225                 230                 235                 240

His Asp His Val Asn Val Gly Asp Gln Val Lys Leu Ala Ala Pro Tyr
                245                 250                 255

Gly Ser Phe His Ile Asp Val Asp Ala Lys Thr Pro Ile Val Leu Ile
                260                 265                 270

Ser Gly Gly Val Gly Leu Thr Pro Met Val Ser Met Leu Lys Val Ala
        275                 280                 285

Leu Gln Ala Pro Pro Arg Gln Val Val Phe Val His Gly Ala Arg Asn
    290                 295                 300

Ser Ala Val His Ala Met Arg Asp Arg Leu Arg Glu Ala Ala Lys Thr
305                 310                 315                 320

Tyr Glu Asn Leu Asp Leu Phe Val Phe Tyr Asp Gln Pro Leu Pro Glu
                325                 330                 335

Asp Val Gln Gly Arg Asp Tyr Asp Tyr Pro Gly Leu Val Asp Val Lys
                340                 345                 350

Gln Ile Glu Lys Ser Ile Leu Leu Pro Asp Ala Asp Tyr Tyr Ile Cys
                355                 360                 365

Gly Pro Ile Pro Phe Met Arg Met Gln His Asp Ala Leu Lys Asn Leu
    370                 375                 380

Gly Ile His Glu Ala Arg Ile His Tyr Glu Val Phe Gly Pro Asp Leu
385                 390                 395                 400

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 18

His His His His His His
1               5
```

METHOD FOR ENANTIOSELECTIVE CARBENE C—H INSERTION USING AN IRON-CONTAINING PROTEIN CATALYST

CROSS-REFERENCES TO RELATED APPLICATIONS

The present application claims priority to U.S. Provisional Pat. Appl. No. 62/621,749, filed Jan. 25, 2018; U.S. Provisional Pat. Appl. No. 62/693,547, filed Jul. 3, 2018; and U.S. Provisional Pat. Appl. No. 62/734,059, filed Sep. 20, 2018; which applications are incorporated herein by reference in their entirety.

REFERENCE TO A SEQUENCE LISTING

The instant application contains a Sequence Listing which has been submitted electronically in ASCII format and is hereby incorporated by reference in its entirety. Said ASCII copy, created on Mar. 19, 2019, is named 086544-1115817_021910US_SL.txt and is 44,829 bytes in size.

STATEMENT AS TO RIGHTS TO INVENTIONS MADE UNDER FEDERALLY SPONSORED RESEARCH AND DEVELOPMENT

This invention was made with government support under Grant Nos. MCB1513007 and DGE1144469 awarded by the National Science Foundation. The government has certain rights in the invention.

BACKGROUND OF THE INVENTION

Direct functionalization of the ubiquitous C—H bond represents a powerful approach to the synthesis of organic molecules, both for the construction of complex molecules as well as for transforming simple hydrocarbon feedstocks to value-added chemicals. In fact, as carbon is the backbone of all organic molecules, the ability to selectively form a C—C bond from a C—H bond is transformative for these applications. Complementary to the traditional chemical synthesis approach which relies on the manipulation of pre-installed functional groups, a catalytic and selective approach for transforming C—H bonds to C—C bonds will increase scientists' access of chemical space by providing a means to make new molecules and as a tool for streamlining synthetic routes to existing ones.

The majority of reported small molecule catalysts for metal-carbene C—H insertion are complexes of rhodium, iridium, copper, or ruthenium, with rhodium-based catalysts the most developed. There are only a few examples of catalytic iron-carbene insertion into $sp^3$ C—H bonds. In one representative report, it was disclosed that at elevated temperatures (80-110° C.), iron-porphyrin complexes could decompose diazomalonate or methyl 2-phenyldiazoacetates and add their corresponding carbene fragments to alkane C—H bonds. Site-selectivity posed a major challenge with this system: even simple alkane substrates such as mesitylene produced mixtures of products. Since similar elevated temperatures are known to thermally induce the generation of highly reactive free carbene intermediates, which can then non-selectively insert into C—H bonds, improving the site-selectivity of this system would likely be challenging. More recently, iron-phthalocyanine complexes were reported to catalyze intramolecular $sp^3$ C—H insertion using acceptor/acceptor diazo moieties to benzylic and allylic C—H bonds. However, this catalytic system was only demonstrated with intramolecular examples, in which the C—H bond is necessarily contained in the same molecule as the reactive intermediate, severely limiting its synthetic utility. In addition, the catalysts in both reports are achiral and therefore only capable of forming racemic mixtures of the product.

Previous attempts at developing biocatalysts for this type of reaction have relied on metal-ion replacement. Using this strategy, heme proteins in which the native iron-porphyrin cofactor has been replaced with an iridium-porphyrin complex have been shown to be competent at carbene C—H insertion reactions. The substrate profile and resulting products of these iridium-porphyrin protein complexes are similar to that of earlier reported iridium-porphyrin and other iridium-based small molecule catalysts, with the protein scaffold responsible for enforcing enantioselectivity. In one report, the authors note the following in regard to developing new-to-nature transformations for heme proteins: "However, the reactivity of the Fe-center in heme proteins limits the scope of these transformations. For example, Fe-PIX proteins . . . catalyze insertions of carbenes into reactive N—H and S—H bonds, but they do not catalyze the insertion into less reactive C—H bonds." See, Key, et al. *Nature* 534, 534-537 (2016). Such comments reflect the generally held hypothesis that the iron-carbene is less reactive that the rhodium-carbene or iridium-carbene, and thereof not as competent for insertion into C—H bonds.

BRIEF SUMMARY OF THE INVENTION

Provided herein are catalysts, reaction mixtures, and methods for producing functionalized C—H insertion products. Reaction mixtures according to the present disclosure include a substrate having an $sp^3$-hybridized C—H bond, a carbene precursor for modification of the carbon atom in the $sp^3$-hybridized C—H bond, and a heme protein comprising an iron porphyrin.

Methods for producing C—H insertion products according to the present disclosure include:
(a) providing a substrate having an $sp^3$-hybridized C—H bond, a carbene precursor for modification of the carbon atom in the $sp^3$-hybridized C—H bond, and a heme protein comprising an iron porphyrin; and
(b) admixing the components of step (a) under conditions sufficient to produce the C—H insertion product.

Heme protein variants useful for catalysis of C—H insertion reactions according to the present disclosure include proteins having an iron porphyrin and a cytochrome P450 polypeptide, wherein the cytochrome P450 polypeptide comprises one or more amino acid mutations that increase the C—H insertion activity of the enzyme variant relative to the cytochrome P450 polypeptide without the amino acid mutations.

BRIEF DESCRIPTION OF THE DRAWINGS

FIG. 3A shows the domain architecture of cytochrome P450BM3. For its native monooxygenase activity, the FMN and FAD domains, collectively called the reductase domain, are responsible for delivering the necessary reducing equivalents from NADPH to the heme domain. The end of the FMN domain and the fragment of the polypeptide chain included in the ΔFAD complex were chosen based on a report by Govindaraj and Poulos.

FIG. 3B shows the systematic truncation of the P411-gen6 full-length protein to construct P411-gen6b (P411ΔFAD-gen6, amino acids 1-664) and P411-gen6 heme-domain only (amino acids 1-463). Both P411-gen6b (ΔFAD) and the heme domain only protein delivered 3a with higher total turnover compared with the full-length protein. Standard reaction conditions: lysate of *E. coli* with 2.0 μM heme protein, 10 mM 1a, 10 mM 2, and 1 mM $Na_2S_2O_4$ (unless otherwise indicated). TTN results are an average of at least duplicate reactions. RT=room temperature; TTN=total turnover number. 5 mM Dithionite was used in reactions marked with †.

FIG. 4 shows the kinetic isotope effects of C—H alkylation catalyzed by P411-CHF.

DETAILED DESCRIPTION OF THE INVENTION

Figure 1A:
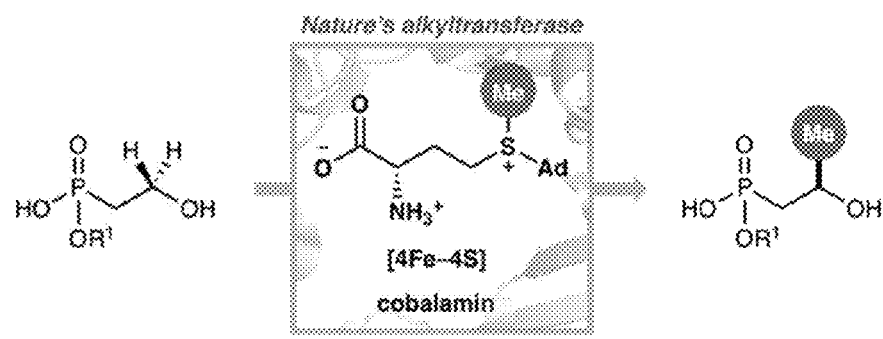
FIG. 1A shows methylation catalyzed by cobalamin-dependent radical SAM enzymes, as illustrated by Fom3 in fosfomycin biosynthesis.

Installing a carbon-carbon (C—C) bond in place of a sp$^3$-hybridized carbon-hydrogen (C—H) bond is one of the most attractive strategies for building molecules. Though abundant in organic molecules, C—H bonds are typically considered unreactive and unavailable for chemical manipulation. Recent advances in C—H functionalization technology, however, have begun to transform the logic of chemical synthesis, while emphasizing the importance of and challenges associated with selective reactions at sp$^3$-hybridized carbon atoms in hydrocarbon frameworks.

Described herein are the first catalysts for enantio-, regio-, and chemo-selective intermolecular alkylation of sp$^3$ C—H bonds through iron-carbene C—H insertion. The catalysts, derived from heme proteins such as a cytochrome P450 enzyme whose native cysteine axial ligand has been substituted for serine ("cytochrome P411"), are fully genetically encoded and produced efficiently in bacteria, where they can be tuned by directed evolution for desired activity and selectivity. That these proteins activate iron, the most abundant transition metal, to perform this challenging chemistry provides a desirable alternative to noble metal catalysts, which have dominated the field of C—H functionalization.

The laboratory-evolved enzymes functionalize diverse alkanes containing benzylic, allylic, or α-amino C—H bonds with high turnover and exquisite selectivity. The proteins utilize diazo compounds, such as α-diazo esters, α-diazo amides, and α-diazo ketones, for intermolecular carbene insertion into sp³ C—H bonds. These catalysts are capable of functionalizing sp³ C—H bonds in diverse substrates with up to thousands of total turnover numbers (up to 3750 turnovers to product) and good to excellent enantioselectivity (up to >99:1 e.r.). In many cases, selective C—H alkylation can be achieved in the presence of other reactive C—H bonds and/or functional groups. Furthermore, these highly efficient enzymes have enabled the development of concise routes to several natural products. The demonstration that these enzymes mediate sp³ C—H alkylation using their native iron-heme cofactor unlocks a vast natural heme protein diversity for this useful but abiological transformation and will facilitate the development of new enzymatic C—H functionalization reactions for applications in chemistry and synthetic biology.

I. DEFINITIONS

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the reagent" includes reference to one or more reagents known to those skilled in the art, and so forth.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The terms "heme protein variant" and "heme enzyme variant" include any heme-containing protein comprising at least one amino acid mutation with respect to wild-type and also include any chimeric protein comprising recombined sequences or blocks of amino acids from two, three, or more different heme-containing enzymes.

The term "whole cell catalyst" includes cells expressing heme-containing enzymes, wherein the whole cell catalyst displays carbon-carbon bond formation activity.

The term "carbene precursor" includes molecules that can be decomposed in the presence of metal (or enzyme) catalysts to form structures that contain at least one divalent carbon with two unshared valence shell electrons (i.e., carbenes) and that can be transferred to a carbon-hydrogen bond form various carbon ligated products. Examples of carbene precursors include, but are not limited to, diazo reagents, diazirine reagents, and hydrazone reagents.

As used herein, the term "anaerobic," when used in reference to a reaction, culture or growth condition, is intended to mean that the concentration of oxygen is less than about 25 μM, preferably less than about 5 μM, and even more preferably less than 1 μM. The term is also intended to include sealed chambers of liquid or solid medium maintained with an atmosphere of less than about 1% oxygen. Preferably, anaerobic conditions are achieved by sparging a reaction mixture with an inert gas such as nitrogen or argon.

As used herein, the term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can refer to alkyl groups having up to 20 carbons atoms, such as, but not limited to heptyl, octyl, nonyl, decyl, etc. Alkyl groups can be unsubstituted or substituted. For example, "substituted alkyl" groups can be substituted with one or more moieties selected from halo, hydroxy, amino, alkylamino, alkoxy, haloalkyl, carboxy, amido, nitro, oxo, and cyano.

As used herein, the term "alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be unsubstituted or substituted. For example, "substituted alkenyl" groups can be substituted with one or more moieties selected from halo, hydroxy, amino, alkylamino, alkoxy, haloalkyl, carboxy, amido, nitro, oxo, and cyano.

As used herein, the term "alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be unsubstituted or substituted. For example, "substituted alkynyl" groups can be substituted with one or more moieties selected from halo, hydroxy, amino, alkylamino, alkoxy, haloalkyl, carboxy, amido, nitro, oxo, and cyano.

As used herein, the term "aryl" refers to an aromatic carbon ring system having any suitable number of ring atoms and any suitable number of rings. Aryl groups can include any suitable number of carbon ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be unsubstituted or substituted. For example, "substituted aryl" groups can be substituted with one or more moieties selected from halo, hydroxy, amino, alkylamino, alkoxy, haloalkyl, carboxy, amido, nitro, oxo, and cyano.

As used herein, the term "cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, and $C_{6-8}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. Cycloalkyl groups can be unsubstituted or substituted. For example, "substituted cycloalkyl" groups can be substituted with one or more moieties selected from halo, hydroxy, amino, alkylamino, alkoxy, haloalkyl, carboxy, amido, nitro, oxo, and cyano.

As used herein, the term "heterocyclyl" refers to a saturated ring system having from 3 to 12 ring members and from 1 to 4 heteroatoms selected from N, O and S. Additional heteroatoms including, but not limited to, B, Al, Si and P can also be present in a heterocycloalkyl group. The heteroatoms can be oxidized to form moieties such as, but not limited to, —S(O)— and —S(O)$_2$—. Heterocyclyl groups can include any number of ring atoms, such as, 3 to 6, 4 to 6, 5 to 6, 4 to 6, or 4 to 7 ring members. Any suitable number of heteroatoms can be included in the heterocyclyl groups, such as 1, 2, 3, or 4, or 1 to 2, 1 to 3, 1 to 4, 2 to 3, 2 to 4, or 3 to 4. Examples of heterocyclyl groups include, but are not limited to, aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. Heterocyclyl groups can be unsubstituted or substituted. For example, "substituted heterocyclyl" groups can be substituted with one or more moieties selected from halo, hydroxy, amino, alkylamino, alkoxy, haloalkyl, carboxy, amido, nitro, oxo, and cyano.

As used herein, the term "heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms including, but not limited to, B, Al, Si and P can also be present in a heteroaryl group. The heteroatoms can be oxidized to form moieties such as, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. Examples of heteroaryl groups include, but are not limited to, pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. Heteroaryl groups can be unsubstituted or substituted. For example, "substituted heteroaryl" groups can be substituted with one or more moieties selected from halo, hydroxy, amino, alkylamino, alkoxy, haloalkyl, carboxy, amido, nitro, oxo, and cyano.

As used herein, the term "alkoxy" refers to an alkyl group having an oxygen atom that connects the alkyl group to the point of attachment: i.e., alkyl-O—. As for alkyl group, alkoxy groups can have any suitable number of carbon atoms, such as $C_{1-6}$ or $C_{1-4}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. Alkoxy groups can be unsubstituted or substituted. For example, "substituted alkoxy" groups can be substituted with one or more moieties selected from halo, hydroxy, amino, alkylamino, alkoxy, haloalkyl, carboxy, amido, nitro, oxo, and cyano.

As used herein, the term "alkylthio" refers to an alkyl group having a sulfur atom that connects the alkyl group to the point of attachment: i.e., alkyl-S—. As for alkyl groups, alkylthio groups can have any suitable number of carbon atoms, such as $C_{1-6}$ or $C_{1-4}$. Alkylthio groups include, for example, methoxy, ethoxy, propoxy, iso-propoxy, butoxy, 2-butoxy, iso-butoxy, sec-butoxy, tert-butoxy, pentoxy, hexoxy, etc. groups can be unsubstituted or substituted. For example, "substituted alkylthio" groups can be substituted with one or more moieties selected from halo, hydroxy, amino, alkylamino, alkoxy, haloalkyl, carboxy, amido, nitro, oxo, and cyano.

As used herein, the terms "halo" and "halogen" refer to fluorine, chlorine, bromine and iodine.

As used herein, the term "haloalkyl" refers to an alkyl moiety as defined above substituted with at least one halogen atom.

As used herein, the term "alkylsilyl" refers to a moiety —SiR$_3$, wherein at least one R group is alkyl and the other R groups are H or alkyl. The alkyl groups can be substituted with one or more halogen atoms.

As used herein, the term "acyl" refers to a moiety —C(O)R, wherein R is an alkyl group.

As used herein, the term "oxo" refers to an oxygen atom that is double-bonded to a compound (i.e., O═).

As used herein, the term "carboxy" refers to a moiety —C(O)OH. The carboxy moiety can be ionized to form the carboxylate anion. "Alkyl carboxylate" refers to a moiety —C(O)OR, wherein R is an alkyl group as defined herein.

As used herein, the term "amino" refers to a moiety —NR$_3$, wherein each R group is H or alkyl.

As used herein, the term "amido" refers to a moiety —NRC(O)R or —C(O)NR$_2$, wherein each R group is H or alkyl.

The terms "protein," "peptide," and "polypeptide" are used interchangeably herein to refer to a polymer of amino acid residues, or an assembly of multiple polymers of amino acid residues. The terms apply to amino acid polymers in which one or more amino acid residues are an artificial chemical mimic of a corresponding naturally occurring amino acid, as well as to naturally occurring amino acid polymers and non-naturally occurring amino acid polymers.

The term "amino acid" includes naturally-occurring α-amino acids and their stereoisomers, as well as unnatural (non-naturally occurring) amino acids and their stereoisomers. "Stereoisomers" of amino acids refers to mirror image isomers of the amino acids, such as L-amino acids or D-amino acids. For example, a stereoisomer of a naturally-occurring amino acid refers to the mirror image isomer of the naturally-occurring amino acid, i.e., the D-amino acid.

Naturally-occurring amino acids are those encoded by the genetic code, as well as those amino acids that are later modified, e.g., hydroxyproline, γ-carboxyglutamate and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural (non-naturally occurring) amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" are unnatural amino acids that have the same basic chemical structure as naturally-occurring amino acids, i.e., an α carbon that is bound to a hydrogen, a carboxyl group, an amino group, but have modified R (i.e., side-chain) groups or modified peptide backbones, e.g., homoserine, norleucine, methionine sulfoxide, methionine methyl sulfonium. "Amino acid mimetics" refer to chemical compounds that have a structure that is different from the general chemical structure of an amino acid, but that functions in a manner similar to a naturally-occurring amino acid.

Amino acids may be referred to herein by either their commonly known three letter symbols or by the one-letter symbols recommended by the IUPAC-IUB Biochemical Nomenclature Commission. For example, an L-amino acid may be represented herein by its commonly known three letter symbol (e.g., Arg for L-arginine) or by an upper-case one-letter amino acid symbol (e.g., R for L-arginine). A D-amino acid may be represented herein by its commonly known three letter symbol (e.g., D-Arg for D-arginine) or by a lower-case one-letter amino acid symbol (e.g., r for D-arginine).

With respect to amino acid sequences, one of skill in the art will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acid includes, without limitation, a naturally-occurring amino acid such as an L-amino acid, a stereoisomer of a naturally occurring amino acid such as a D-amino acid, and an unnatural amino acid such as an amino acid analog, amino acid mimetic, synthetic amino acid, N-substituted glycine, and N-methyl amino acid.

Conservative substitution tables providing functionally similar amino acids are well known in the art. For example, substitutions may be made wherein an aliphatic amino acid (e.g., G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins,* 1993).

The term "oligonucleotide," "nucleic acid," "nucleotide," or "polynucleotide" refers to deoxyribonucleic acids (DNA) or ribonucleic acids (RNA) and polymers thereof in either single-, double- or multi-stranded form. The term includes, but is not limited to, single-, double- or multi-stranded DNA or RNA, genomic DNA, cDNA, DNA-RNA hybrids, or a polymer comprising purine and/or pyrimidine bases or other natural, chemically modified, biochemically modified, non-natural, synthetic or derivatized nucleotide bases. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), orthologs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991), Ohtsuka et al., *J. Biol. Chem.* 260:2605-2608 (1985), and Rossolini et al., *Mol. Cell. Probes* 8:91-98 (1994)). The term nucleic acid is used interchangeably with gene, cDNA, and mRNA encoded by a gene.

The term "site-directed mutagenesis" refers to various methods in which specific changes are intentionally made introduced into a nucleotide sequence (i.e., specific nucleotide changes are introduced at pre-determined locations). Known methods of performing site-directed mutagenesis include, but are not limited to, PCR site-directed mutagenesis, cassette mutagenesis, whole plasmid mutagenesis, and Kunkel's method.

The term "site-saturation mutagenesis," also known as "saturation mutagenesis," refers to a method of introducing random mutations at predetermined locations with a nucleotide sequence, and is a method commonly used in the context of directed evolution (e.g., the optimization of proteins (e.g., in order to enhance activity, stability, and/or stability), metabolic pathways, and genomes). In site-saturation mutagenesis, artificial gene sequences are synthesized using one or more primers that contain degenerate codons; these degenerate codons introduce variability into the position(s) being optimized. Each of the three positions within a degenerate codon encodes a base such as adenine (A), cytosine (C), thymine (T), or guanine (G), or encodes a degenerate position such as K (which can be G or T), M (which can be A or C), R (which can be A or G), S (which can be C or G), W (which can be A or T), Y (which can be C or T), B (which can be C, G, or T), D (which can be A, G, or T), H (which can be A, C, or T), V (which can be A, C, or G), or N (which can be A, C, G, or T). Thus, as a non-limiting example, the degenerate codon NDT encodes an A, C, G, or T at the first position, an A, G, or T at the second position, and a T at the third position. This particular combination of 12 codons represents 12 amino acids (Phe, Leu, Ile, Val, Tyr, His, Asn, Asp, Cys, Arg, Ser, and Gly). As another non-limiting example, the degenerate codon VHG encodes an A, C, or G at the first position, an A, C, or T at the second position, and G at the third position. This particular combination of 9 codons represents 8 amino acids (Lys, Thr, Met, Glu, Pro, Leu, Ala, and Val). As another non-limiting example, the "fully randomized" degenerate codon NNN includes all 64 codons and represents all 20 naturally-occurring amino acids.

In some instances, a mixture of degenerate primers is used. A mixture of degenerate primers can contain any number of different degenerate primers in any ratio. As a non-limiting example, a mixture of primers containing the NDT, VHG, and TGG primers can be used. Such a mixture can contain, for example, an amount of each primer in a 12:9:1 ratio (e.g., a NDT:VHG:TGG ratio of 12:9:1). Based on various considerations, non-limiting examples being desired redundancy, the desired presence of stop codons, and/or desired amino acid characteristics (e.g., the presence of nonpolar residues, charged residues, or small side chain residues), different combinations of degenerate primers can be used. Considerations and methods for choosing optimal combinations of degenerate primers will be known to one of skill in the art.

The term "nucleotide sequence encoding a peptide" means the segment of DNA involved in producing a peptide chain. The term can include regions preceding and following the coding region (leader and trailer) involved in the transcription/translation of a gene product and the regulation of the transcription/translation, as well as intervening sequences (introns) between individual coding segments (exons).

The term "homolog," as used herein with respect to an original enzyme or gene of a first family or species, refers to distinct enzymes or genes of a second family or species which are determined by functional, structural or genomic analyses to be an enzyme or gene of the second family or species which corresponds to the original enzyme or gene of the first family or species. Homologs most often have functional, structural, or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the amino acid sequence encoded by a gene has a similar amino acid sequence to that of the second gene. Alternatively, a protein has homology to a second protein if the two proteins have "similar" amino acid sequences. Thus, the term "homologous proteins" is intended to mean that the two proteins have similar amino acid sequences. In particular embodiments, the homology between two proteins is indicative of its shared ancestry, related by evolution.

II. REACTION MIXTURES AND METHODS FOR THE PREPARATION OF C—H INSERTION PRODUCTS

Provided herein are catalysts, reaction mixtures, and methods for producing C—H insertion products. Substrates accessible to iron-carbene C—H insertion have previously been largely unexplored. In the work described herein, iron-containing proteins have a substrate profile complementary to existing catalysts.

Reaction mixtures according to the present disclosure include a substrate having an $sp^3$-hybridized C—H bond, a carbene precursor for modification of the carbon atom in the $sp^3$-hybridized C—H bond, and a heme protein comprising an iron porphyrin. The $sp^3$-hybridized C—H bond targeted for modification may be in the same molecule as the carbene precursor, or in a second compound. The heme protein activates the carbene precursor (e.g., an acceptor-only carbene precursors), to add to $sp^3$ C—H bonds of diverse linear and cyclic substrates, thereby expanding the scope of contemporary C—H functionalization technologies.

The reaction mixtures can be employed for the preparation of C—H insertion products via intermolecular insertion reactions, i.e., wherein the carbene precursor and the substrate having the $sp^3$-hybridized C—H bond are separate compounds. In contrast to the iron catalysis described herein, previous systems for intermolecular C—H insertion have relied on rhodium catalysis or iridium catalysis. Known catalysts for rhodium mediated intermolecular carbene C—H insertion utilize donor-acceptor carbene precursors, in which the carbene carbon is substituted with one electron-donating group (e.g., an aryl group or vinyl group) and one electron-withdrawing group (e.g., an ester), and can add the corresponding carbene fragments to diverse alkanes. While iridium complexes can perform intermolecular carbene C—H insertion using both acceptor-only type carbene precursors (where the carbene atom is substituted with one hydrogen and one electron-withdrawing group) and donor-acceptor type carbene precursors, these catalysts are generally limited to functionalizing activated C—H bonds in cyclic substrates.

In some embodiments, the C—H insertion reaction is an intermolecular reaction and the substrate having the $sp^3$-hybridized C—H bond is a compound according to Formula I:

(I)

wherein:
$R^1$, $R^2$, and $R^3$ are independently selected from the group consisting of H, $C_{1-18}$ alkyl, $C_{2-18}$ alkenyl, $C_{2-18}$ alkynyl, 2- to 18-membered heteroalkyl, $C_{1-18}$ haloalkyl, $C_{1-18}$ alkoxy, $C_{3-10}$ cycloalkyl, $C_{6-10}$ aryl, 3- to 10-membered heterocyclyl, 5- to 10-membered heteroaryl, —C(O)R$^8$, —C(O)OR$^8$, —C(O)SR$^8$, —C(O)N(R$^8$)$_2$, —N(R$^9$)$_2$, —B(R$^{10}$)$_2$, —Si(R$^{10}$)$_3$, —P(R$^{10}$)$_3$, and —P(R$^{10}$)$_4$; or $R^1$ and $R^2$ are taken together to form $C_{3-10}$ cycloalkyl, $C_{6-10}$ aryl, 3- to 10-membered heterocyclyl, and 5- to 10-membered heteroaryl, each of which is optionally substituted;

each $R^8$, $R^9$, and $R^{10}$ is independently selected from the group consisting of H, $C_{1-18}$ alkyl, $C_{2-18}$ alkenyl, —OH, oxo, $C_{1-18}$ alkoxy, $C_{2-18}$ alkynyl, $C_{6-10}$ aryl, 5- to 10-membered heteroaryl, and 3- to 10-membered heterocyclyl; and each of $R^1$, $R^2$, $R^3$, $R^8$, $R^9$, and $R^{10}$ is optionally and independently substituted.

In some embodiments, the substrate is a compound according to Formula I wherein:

$R^1$ is selected from the group consisting of $C_{1-18}$ alkyl, 2- to 18-membered heteroalkyl, $C_{1-18}$ haloalkyl, $C_{1-18}$ alkoxy, $C_{2-18}$ alkenyl, $C_{2-18}$ alkynyl, $C_{3-10}$ cycloalkyl, $C_{6-10}$ aryl, 3- to 10-membered heterocyclyl, and 5- to 10-membered heteroaryl, each of which is optionally substituted; and $R^2$ and $R^3$ are independently selected from the group consisting of H, $C_{1-18}$ alkyl, 2- to 18-membered heteroalkyl, $C_{1-18}$ haloalkyl, $C_{1-18}$ alkoxy, $C_{2-18}$ alkenyl, $C_{2-18}$ alkynyl, $C_{3-10}$ cycloalkyl, $C_{6-10}$ aryl, 3- to 10-membered heterocyclyl, and 5- to 10-membered heteroaryl, each of which is optionally substituted; or $R^1$ and $R^2$ are taken together to form $C_{3-10}$ cycloalkyl, $C_{6-10}$ aryl, 3- to 10-membered heterocyclyl, and 5- to 10-membered heteroaryl, each of which is optionally substituted.

In some embodiments, the substrate having the sp$^3$-hybridized C—H bond is a compound according to Formula Ia:

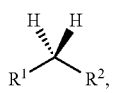
(Ia)

wherein:
$R^1$ is selected from the group consisting of optionally substituted $C_{1-18}$ alkyl, 2- to 18-membered heteroalkyl, $C_{1-18}$ alkoxy, $C_{3-10}$ cycloalkyl, $C_{1-18}$ fluoroalkyl, substituted $C_{6-10}$ aryl, and substituted 5- to 10-membered heteroaryl; and $R^2$ is independently selected from the group consisting of H, $C_{1-18}$ alkyl, 2- to 18-membered heteroalkyl, $C_{1-18}$ alkoxy, $C_{3-10}$ cycloalkyl, $C_{1-18}$ fluoroalkyl, substituted $C_{6-10}$ aryl, and substituted 5- to 10-membered heteroaryl; or $R^1$ and $R^2$ are taken together to form $C_{3-10}$ cycloalkyl, $C_{6-10}$ aryl, 3- to 10-membered heterocyclyl, and 5- to 10-membered heteroaryl, each of which is optionally substituted.

In some embodiments, $R^1$ is $C_{6-10}$ aryl, $C_{1-8}$ alkyl substituted with $C_{6-10}$ aryl, or $C_{2-8}$ alkenyl substituted with $C_{6-10}$ aryl. In each instance, $C_{6-10}$ aryl can be substituted or unsubstituted. In some embodiments, $C_{6-10}$ aryl is substituted with one to five substituents independently selected from halogen, —OH, —NO$_2$; —CN; —N$_3$; $C_{1-6}$ alkyl, $C_{1-6}$ alkoxy, $C_{1-6}$ haloalkyl, and $C_{1-18}$ alkylsilyl. In some embodiments, $C_{6-10}$ aryl is substituted with one to 5 substituents independently selected from $C_{1-6}$ alkyl, $C_{1-6}$ alkoxy, $C_{1-6}$ haloalkyl, and $C_{1-18}$ alkylsilyl. In some embodiments, $R^1$ is phenyl, benzyl, or styryl, each of which is optionally substituted with one to five substituents on the aromatic ring.

In some embodiments, $R^2$ is $C_{1-8}$ alkyl, $C_{1-8}$ alkoxy, or $C_{2-8}$ alkenyl. In some embodiments, $R^2$ is $C_{1-8}$ alkyl, $C_{1-8}$ alkoxy, or $C_{2-8}$ alkenyl, and $R^1$ is $C_{6-10}$ aryl, $C_{1-8}$ alkyl substituted with $C_{6-10}$ aryl, or $C_{2-8}$ alkenyl substituted with $C_{6-10}$ aryl, which can be further substituted as described above.

In some embodiments, $R^1$ is $C_{1-8}$ alkyl, $C_{2-8}$ alkenyl, or $C_{2-8}$ alkynyl, each of which is optionally substituted with one or more substituents (e.g., 1-6 substituents, or 1-3 substituents, or 1-2 substituents) independently selected from halogen, —OH, —NO$_2$; —CN; —N$_3$; $C_{1-6}$ alkyl, $C_{1-6}$ alkoxy, $C_{1-6}$ haloalkyl, $C_{1-18}$ alkylsilyl, unsubstituted $C_{6-10}$ aryl, and substituted $C_{6-10}$ aryl. In some such embodiments, $R^2$ is $C_{1-8}$ alkyl or $C_{1-8}$ alkoxy.

In some embodiments, $R^1$ and $R^2$ are taken together to form $C_{3-10}$ cycloalkyl or 3- to 10-membered heterocyclyl, each of which is optionally substituted. For example, $R^1$ and $R^2$ can be taken together with the central carbon atom in compounds of Formula I or Formula Ia to form tetrahydrofuranyl, tetrahydropyranyl, piperidinyl, or pyrrolidinyl, which is optionally fused to another carbocyclic ring (e.g., a benzo ring, as when the substrate according to Formula I is 1,3-dihydroisobenzofuran, isochromane, or 1,2,3,4-tetrahydroquinoline). In some embodiments, $R^1$ and $R^2$ are taken together form piperidinyl or pyrrolidinyl, wherein the nitrogen atom is unsubstituted or substituted with $C_{1-6}$ alkyl, unsubstituted $C_{6-10}$ aryl, or substituted $C_{6-10}$ aryl. The aryl group can be substituted, for example, with one to five substituents independently selected from $C_{1-6}$ alkyl, $C_{1-6}$ alkoxy, $C_{1-6}$ haloalkyl, and halogen.

In some embodiments, the substrate having the sp$^3$-hybridized C—H bond is selected from the group consisting of:

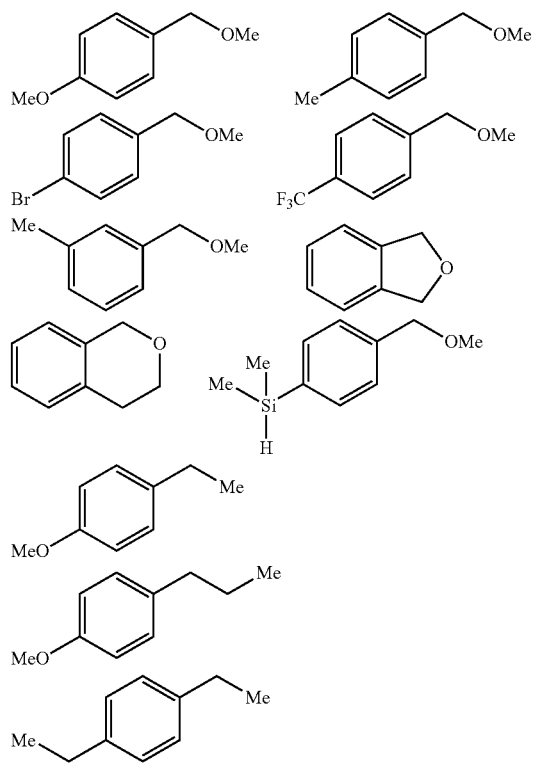

-continued

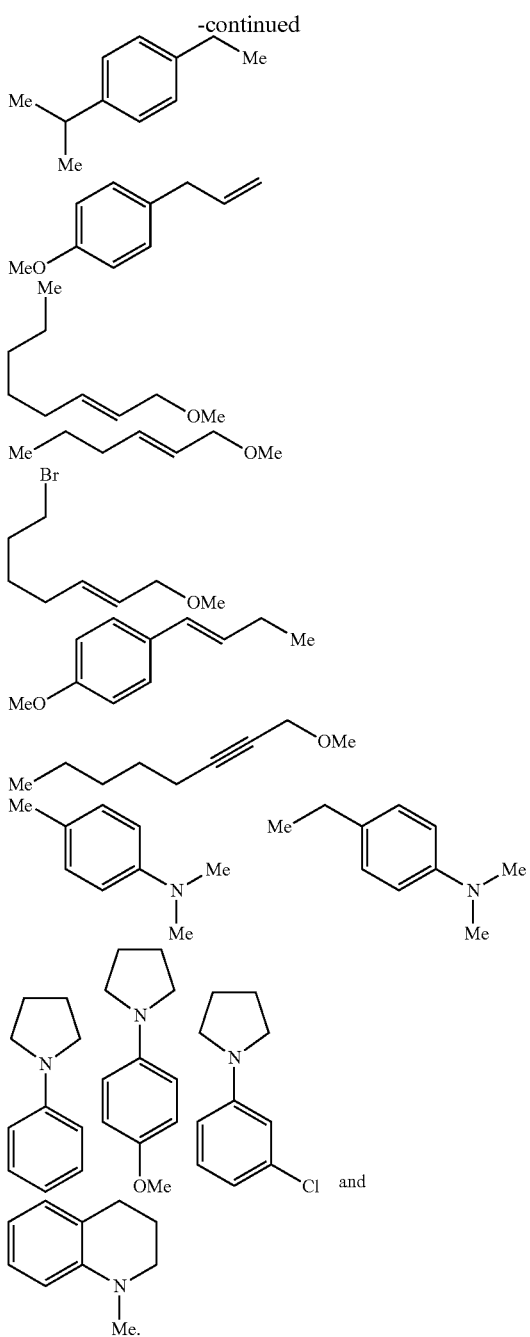

and 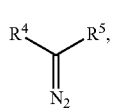

A number of carbene precursors can be used in the methods and reaction mixtures including, but not limited to, amines, azides, hydrazines, hydrazones, epoxides, diazirines, and diazo reagents. In some embodiments, the carbene precursor is an epoxide (i.e., a compound containing an epoxide moiety). The term "epoxide moiety" refers to a three-membered heterocycle having two carbon atoms and one oxygen atom connected by single bonds. In some embodiments, the carbene precursor is a diazirine (i.e., a compound containing a diazirine moiety). The term "diazirine moiety" refers to a three-membered heterocycle having one carbon atom and two nitrogen atoms, wherein the nitrogen atoms are connected via a double bond. Diazirines are chemically inert, small hydrophobic carbene precursors described, for example, in US 2009/0211893, by Turro (*J. Am. Chem. Soc.* 1987, 109, 2101-2107), and by Brunner (*J. Biol. Chem.* 1980, 255, 3313-3318), which are incorporated herein by reference in their entirety.

In some embodiments, the carbene precursor is a diazo reagent, e.g., an α-diazoester, an α-diazoamide, an α-diazonitrile, an α-diazoketone, an α-diazoaldehyde, or an α-diazosilane. Diazo reagents can be formed from a number of starting materials using procedures that are known to those of skill in the art. Ketones (including 1,3-diketones), esters (including β-ketones), acyl chlorides, and carboxylic acids can be converted to diazo reagents employing diazo transfer conditions with a suitable transfer reagent (e.g., aromatic and aliphatic sulfonyl azides, such as toluenesulfonyl azide, 4-carboxyphenylsulfonyl azide, 2-naphthalenesulfonyl azide, methylsulfonyl azide, and the like) and a suitable base (e.g., triethylamine, triisopropylamine, diazobicyclo[2.2.2]octane, 1,8-diazabicyclo[5.4.0]undec-7-ene, and the like) as described, for example, in U.S. Pat. No. 5,191,069 and by Davies (*J. Am. Chem. Soc.* 1993, 115, 9468-9479), which are incorporated herein by reference in their entirety. The preparation of diazo compounds from azide and hydrazone precursors is described, for example, in U.S. Pat. Nos. 8,350,014 and 8,530,212, which are incorporated herein by reference in their entirety. Alkylnitrite reagents (e.g., (3-methylbutyl)nitrite) can be used to convert α-aminoesters to the corresponding diazo compounds in non-aqueous media as described, for example, by Takamura (*Tetrahedron,* 1975, 31: 227), which is incorporated herein by reference in its entirety. Alternatively, a diazo compound can be formed from an aliphatic amine, an aniline or other arylamine, or a hydrazine using a nitrosating agent (e.g., sodium nitrite) and an acid (e.g., p-toluenesulfonic acid) as described, for example, by Zollinger (*Diazo Chemistry I and II*, VCH Weinheim, 1994) and in US 2005/0266579, which are incorporated herein by reference in their entirety.

In some embodiments, the C—H insertion reaction is an intermolecular reaction and the carbene precursor reagent has a structure according to Formula II:

$$\underset{N_2}{R^4 \diagup\!\!\!\!\diagdown R^5}, \qquad (II)$$

wherein:

R$^4$ is selected from the group consisting of H, —C(O)OR$^{4a}$, —C(O)R$^{4a}$, —C(O)N(R$^{4b}$)$_2$, —SO$_2$R$^{4a}$, —SO$_2$OR$^4$, —P(O)(OR$^{4a}$)$_2$, —NO$_2$, —CN, C$_{1-18}$ alkyl, C$_{2-18}$ alkenyl, C$_{2-18}$ alkynyl, 2- to 18-membered heteroalkyl, C$_{1-18}$ haloalkyl, C$_{1-18}$ alkoxy, C$_{3-10}$ cycloalkyl, C$_{6-10}$ aryl, 3- to 10-membered heterocyclyl, and 5- to 10-membered heteroaryl;

each R$^{4a}$ is independently selected from the group consisting of H, C$_{1-18}$ alkyl, C$_{2-18}$ alkenyl, C$_{2-18}$ alkynyl, C$_{6-10}$ aryl, 3- to 10-membered heterocyclyl, and 5- to 10-membered heteroaryl;

each R$^{4b}$ is independently selected from the group consisting of H, C$_{1-18}$ alkyl, C$_{2-18}$ alkenyl, C$_{-18}$ alkynyl, and C$_{1-18}$ alkoxy;

R$^5$ is an electron-withdrawing group selected from the group consisting of —C(O)OR$^{5a}$, —C(O)R$^{5a}$, —C(O)N(R$^{5b}$)$_2$, —SO$_2$R$^{5a}$, —SO$_2$OR$^{5a}$, —P(O)(OR$^{5a}$)$_2$, —NO$_2$, and —CN;

each $R^{5a}$ is independently selected from the group consisting of H, $C_{1-18}$ alkyl, $C_{2-18}$ alkenyl, $C_{2-18}$ alkynyl, $C_{6-10}$ aryl, 3- to 10-membered heterocyclyl, and 5- to 10-membered heteroaryl;

each $R^{5b}$ is independently selected from the group consisting of H, $C_{1-18}$ alkyl, $C_{2-18}$ alkenyl, $C_{2-18}$ alkynyl, and $C_{1-8}$ alkoxy; and $R^4$ and $R^5$ are optionally and independently substituted; or $R^4$ and $R^5$ are taken together to form $C_{3-10}$ cycloalkyl, $C_{6-10}$ aryl, 3- to 10-membered heterocyclyl, and 5- to 10-membered heteroaryl, each of which is optionally substituted.

In some embodiments, the carbene precursor reagent is a compound according to Formula II wherein:

$R^4$ is selected from the group consisting of H, —C(O)OR$^{4a}$, —C(O)R$^{4a}$, —C(O)N(R$^{4b}$)$_2$, —SO$_2$R$^{4a}$, —SO$_2$OR$^{4a}$, —P(O)(OR$^{4a}$)$_2$, —NO$_2$, —CN, $C_{1-18}$ alkyl, 2- to 18-membered heteroalkyl, $C_{1-18}$ haloalkyl, $C_{1-18}$ alkoxy, $C_{3-10}$ cycloalkyl, $C_{6-10}$ aryl, 3- to 10-membered heterocyclyl, and 5- to 10-membered heteroaryl;

each $R^{4a}$ is independently $C_{1-8}$ alkyl;

each $R^{4b}$ is independently selected from the group consisting of H, $C_{1-8}$ alkyl, and $C_{1-8}$ alkoxy;

$R^5$ is an electron-withdrawing group selected from the group consisting of —C(O)OR$^{5a}$, —C(O)R$^{5a}$, —C(O)N(R$^{5b}$)$_2$, —SO$_2$R$^{5a}$, —SO$_2$OR$^{5a}$, —P(O)(OR$^{5a}$)$_2$, —NO$_2$, and —CN;

each $R^{5a}$ is independently $C_{1-8}$ alkyl;

each $R^{5b}$ is independently selected from the group consisting of H, $C_{1-8}$ alkyl, and $C_{1-8}$ alkoxy; and $R^4$ and $R^5$ are optionally and independently substituted; or $R^4$ and $R^5$ are taken together to form $C_{3-10}$ cycloalkyl, $C_{6-10}$ aryl, 3- to 10-membered heterocyclyl, and 5- to 10-membered heteroaryl, each of which is optionally substituted.

In some embodiments:

$R^4$ is independently selected from the group consisting of H, —C(O)OR$^{4a}$, —C(O)R$^{4a}$, —SO$_2$R$^{4a}$, —SO$_2$OR$^{4a}$, substituted $C_{1-18}$ alkyl, 2- to 18-membered heteroalkyl, $C_{1-18}$ alkoxy, $C_{3-10}$ cycloalkyl, $C_{1-18}$ fluoroalkyl, substituted $C_{6-10}$ aryl, and substituted 5- to 10-membered heteroaryl;

$R^{4a}$ is $C_{1-8}$ alkyl;

$R^5$ is selected from the group consisting of —C(O)OR$^{5a}$, —C(O)R$^{5a}$, —SO$_2$R$^{5a}$, and —SO$_2$OR$^{5a}$; and $R^{5a}$ is $C_{1-8}$ alkyl; or $R^4$ and $R^5$ are optionally taken together to form $C_{3-10}$ cycloalkyl, $C_{6-10}$ aryl, 3- to 10-membered heterocyclyl, and 5- to 10-membered heteroaryl, each of which is optionally substituted.

In some embodiments, $R^5$ is —C(O)OR$^{5a}$ or —C(O)N(R$^{5b}$)$_2$. In some embodiments, $R^5$ is —C(O)OR$^{5a}$ and $R^{5a}$ is $C_{1-8}$ alkyl or $C_{1-8}$ alkyl substituted with $C_{6-10}$ aryl. $R^{5a}$ can be further substituted with one or more substituents (e.g., 1-6 substituents, or 1-3 substituents, or 1-2 substituents) independently selected from halogen, —OH, —NO$_2$; —CN; —N$_3$; $C_{1-6}$ alkyl, $C_{1-6}$ alkoxy, $C_{1-6}$ haloalkyl, $C_{1-18}$ alkylsilyl, unsubstituted $C_{6-10}$ aryl, and substituted $C_{6-10}$ aryl. In some embodiments, $R^5$ is —C(O)OR$^{5a}$ and $R^4$ is H, $C_{1-8}$ alkyl, $C_{1-18}$ alkoxy, $C_{3-10}$ cycloalkyl, or $C_{6-10}$ aryl. In some such embodiments, $R^4$ is H or $C_{1-8}$ alkyl.

In some embodiments, $R^5$ is —C(O)N(R$^{5b}$)$_2$ and each $R^{5b}$ is independently $C_{1-8}$ alkyl or $C_{1-8}$ alkoxy. In some such embodiments, $R^4$ is H, $C_{1-8}$ alkyl, $C_{1-18}$ alkoxy, $C_{3-10}$ cycloalkyl, or $C_{6-10}$ aryl. In some embodiments, $R^4$ is H or $C_{1-8}$ alkyl.

In some embodiments, $R^5$ and $R^4$ are taken together with the central carbon atom in Formula II to form $C_{3-10}$ cycloalkyl, $C_{6-10}$ aryl, 3- to 10-membered heterocyclyl, or 5- to 10-membered heteroaryl. In some embodiments, $R^5$ is C(O)OR$^{5a}$, —C(O)R$^{5a}$, or —C(O)N(R$^{5b}$)$_2$, wherein $R^{5a}$ or one $R^{5b}$ is taken together with $R^4$ to form $C_{3-10}$ cycloalkyl or 3- to 10-membered heterocyclyl. For example, $R^{5a}$ and $R^4$ can be taken together to form dihydrofuran-2(3H)-one when the carbene precursor according to Formula II is 3-diazodihydrofuran-2(3H)-one.

In some embodiments, the carbene precursor is selected from the group consisting of:

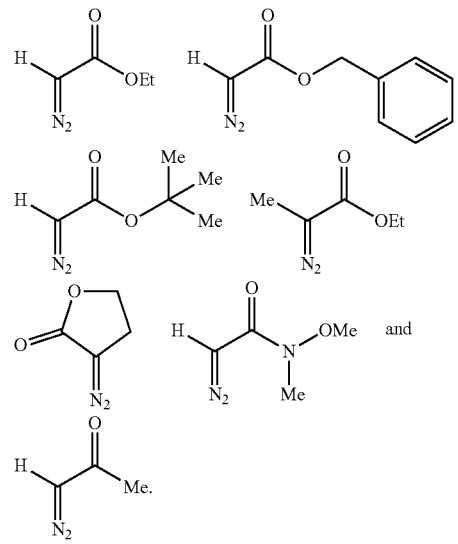

Reaction mixtures according to the present disclosure can also be employed for the preparation of C—H insertion products via intramolecular insertion reactions, i.e., reactions where the carbene precursor is present in the same compound as the substrate having the sp$^3$-hybridized C—H bond. In some such embodiments, the substrate having the sp$^3$-hybridized C—H bond is a compound according to Formula III:

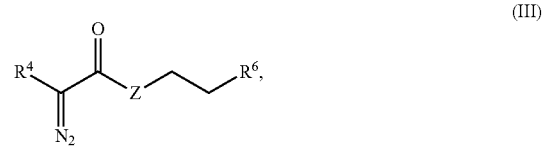

wherein:

Z is selected from the group consisting of C(R$^7$)$_2$, O, and NR$^7$;

$R^4$ is selected from the group consisting of H, —C(O)OR$^{4a}$, —C(O)R$^{4a}$, —C(O)N(R$^{4b}$)$_2$, —SO$_2$R$^{4a}$, —SO$_2$OR$^{4a}$, —P(O)(OR$^{4a}$)$_2$, —NO$_2$, —CN, $C_{1-18}$ alkyl, $C_{2-18}$ alkenyl, $C_{2-18}$ alkynyl, 2- to 18-membered heteroalkyl, $C_{1-18}$ haloalkyl, $C_{1-18}$ alkoxy, $C_{3-10}$ cycloalkyl, $C_{6-10}$ aryl, 3- to 10-membered heterocyclyl, and 5- to 10-membered heteroaryl, each of which is optionally substituted;

$R^6$ is selected from the group consisting of H, $C_{1-18}$ alkyl, $C_{2-18}$ alkenyl, $C_{2-18}$ alkynyl, 2- to 18-membered heteroalkyl, $C_{1-18}$ haloalkyl, $C_{1-18}$ alkoxy, $C_{3-10}$ cycloalkyl, $C_{6-10}$ aryl, 3- to 10-membered heterocyclyl, and 5- to 10-membered heteroaryl, each of which is optionally substituted;

each $R^7$ is independently selected from the group consisting of H and $C_{1-8}$ alkyl.

In some embodiments, the substrate is a compound according to Formula III wherein:

Z is selected from the group consisting of $C(R^7)_2$, O, and $NR^7$;

$R^4$ is selected from the group consisting of H, —C(O)$OR^{4a}$, —C(O)$R^{4a}$, —C(O)N($R^{4b})_2$, —SO$_2R^{4a}$, —SO$_2OR^{4a}$, —P(O)(OR$^{4a})_2$, —NO$_2$, —CN, $C_{1-18}$ alkyl, 2- to 18-membered heteroalkyl, $C_{1-18}$ haloalkyl, $C_{1-18}$ alkoxy, $C_{3-10}$ cycloalkyl, $C_{6-10}$ aryl, 3- to 10-membered heterocyclyl, and 5- to 10-membered heteroaryl;

$R^6$ is selected from the group consisting of H, $C_{1-18}$ alkyl, 2- to 18-membered heteroalkyl, $C_{1-18}$ haloalkyl, $C_{1-18}$ alkoxy, $C_{2-18}$ alkenyl, $C_{3-10}$ cycloalkyl, $C_{6-10}$ aryl, 3- to 10-membered heterocyclyl, and 5- to 10-membered heteroaryl, each of which is optionally substituted;

each $R^7$ is independently selected from the group consisting of H and $C_{1-8}$ alkyl.

In some embodiments, $R^6$ is selected from the group consisting of H, substituted $C_{1-18}$ alkyl, 2- to 18-membered heteroalkyl, $C_{1-18}$ alkoxy, $C_{3-10}$ cycloalkyl, substituted $C_{6-10}$ aryl, and substituted 5- to 10-membered heteroaryl. In some such embodiments, $R^4$ is H, $C_{1-8}$ alkyl, $C_{1-18}$ alkoxy, $C_{3-10}$ cycloalkyl, or $C_{6-10}$ aryl. In some embodiments, $R^4$ is H or $C_{1-8}$ alkyl.

In some embodiments, $R^6$ is $C_{6-10}$ aryl, $C_{1-8}$ alkyl substituted with $C_{6-10}$ aryl, or $C_{2-8}$ alkenyl substituted with $C_{6-10}$ aryl. In each instance, $C_{6-10}$ aryl can be substituted or unsubstituted. In some embodiments, $C_{6-10}$ aryl is substituted with one to five substituents independently selected from halogen, —OH, —NO$_2$; —CN; —N$_3$; $C_{1-6}$ alkyl, $C_{1-6}$ alkoxy, $C_{1-6}$ haloalkyl, and $C_{1-18}$ alkylsilyl. In some embodiments, $C_{6-10}$ aryl is substituted with one to 5 substituents independently selected from $C_{1-6}$ alkyl, $C_{1-6}$ alkoxy, $C_{1-6}$ haloalkyl, and $C_{1-18}$ alkylsilyl. In some embodiments, $R^6$ is phenyl, benzyl, or styryl, each of which is optionally substituted with one to five substituents on the aromatic ring. In some such embodiments, $R^4$ is H, $C_{1-8}$ alkyl, $C_{1-18}$ alkoxy, $C_{3-10}$ cycloalkyl, or $C_{6-10}$ aryl. In some embodiments, $R^4$ is H or $C_{1-8}$ alkyl.

In some embodiments, $R^6$ is $C_{1-8}$ alkyl, $C_{2-8}$ alkenyl, or $C_{2-8}$ alkynyl, each of which is optionally substituted with one or more substituents (e.g., 1-6 substituents, or 1-3 substituents, or 1-2 substituents) independently selected from halogen, —OH, —NO$_2$; —CN; —N$_3$; $C_{1-6}$ alkyl, $C_{1-6}$ alkoxy, $C_{1-6}$ haloalkyl, $C_{1-18}$ alkylsilyl, unsubstituted $C_{6-10}$ aryl, and substituted $C_{6-10}$ aryl. In some such embodiments, $R^2$ is $C_{1-8}$ alkyl or $C_{1-8}$ alkoxy. In some embodiments, $R^4$ is H, $C_{1-8}$ alkyl, $C_{1-18}$ alkoxy, $C_{3-10}$ cycloalkyl, or $C_{6-10}$ aryl. In some embodiments, $R^4$ is H or $C_{1-8}$ alkyl.

Compounds according to Formula I, Formula Ia, Formula II, and Formula III can be further substituted. Suitable monovalent substituents on a substitutable carbon atom of an "optionally substituted" group are independently halogen; —(CH$_2)_{0-4}R^{\alpha}$; —(CH$_2)_{0-4}OR^{\alpha}$; —O(CH$_2)_{0-4}R^{\alpha}$; —O—(CH$_2)_{0-4}C(O)OR^{\alpha}$; —(CH$_2)_{0-4}CH(OR^{\alpha})_2$; —(CH$_2)_{0-4}SR^{\alpha}$; —(CH$_2)_{0-4}$Ph, wherein Ph is phenyl which may be substituted with $R^{\alpha}$; —(CH$_2)_{0-4}O(CH_2)_{0-1}$phenyl, which phenyl is phenyl which may be substituted with $R^{\alpha}$; —CH=CHPh, wherein Ph is phenyl which may be substituted with $R^{\alpha}$; —(CH$_2)_{0-4}O(CH_2)_{0-1}$-Py, wherein Py is pyridyl which may be substituted with $R^{\alpha}$; —NO$_2$; —CN; —N$_3$; —(CH$_2)_{0-4}N(R^{\alpha})_2$; —(CH$_2)_{0-4}N(R^{\alpha})C(O)R^{\alpha}$; —N(R$^{\alpha})C(S)R^{\alpha}$; —(CH$_2)_{0-4}N(R^{\alpha})C(O)NR^{\alpha}_2$; —N(R$^{\alpha})C(S)NR^{\alpha}_2$; —(CH$_2)_{0-4}N(R^{\alpha})C(O)OR^{\alpha}$; —N(R$^{\alpha})N(R^{\alpha})C(O)R^{\alpha}$; —N(R$^{\alpha})N(R^{\alpha})C(O)NR^{\alpha}_2$; —N(R$^{\alpha})N(R^{\alpha})C(O)OR^{\alpha}$; —(CH$_2)_{0-4}C(O)R^{\alpha}$; —C(S)R$^{\alpha}$; —(CH$_2)_{0-4}C(O)OR^{\alpha}$; —(CH$_2)_{0-4}C(O)SR^{\alpha}$; —(CH$_2)_{0-4}C(O)OSiR^{\alpha}_3$; —(CH$_2)_{0-4}OC(O)R^{\alpha}$; —OC(O)(CH$_2)_{0-4}SR$—SC(S)SR$^{\alpha}$; —(CH$_2)_{0-4}SC(O)R^{\alpha}$; —(CH$_2)_{0-4}C(O)NR^{\alpha}_2$; —C(S)NR$^{\alpha}_2$; —C(S)SR$^{\alpha}$; —SC(S)SR$^{\alpha}$, —(CH$_2)_{0-4}OC(O)NR^{\alpha}_2$; —C(O)N(OR$^{\alpha})R^{\alpha}$; —C(O)C(O)R$^{\alpha}$; —C(O)CH$_2$C(O)R$^{\alpha}$; —C(NOR$^{\alpha})R^{\alpha}$; —(CH$_2)_{0-4}SSR^{\alpha}$; —(CH$_2)_{0-4}S(O)_2R^{\alpha}$; —(CH$_2)_{0-4}S(O)_2OR^{\alpha}$; —(CH$_2)_{0-4}OS(O)_2R^{\alpha}$; —S(O)$_2$NR$^{\alpha}_2$; —(CH$_2)_{0-4}S(O)R^{\alpha}$; —N(R$^{\alpha})S(O)_2NR^{\alpha}_2$; —N(R$^{\alpha})S(O)_2R^{\alpha}$; —N(OR$^{\alpha})R^{\alpha}$; —C(NH)NR$^{\alpha}_2$; —P(O)$_2R^{\alpha}$; —P(O)R$^{\alpha}_2$; —OP(O)R$^{\alpha}_2$; —OP(O)(OR$^{\alpha})_2$; SiR$^{\alpha}_3$; —(C$_{1-4}$ straight or branched)alkylene)-O—N(R$^{\alpha})_2$; or —(C$_{1-4}$ straight or branched)alkylene)-C(O)O—N(R$^{\alpha})_2$. Each $R^{\alpha}$ is independently hydrogen; $C_{1-6}$ alkyl; —CH$_2$Ph, —O(CH$_2)_{0-1}$Ph; —CH$_2$-(5- to 6-membered heteroaryl); $C_{3-8}$ cycloalkyl; $C_{6-10}$ aryl; 4- to 10-membered heterocyclyl; or 6- to 10-membered heteroaryl; and each $R^{\alpha}$ may be further substituted as described below.

Suitable monovalent substituents on $R^{\alpha}$ are independently halogen, —(CH$_2)_{0-2}R^{\beta}$; —(CH$_2)_{0-2}OH$; —(CH$_2)_{0-2}OR^{\beta}$; —(CH$_2)_{0-2}CH(OR^{\beta})_2$; —CN; —N$_3$; —(CH$_2)_{0-2}C(O)R^{\beta}$; —(CH$_2)_{0-2}C(O)OH$; —(CH$_2)_{0-2}C(O)OR^{\beta}$; —(CH$_2)_{0-2}SR^{\beta}$; —(CH$_2)_{0-2}SH$; —(CH$_2)_{0-2}NH_2$; —(CH$_2)_{0-2}NHR^{\beta}$; —(CH$_2)_{0-2}NR^{\beta}_2$; —NO$_2$; SiR$^{\beta}_3$; —OSiR$^{\beta}_3$; —C(O)SR$^{\beta}$; —(C$_{1-4}$ straight or branched alkylene)-C(O)OR$^{\beta}$; or —SSR$^{\beta}$; wherein each $R^{\beta}$ is independently selected from $C_{1-4}$ alkyl; —CH$_2$Ph; —O(CH$_2)_{0-1}$Ph; $C_{3-8}$ cycloalkyl; $C_{6-10}$ aryl; 4- to 10-membered heterocyclyl; or 6- to 10-membered heteroaryl. Suitable divalent substituents on a saturated carbon atom of $R^{\alpha}$ include =O and =S.

Suitable divalent substituents on a saturated carbon atom of an "optionally substituted" group include the following: =O; =S; =NNR$^{\gamma}_2$; =NNHC(O)R$^{\gamma}$; =NNHC(O)OR$^{\gamma}$; =NNHS(O)$_2R^{\gamma}$; =NR$^{\gamma}$; =NOR$^{\gamma}$; —O(C(R$^{\gamma}_2))_{2-3}$O—; or —S(C(R$^{\gamma}_2))_{2-3}$S—; wherein each independent occurrence of $R^{\gamma}$ is selected from hydrogen; $C_{1-6}$ alkyl, which may be substituted as defined below; $C_{3-8}$ cycloalkyl; $C_{6-10}$ aryl; 4- to 10-membered heterocyclyl; or 6- to 10-membered heteroaryl. Suitable divalent substituents that are bound to vicinal substitutable carbons of an "optionally substituted" group include: —O(CR$^{\beta}_2)_{2-3}$O—; wherein each independent occurrence of $R^{\beta}$ is selected from hydrogen; $C_{1-6}$ alkyl which may be substituted as defined below; $C_{3-8}$ cycloalkyl; $C_{6-10}$ aryl; 4- to 10-membered heterocyclyl; or 6- to 10-membered heteroaryl.

Suitable substituents on the alkyl group of $R^{\gamma}$ include halogen; —R$^{\delta}$; —OH; —OR$^{\delta}$; —CN; —C(O)OH; —C(O)OR$^{\delta}$; —NH$_2$; —NHR$^{\delta}$; —NR$^{\delta}_2$; or —NO$_2$; wherein each $R^{\delta}$ is independently $C_{1-4}$ alkyl; —CH$_2$Ph; —O(CH$_2)_{0-1}$Ph; 4- to 10-membered heterocyclyl; or 6- to 10-membered heteroaryl.

Suitable substituents on a substitutable nitrogen of an "optionally substituted" group include —R$^{\varepsilon}$; —NR$^{\varepsilon}_2$; —C(O)R$^{\varepsilon}$; —C(O)OR$^{\varepsilon}$; —C(O)C(O)R$^{\varepsilon}$; —C(O)CH$_2$C(O)R$^{\varepsilon}$; —S(O)$_2R^{\varepsilon}$; —S(O)$_2NR^{\varepsilon}_2$; —C(S)NR$^{\varepsilon}_2$; —C(NH)NR$^{\varepsilon}_2$; or —N(R$^{\varepsilon})S(O)_2R^{\varepsilon}$; wherein each $R^{\varepsilon}$ is independently hydrogen; $C_{1-6}$ alkyl which may be substituted as defined below; $C_{3-8}$ cycloalkyl; $C_{6-10}$ aryl; 4- to 10-membered heterocyclyl; or 6- to 10-membered heteroaryl.

Suitable substituents on the alkyl group of $R^{\varepsilon}$ are independently halogen; —R$^{\delta}$; —OH; —OR$^{\delta}$; —CN; —C(O)OH; —C(O)OR$^{\delta}$; —NH$_2$; —NHR$^{\delta}$; —NR$^{\delta}_2$; or —NO$_2$; wherein each $R^{\delta}$ is independently $C_{1-4}$ alkyl; —CH$_2$Ph;

—O(CH$_2$)$_{0-1}$Ph; C$_{6-10}$ aryl; 4- to 10-membered heterocyclyl; or 6- to 10-membered heteroaryl.

A. Heme Proteins

Reaction mixtures according to the present disclosure also contain a heme protein. The terms "heme protein" and "heme enzyme" are used herein to include any member of a group of proteins containing heme as a prosthetic group. Non-limiting examples of heme proteins include globins, cytochromes, oxidoreductases, any other protein containing a heme as a prosthetic group, and combinations thereof. Heme-containing globins include, but are not limited to, hemoglobin, myoglobin, and combinations thereof. Heme-containing cytochromes include, but are not limited to, cytochrome P450, cytochrome b, cytochrome c1, cytochrome c, and combinations thereof. Heme-containing oxidoreductases include, but are not limited to, catalases, oxidases, oxygenases, haloperoxidases, peroxidases, and combinations thereof. In some embodiments, for example, the cytochrome P450 protein is P450$_{BM3}$ (CYP102A1).

In some embodiments, the heme protein is a member of one of the enzyme classes set forth in Table 1. In other embodiments, the heme protein is a variant or homolog of a member of one of the enzyme classes set forth in Table 1. In yet other embodiments, the heme protein comprises or consists of the heme domain of a member of one of the enzyme classes set forth in Table 1 or a fragment thereof (e.g., a truncated heme domain) that is capable of carrying out the C—H insertion reactions described herein.

TABLE 1

Heme enzymes for use according to the present disclosure.

| EC Number | Name |
|---|---|
| 1.1.2.3 | L-lactate dehydrogenase |
| 1.1.2.6 | polyvinyl alcohol dehydrogenase (cytochrome) |
| 1.1.2.7 | methanol dehydrogenase (cytochrome c) |
| 1.1.5.5 | alcohol dehydrogenase (quinone) |
| 1.1.5.6 | formate dehydrogenase-N: |
| 1.1.9.1 | alcohol dehydrogenase (azurin): |
| 1.1.99.3 | gluconate 2-dehydrogenase (acceptor) |
| 1.1.99.11 | fructose 5-dehydrogenase |
| 1.1.99.18 | cellobiose dehydrogenase (acceptor) |
| 1.1.99.20 | alkan-1-ol dehydrogenase (acceptor) |
| 1.2.1.70 | glutamyl-tRNA reductase |
| 1.2.3.7 | indole-3-acetaldehyde oxidase |
| 1.2.99.3 | aldehyde dehydrogenase (pyrroloquinoline-quinone) |
| 1.3.1.6 | fumarate reductase (NADH) |
| 1.3.5.1 | succinate dehydrogenase (ubiquinone) |
| 1.3.5.4 | fumarate reductase (menaquinone) |
| 1.3.99.1 | succinate dehydrogenase |
| 1.4.9.1 | methylamine dehydrogenase (amicyanin) |
| 1.4.9.2. | aralkylamine dehydrogenase (azurin) |
| 1.5.1.20 | methylenetetrahydrofolate reductase [NAD(P)H] |
| 1.5.99.6 | spermidine dehydrogenase |
| 1.6.3.1 | NAD(P)H oxidase |
| 1.7.1.1 | nitrate reductase (NADH) |
| 1.7.1.2 | Nitrate reductase [NAD(P)H] |
| 1.7.1.3 | nitrate reductase (NADPH) |
| 1.7.1.4 | nitrite reductase [NAD(P)H] |
| 1.7.1.14 | nitric oxide reductase [NAD(P), nitrous oxide-forming] |
| 1.7.2.1 | nitrite reductase (NO-forming) |
| 1.7.2.2 | nitrite reductase (cytochrome; ammonia-forming) |
| 1.7.2.3 | trimethylamine-N-oxide reductase (cytochrome c) |
| 1.7.2.5 | nitric oxide reductase (cytochrome c) |
| 1.7.2.6 | hydroxylamine dehydrogenase |
| 1.7.3.6 | hydroxylamine oxidase (cytochrome) |
| 1.7.5.1 | nitrate reductase (quinone) |
| 1.7.5.2 | nitric oxide reductase (menaquinol) |
| 1.7.6.1 | nitrite dismutase |
| 1.7.7.1 | ferredoxin-nitrite reductase |
| 1.7.7.2 | ferredoxin-nitrate reductase |
| 1.7.99.4 | nitrate reductase |
| 1.7.99.8 | hydrazine oxidoreductase |

TABLE 1-continued

Heme enzymes for use according to the present disclosure.

| EC Number | Name |
|---|---|
| 1.8.1.2 | sulfite reductase (NADPH) |
| 1.8.2.1 | sulfite dehydrogenase |
| 1.8.2.2 | thiosulfate dehydrogenase |
| 1.8.2.3 | sulfide-cytochrome-c reductase (flavocytochrome c) |
| 1.8.2.4 | dimethyl sulfide:cytochrome c2 reductase |
| 1.8.3.1 | sulfite oxidase |
| 1.8.7.1 | sulfite reductase (ferredoxin) |
| 1.8.98.1 | CoB-CoM heterodisulfide reductase |
| 1.8.99.1 | sulfite reductase |
| 1.8.99.2 | adenylyl-sulfate reductase |
| 1.8.99.3 | hydrogensulfite reductase |
| 1.9.3.1 | cytochrome-c oxidase |
| 1.9.6.1 | nitrate reductase (cytochrome) |
| 1.10.2.2 | ubiquinol-cytochrome-c reductase |
| 1.10.3.1 | catechol oxidase |
| 1.10.3.B1 | caldariellaquinol oxidase (H+-transporting) |
| 1.10.3.3 | L-ascorbate oxidase |
| 1.10.3.9 | photosystem II |
| 1.10.3.10 | ubiquinol oxidase (H+-transporting) |
| 1.10.3.11 | ubiquinol oxidase |
| 1.10.3.12 | menaquinol oxidase (H+-transporting) |
| 1.10.9.1 | plastoquinol-plastocyanin reductase |
| 1.11.1.5 | cytochrome-c peroxidase |
| 1.11.1.6 | Catalase |
| 1.11.1.7 | Peroxidase |
| 1.11.1.B2 | chloride peroxidase (vanadium-containing) |
| 1.11.1.B7 | bromide peroxidase (heme-containing) |
| 1.11.1.8 | iodide peroxidase |
| 1.11.1.10 | chloride peroxidase |
| 1.11.1.11 | L-ascorbate peroxidase |
| 1.11.1.13 | manganese peroxidase |
| 1.11.1.14 | lignin peroxidase |
| 1.11.1.16 | versatile peroxidase |
| 1.11.1.19 | dye decolorizing peroxidase |
| 1.11.1.21 | catalase-peroxidase |
| 1.11.2.1 | unspecific peroxygenase |
| 1.11.2.2 | Myeloperoxidase |
| 1.11.2.3 | plant seed peroxygenase |
| 1.11.2.4 | fatty-acid peroxygenase |
| 1.12.2.1 | cytochrome-c3 hydrogenase |
| 1.12.5.1 | hydrogen:quinone oxidoreductase |
| 1.12.99.6 | hydrogenase (acceptor) |
| 1.13.11.9 | 2,5-dihydroxypyridine 5,6-dioxygenase |
| 1.13.11.11 | tryptophan 2,3-dioxygenase |
| 1.13.11.49 | chlorite O2-lyase |
| 1.13.11.50 | acetylacetone-cleaving enzyme |
| 1.13.11.52 | indoleamine 2,3-dioxygenase |
| 1.13.11.60 | linoleate 8R-lipoxygenase |
| 1.13.99.3 | tryptophan 2'-dioxygenase |
| 1.14.11.9 | flavanone 3-dioxygenase |
| 1.14.12.17 | nitric oxide dioxygenase |
| 1.14.13.39 | nitric-oxide synthase (NADPH dependent) |
| 1.14.13.17 | cholesterol 7alpha-monooxygenase |
| 1.14.13.41 | tyrosine N-monooxygenase |
| 1.14.13.70 | sterol 14alpha-demethylase |
| 1.14.13.71 | N-methylcoclaurine 3'-monooxygenase |
| 1.14.13.81 | magnesium-protoporphyrin IX monomethyl ester (oxidative) cyclase |
| 1.14.13.86 | 2-hydroxyisoflavanone synthase |
| 1.14.13.98 | cholesterol 24-hydroxylase |
| 1.14.13.119 | 5-epiaristolochene 1,3-dihydroxylase |
| 1.14.13.126 | vitamin D3 24-hydroxylase |
| 1.14.13.129 | beta-carotene 3-hydroxylase |
| 1.14.13.141 | cholest-4-en-3-one 26-monooxygenase |
| 1.14.13.142 | 3-ketosteroid 9alpha-monooxygenase |
| 1.14.13.151 | linalool 8-monooxygenase |
| 1.14.13.156 | 1,8-cineole 2-endo-monooxygenase |
| 1.14.13.159 | vitamin D 25-hydroxylase |
| 1.14.14.1 | unspecific monooxygenase |
| 1.14.15.1 | camphor 5-monooxygenase |
| 1.14.15.6 | cholesterol monooxygenase (side-chain-cleaving) |
| 1.14.15.8 | steroid 15beta-monooxygenase |
| 1.14.15.9 | spheroidene monooxygenase |
| 1.14.18.1 | Tyrosinase |
| 1.14.19.1 | stearoyl-CoA 9-desaturase |
| 1.14.19.3 | linoleoyl-CoA desaturase |

TABLE 1-continued

Heme enzymes for use according to the present disclosure.

| EC Number | Name |
| --- | --- |
| 1.14.21.7 | biflaviolin synthase |
| 1.14.99.1 | prostaglandin-endoperoxide synthase |
| 1.14.99.3 | heme oxygenase |
| 1.14.99.9 | steroid 17alpha-monooxygenase |
| 1.14.99.10 | steroid 21-monooxygenase |
| 1.14.99.15 | 4-methoxybenzoate monooxygenase (O-demethylating) |
| 1.14.99.45 | carotene epsilon-monooxygenase |
| 1.16.5.1 | ascorbate ferrireductase (transmembrane) |
| 1.16.9.1 | iron:rusticyanin reductase |
| 1.17.1.4 | xanthine dehydrogenase |
| 1.17.2.2 | lupanine 17-hydroxylase (cytochrome c) |
| 1.17.99.1 | 4-methylphenol dehydrogenase (hydroxylating) |
| 1.17.99.2 | ethylbenzene hydroxylase |
| 1.97.1.1 | chlorate reductase |
| 1.97.1.9 | selenate reductase |
| 2.7.7.65 | diguanylate cyclase |
| 2.7.13.3 | histidine kinase |
| 3.1.4.52 | cyclic-guanylate-specific phosphodiesterase |
| 4.2.1.B9 | colneleic acid/etheroleic acid synthase |
| 4.2.1.22 | Cystathionine beta-synthase |
| 4.2.1.92 | hydroperoxide dehydratase |
| 4.2.1.212 | colneleate synthase |
| 4.3.1.26 | chromopyrrolate synthase |
| 4.6.1.2 | guanylate cyclase |
| 4.99.1.3 | sirohydrochlorin cobaltochelatase |
| 4.99.1.5 | aliphatic aldoxime dehydratase |
| 4.99.1.7 | phenylacetaldoxime dehydratase |
| 5.3.99.3 | prostaglandin-E synthase |
| 5.3.99.4 | prostaglandin-I synthase |
| 5.3.99.5 | Thromboxane-A synthase |
| 5.4.4.5 | 9,12-octadecadienoate 8-hydroperoxide 8R-isomerase |
| 5.4.4.6 | 9,12-octadecadienoate 8-hydroperoxide 8S-isomerase |
| 6.6.1.2 | Cobaltochelatase |

Some embodiments of the present disclosure provide a reaction mixture as described above, wherein the heme protein is a variant of a naturally occurring heme protein comprising a mutation at the axial position of the heme coordination site. In some embodiments, the heme protein comprises a serine mutation at the axial position of the heme coordination site.

A conserved residue in a heme protein of interest that serves as an heme axial ligand may be identified by locating the segment of the DNA sequence in the corresponding gene which encodes the conserved residue. In some instances, this DNA segment is identified through detailed mutagenesis studies in a conserved region of the protein. In other instances, the conserved residue is identified through crystallographic study.

In situations where detailed mutagenesis studies and crystallographic data are not available for a heme protein of interest, the axial ligand may be identified through phylogenetic study. Due to the similarities in amino acid sequence within families of heme proteins, standard protein alignment algorithms may show a phylogenetic similarity between a heme protein for which crystallographic or mutagenesis data exist and a new heme protein for which such data do not exist. Thus, the polypeptide sequences for which the heme axial ligand is known can be used as a "query sequence" to perform a search against a specific new heme protein of interest or a database comprising heme protein sequences to identify the heme axial ligand. Such analyses can be performed using the BLAST programs (see, e.g., Altschul et al., J Mol Biol. 215(3):403-10(1990)). Software for performing BLAST analyses publicly available through the National Center for Biotechnology Information. BLASTP is used for amino acid sequences.

Exemplary parameters for performing amino acid sequence alignments to identify the heme axial ligand in a heme protein of interest using the BLASTP algorithm include E value=10, word size=3, Matrix=Blosum62, Gap opening=11, gap extension=1, and conditional compositional score matrix adjustment. Those skilled in the art will know what modifications can be made to the above parameters, e.g., to either increase or decrease the stringency of the comparison and/or to determine the relatedness of two or more sequences.

Cytochrome P450 enzymes constitute a large superfamily of heme-thiolate proteins involved in the metabolism of a wide variety of both exogenous and endogenous compounds. Usually, they act as the terminal oxidase in multi-component electron transfer chains, such as P450-containing monooxygenase systems. Members of the cytochrome P450 enzyme family catalyze myriad oxidative transformations, including, e.g., hydroxylation, epoxidation, oxidative ring coupling, heteroatom release, and heteroatom oxygenation (E. M. Isin et al., $Biochim.$ $Biophys.$ $Acta$ 1770, 314 (2007)). P450s typically contain a single polypeptide, ranging from 40 to 55 kDa in molecular weight, and the same general fold has been observed in all P450s with known structures (T. L. Poulous, $Chem$ $Rev.,$ 114, 3919 (2014)). Conserved secondary structures included in the so-called "CYP fold" are commonly referred to as $\alpha$A-L and $\beta$1-5. The active site of these enzymes contains an $Fe^{III}$-protoporphyrin IX cofactor (heme) ligated proximally by a conserved cysteine thiolate (M. T. Green, $Current$ $Opinion$ $in$ $Chemical$ $Biology$ 13, 84 (2009)). The remaining axial iron coordination site is occupied by a water molecule in the resting enzyme, but during native catalysis, this site is capable of binding molecular oxygen. P450 structure is also typically characterized by a long "I helix" (typically around 50 angstroms in length) which runs over the surfaces of the heme and interacts with oxygen and the oxidation substrate. In the presence of an electron source, typically provided by NADH or NADPH from an adjacent fused reductase domain or an accessory cytochrome P450 reductase enzyme, the heme center of cytochrome P450 activates molecular oxygen, generating a high valent iron(IV)-oxo porphyrin cation radical species intermediate and a molecule of water.

Cytochrome $P450_{BM3}$ (CYP102A1) is found in the soil bacterium $Bacillus$ $megaterium$ and catalyzes the NADPH-dependent hydroxylation of long-chain fatty acids at the $\omega$-1 through $\omega$-3 positions. Unlike most other cytochrome P450 proteins, $P450_{BM3}$ is a natural fusion between the cytochrome P450 domain and an electron donating cofactor. Thus, $P450_{BM3}$ and variants thereof are useful in a number of biotechnological applications.

In some embodiments, the heme protein in the reaction mixture is a cytochrome P450 enzyme or a variant thereof. In some embodiments, the cytochrome P450 is a CYP102A sub-family P450. Examples of CYP102A cytochromes P450 include, but are not limited to, $P450_{BM3}$ (GenBank Accession No. J04832.1); CYP102A2 from $B.$ $subtilis$ (GenBank Accession No. D87979.1); CYP102A3 from $B.$ $subtilis$ (GenBank Accession No. U93874.1); CYP102A4 from $B.$ $anthracis$ str. Ames (GenBank Accession No. AAP27014.1); CYP102A5 from $B.$ $cereus$ ATCC 14579 (GenBank Accession No. AAP10153.1); CYP102A6 from $Bradyrhizobium$ $japonicum$ USDA 110 (GenBank Accession No. BAC48147.1); CYP102A7 from $B.$ $licheniformis$ ATCC 14580 (GenBank Accession No. AAU24352.1); CYP102A8 from $B.$ $thuringiensis$ serovar konkukian str. 97-27 (GenBank Accession No. AAT62301.1); CYP102A9 from $B.$ $weihenstephanensis$ KBAB4 (NCBI Reference Sequence No. ZP_01184381); CYP102A10 from *Erythrobacter litoralis* HTCC2594 (NCBI Reference Sequence No. WP_011412990.1); CYP102A11 from *Erythrobacter* sp. NAP1 (NBCI Reference Sequence No. ZP_01041731,1); CYP102A12 from *Rhodopseudomonas palustris* HaA2 (NCBI Reference Sequence No. WP_011442524.1); CYP102A13 from *Rhodopseudomonas palustris* HaA2 (NCBI Reference Sequence No. WP_011502240.1); CYP102A14 from an uncultured soil *bacterium* (GenBank Accession No. ABD83817.1); and CYP102A15 from *B. pumilus* ATCC 7061 (NCBI Reference Sequence No. ZP_03053227.1). In some embodiments, the cytochrome P450 is not a CYP119 P450.

In some embodiments, the cytochrome P450 is $P450_{BM3}$ or a variant thereof. In some embodiments, the $P450_{BM3}$ variant is a truncated variant comprising residues corresponding to residues 1-664 as determined with reference to SEQ ID NO:1. Surprisingly, truncated variants containing as few as around 40% of the amino acids in the full-length proteins, or less, were found to provide higher C—H insertion activity in certain instances. It is believed that the presence of the FAD domain in full-length constructs may have allosteric effects on C—H alkylation activity.

In some embodiments, the P450 polypeptide contains one or more mutations at amino acids lying with 15 Å from the iron atom in the heme cofactor of the P450. Examples of such residues in $P450_{BM3}$, for example, include but are not limited to N70, A74, A78, M177, F263, H266, A330, T436, and S438. In some embodiments, the mutation is present at a residue which lines the distal heme pocket and lies within 15 Å from the iron atom in the heme cofactor.

In some embodiments, the P450 polypeptide contains one or more mutations at positions corresponding to residues N70, A74, V78, A82, F87, M118, P142, F162, T175, M177, A184, S226, H236, E252, I263, H266, T268, A290, T327, A328, A330, L353, I366, C400, I401, T436, L437, T438, E442 as determined with reference to SEQ ID NO.1.

In some embodiments, the P450 polypeptide contains one or more mutations (e.g., 1-17 mutations, 1-15 mutations, 1-10 mutations, or 1-5 mutations) in a first grouping of residues at positions V78, A82, F87, P142, T175, A184, S226, H236, E252, I263, T268, A290, A328, L353, I366, C400, and E442, as determined with reference to SEQ ID NO:1. In some embodiments, the mutations in the first grouping of residues are V78A, A82L, F87A, P142S, T175I, A184V, S226R, H236Q, E252G, I263F, T268G, A290V, A328V, L353V, I366V, C400S, and E442K, as determined with reference to SEQ ID NO:1. In some embodiments, the P450 polypeptide further contains a mutation at position T438, as determined with reference to SEQ ID NO:1 (e.g., a T438S mutation).

In some embodiments, the P450 polypeptide contains mutations in the first grouping of residues and further contains one or more mutations (e.g., 1-5 mutations, 1-4 mutations, 1-3 mutations, or 1-2 mutations) in a second grouping of residues at positions A74, A78, A82, F263, and T327, and as determined with reference to SEQ ID NO:1. In some embodiments the mutations at the second grouping of residues are A74G, A78L, A82L, F263Y, and T327I. In some embodiments, the P450 polypeptide contains mutations in the first grouping of residues and further contains five mutations in the second grouping of residues. In some embodiments, the P450 polypeptide further contains a mutation at position L437, as determined with reference to SEQ ID NO:1 (e.g., an L437Q mutation).

In some embodiments, the P450 polypeptide contains the mutations in the first grouping of residues, one or more (e.g., 1, 2, 3, 4, or 5) mutations in the second grouping of residues, and one or more mutations (e.g., 1-7 mutations, 1-6 mutations, 1-5 mutations, 1-4 mutations, 1-3 mutations, or 1-2 mutations) in a third grouping of residues at positions N70, G74, M177, H266, I327, A330, and T436. In some embodiments, the mutations in the third grouping of residues are N70E, G74P, M177L, H266V, I327T, A330Y, and T436L. In some embodiments, the P450 polypeptide comprises the mutations in the first grouping of residues, five mutations in the second grouping of residues, and seven mutations in the third grouping of residues.

In some embodiments, the P450 polypeptide contains mutations A74G, V78L, A82L, F87A, P142S, T175I, A184V, S226R, H236Q, E252G, I263Y, T268G, A290V, T327I, A328V, L353V, I366V, C400S, T438S, and E442K as determined with reference to SEQ ID NO: 1.

In some embodiments, the P450 polypeptide contains mutations N70E, A74G, V78L, A82L, F87A, M118S, P142S, F162L, T175I, M177L, A184V, S226R, H236Q, E252G, I263Y, H266V, T268G, A290V, T327I, A328V, A330Y, L353V, I366V, C400S, I401L, T436L, L437Q, and E442K as determined with reference to SEQ ID NO:1.

In some embodiments, the P450 polypeptide contains mutations N70E, A74P, V78L, A82L, F87A, P142S, T175I, M177L, A184V, S226R, H236Q, E252G, I263Y, H266V, T268G, A290V, A328V, A330Y, L353V, I366V, C400S, T436L, and E442K as determined with reference to SEQ ID NO:1.

Mutations can be introduced at other positions in an enzyme such as $P450_{BM3}$ and the effect of the mutation on the CH insertion activity of the enzyme variant relative to the cytochrome P450 polypeptide without the amino acid mutations can be assessed using the methods described herein (e.g., by using HPLC or gas chromatography to monitor product formation in a reaction with a substrate such as 1-ethyl-4-methoxybenzene and carbene precursor such as ethyl diazoacetate). The engineering steps described above can be applied to other enzymes in the cytochrome P450 superfamily, which have been compiled in various databases, including, but not limited to, the P450 homepage see, e.g., D. R. Nelson, *Hum. Genomics* 4, 59 (2009)), the cytochrome P450 enzyme engineering database see, e.g., D. Sirim et al., *BMC Biochem* 10, 27 (2009)), and the SuperCyp database see, e.g., S. Preissner et al., *Nucleic Acids Res.* 38, D237 (2010)), the disclosures of which are incorporated herein by reference in their entirety for all purposes.

In certain embodiments, the cytochrome P450 enzymes are members of one of the classes shown in Table 2.

TABLE 2

Cytochrome P450 enzymes classified by their EC number, recommended name, and family/gene name.

| EC | Recommended name | Family/gene |
|---|---|---|
| 1.3.3.9 | secologanin synthase | CYP72A1 |
| 1.14.13.11 | trans-cinnamate 4-monooxygenase | CYP73 |
| 1.14.13.12 | benzoate 4-monooxygenase | CYP53 |
| 1.14.13.13 | calcidiol 1-monooxygenase | CYP27 |
| 1.14.13.15 | cholestanetriol 26-monooxygenase | CYP27 |
| 1.14.13.17 | cholesterol 7α-monooxygenase | CYP7 |
| 1.14.13.21 | flavonoid 3'-monooxygenase | CYP75 |
| 1.14.13.28 | 3,9-dihydroxypterocarpan 6a-monooxygenase | CYP93A1 |
| 1.14.13.30 | leukotriene-$B_4$ 20-monooxygenase | CYP4F |
| 1.14.13.37 | methyltetrahydroprotoberberine 14-monooxygenase | CYP93A1 |
| 1.14.13.41 | tyrosine N-monooxygenase | CYP79 |
| 1.14.13.42 | hydroxyphenylacetonitrile 2-monooxygenase | — |
| 1.14.13.47 | (−)-limonene 3-monooxygenase | — |

TABLE 2-continued

Cytochrome P450 enzymes classified by their EC number, recommended name, and family/gene name.

| EC | Recommended name | Family/gene |
|---|---|---|
| 1.14.13.48 | (−)-limonene 6-monooxygenase | — |
| 1.14.13.49 | (−)-limonene 7-monooxygenase | — |
| 1.14.13.52 | isoflavone 3'-hydroxylase | — |
| 1.14.13.53 | isoflavone 2'-hydroxylase | — |
| 1.14.13.55 | protopine 6-monooxygenase | — |
| 1.14.13.56 | dihydrosanguinarine 10-monooxygenase | — |
| 1.14.13.57 | dihydrochelirubine 12-monooxygenase | — |
| 1.14.13.60 | 27-hydroxycholesterol 7α-monooxygenase | — |
| 1.14.13.70 | sterol 14-demethylase | CYP51 |
| 1.14.13.71 | N-methylcoclaurine 3'-monooxygenase | CYP80B1 |
| 1.14.13.73 | tabersonine 16-hydroxylase | CYP71D12 |
| 1.14.13.74 | 7-deoxyloganin 7-hydroxylase | — |
| 1.14.13.75 | vinorine hydroxylase | — |
| 1.14.13.76 | taxane 10β-hydroxylase | CYP725A1 |
| 1.14.13.77 | taxane 13α-hydroxylase | CYP725A2 |
| 1.14.13.78 | ent-kaurene oxidase | CYP701 |
| 1.14.13.79 | ent-kaurenoic acid oxidase | CYP88A |
| 1.14.14.1 | unspecific monooxygenase | multiple |
| 1.14.15.1 | camphor 5-monooxygenase | CYP101 |
| 1.14.15.3 | alkane 1-monooxygenase | CYP4A |
| 1.14.15.4 | steroid 11β-monooxygenase | CYP11B |
| 1.14.15.5 | corticosterone 18-monooxygenase | CYP11B |
| 1.14.15.6 | cholesterol monooxygenase (side-chain-cleaving) | CYP11A |
| 1.14.21.1 | (S)-stylopine synthase | — |
| 1.14.21.2 | (S)-cheilanthifoline synthase | — |
| 1.14.21.3 | berbamunine synthase | CYP80 |
| 1.14.21.4 | salutaridine synthase | — |
| 1.14.21.5 | (S)-canadine synthase | — |
| 1.14.99.9 | steroid 17α-monooxygenase | CYP17 |
| 1.14.99.10 | steroid 21-monooxygenase | CYP21 |
| 1.14.99.22 | ecdysone 20-monooxygenase | — |
| 1.14.99.28 | linalool 8-monooxygenase | CYP111 |
| 4.2.1.92 | hydroperoxide dehydratase | CYP74 |
| 5.3.99.4 | prostaglandin-I synthase | CYP8 |
| 5.3.99.5 | thromboxane-A synthase | CYP5 |

Table 3 below lists additional cytochrome P450 enzymes that are suitable for use in the reaction mixtures and methods provided herein. The accession numbers in Table 3 are incorporated herein by reference in their entirety for all purposes. The cytochrome P450 gene and/or protein sequences disclosed in the following patent documents are hereby incorporated by reference in their entirety for all purposes: WO 2013/076258; CN 103160521; CN 103223219; KR 2013081394; JP 5222410; WO 2013/073775; WO 2013/054890; WO 2013/048898; WO 2013/031975; WO 2013/064411; US 8361769; WO 2012/150326; CN 102747053; CN 102747052; JP 2012170409; WO 2013/115484; CN 103223219; KR 2013081394; CN 103194461; JP 5222410; WO 2013/086499; WO 2013/076258; WO 2013/073775; WO 2013/064411; WO 2013/054890; WO 2013/031975; U.S. Pat. No. 8,361,769; WO 2012/156976; WO 2012/150326; CN 102747053; CN 102747052; US 20120258938; JP 2012170409; CN 102399796; JP 2012055274; WO 2012/029914; WO 2012/028709; WO 2011/154523; JP 2011234631; WO 2011/121456; EP 2366782; WO 2011/105241; CN 102154234; WO 2011/093185; WO 2011/093187; WO 2011/093186; DE 102010000168; CN 102115757; CN 102093984; CN 102080069; JP 2011103864; WO 2011/042143; WO 2011/038313; JP 2011055721; WO 2011/025203; JP 2011024534; WO 2011/008231; WO 2011/008232; WO 2011/005786; IN 2009DE01216; DE 102009025996; WO 2010/134096; WO 2010233523; JP 2010220609; WO 2010/095721; WO 2010/064764; US 20100136595; JP 2010051174; WO 2010/024437; WO 2010/011882; WO 2009/108388; US 20090209010; US 20090124515; WO 2009/041470; KR 2009028942; WO 2009/039487; WO 2009/020231; JP 2009005687; CN 101333520; CN 101333521; US 20080248545; JP 2008237110; CN 101275141; WO 2008/118545; WO 2008/115844; CN 101255408; CN 101250506; CN 101250505; WO 2008/098198; WO 2008/096695; WO 2008/071673; WO 2008/073498; WO 2008/065370; WO 2008/067070; JP 2008127301; JP 2008054644; KR 794395; EP 1881066; WO 2007/147827; CN 101078014; JP 2007300852; WO 2007/048235; WO 2007/044688; WO 2007/032540; CN 1900286; CN 1900285; JP 2006340611; WO 2006/126723; KR 2006029792; KR 2006029795; WO 2006/105082; WO 2006/076094; US 2006/0156430; WO 2006/065126; JP 2006129836; CN 1746293; WO 2006/029398; JP 2006034215; JP 2006034214; WO 2006/009334; WO 2005/111216; WO 2005/080572; US 2005/0150002; WO 2005/061699; WO 2005/052152; WO 2005/038033; WO 2005/038018; WO 2005/030944; JP 2005065618; WO 2005/017106; WO 2005/017105; US 20050037411; WO 2005/010166; JP 2005021106; JP 2005021104; JP 2005021105; WO 2004/113527; CN 1472323; JP 2004261121; WO 2004/013339; WO 2004/011648; DE 10234126; WO 2004/003190; WO 2003/087381; WO 2003/078577; US 20030170627; US 20030166176; US 20030150025; WO 2003/057830; WO 2003/052050; CN 1358756; US 20030092658; US 20030078404; US 20030066103; WO 2003/014341; US 20030022334; WO 2003/008563; EP 1270722; US 20020187538; WO 2002/092801; WO 2002/088341; US 20020160950; WO 2002/083868; US 20020142379; WO 2002/072758; WO 2002/064765; US 20020076777; US 20020076774; US 20020076774; WO 2002/046386; WO 2002/044213; US 20020061566; CN 1315335; WO 2002/034922; WO 2002/033057; WO 2002/029018; WO 2002/018558; JP 2002058490; US 20020022254; WO 2002/008269; WO 2001/098461; WO 2001/081585; WO 2001/051622; WO 2001/034780; CN 1271005; WO 2001/011071; WO 2001/007630; WO 2001/007574; WO 2000/078973; U.S. Pat. No. 6,130,077; JP 2000152788; WO 2000/031273; WO 2000/020566; WO 2000/000585; DE 19826821; JP 11235174; U.S. Pat. No. 5,939,318; WO 99/19493; WO 99/18224; U.S. Pat. No. 5,886,157; WO 99/08812; U.S. Pat. No. 5,869,283; JP 10262665; WO 98/40470; EP 776974; DE 19507546; GB 2294692; U.S. Pat. No. 5,516,674; JP 07147975; WO 94/29434; JP 06205685; JP 05292959; JP 04144680; DD 298820; EP 477961; SU 1693043; JP 01047375; EP 281245; JP 62104583; JP 63044888; JP 62236485; JP 62104582; and JP 62019084.

TABLE 3

Additional cytochrome P450 enzymes for use according to the present disclosure.

| Species | Cyp No. | Accession No. |
|---|---|---|
| Bacillus megaterium | 102A1 | AAA87602 |
| Bacillus megaterium | 102A1 | ADA57069 |
| Bacillus megaterium | 102A1 | ADA57068 |
| Bacillus megaterium | 102A1 | ADA57062 |
| Bacillus megaterium | 102A1 | ADA57061 |
| Bacillus megaterium | 102A1 | ADA57059 |
| Bacillus megaterium | 102A1 | ADA57058 |
| Bacillus megaterium | 102A1 | ADA57055 |
| Bacillus megaterium | 102A1 | ACZ37122 |
| Bacillus megaterium | 102A1 | ADA57057 |
| Bacillus megaterium | 102A1 | ADA57056 |
| Mycobacterium sp. HXN-1500 | 153A6 | CAH04396 |

TABLE 3-continued

Additional cytochrome P450 enzymes for use according to the present disclosure.

| Species | Cyp No. | Accession No. |
|---|---|---|
| Tetrahymena thermophile | 5013C2 | ABY59989 |
| Nonomuraea dietziae | | AGE14547.1 |
| Homo sapiens | 2R1 | NP_078790 |
| Macca mulatto | 2R1 | NP_001180887.1 |
| Canis familiaris | 2R1 | XP_854533 |
| Mus musculus | 2R1 | AAI08963 |
| Bacillus halodurans C-125 | 152A6 | NP_242623 |
| Streptomyces parvus | aryC | AFM80022 |
| Pseudomonas putida | 101A1 | P00183 |
| Homo sapiens | 2D7 | AAO49806 |
| Rattus norvegicus | C27 | AAB02287 |
| Oryctolagus cuniculus | 2B4 | AAA65840 |
| Bacillus subtilis | 102A2 | O08394 |
| Bacillus subtilis | 102A3 | O08336 |
| B. megaterium DSM 32 | 102A1 | P14779 |
| B. cereus ATCC14579 | 102A5 | AAP10153 |
| B. licheniformis ATTC1458 | 102A7 | YP 079990 |
| B. thuringiensis serovar konkukian str. 97-27 | X | YP 037304 |
| R. metallidurans CH34 | 102E1 | YP 585608 |
| A. fumigatus Af293 | 505X | EAL92660 |
| A. nidulans FGSC A4 | 505A8 | EAA58234 |
| A. oryzae ATCC42149 | 505A3 | Q2U4F1 |
| A. oryzae ATCC42149 | X | Q2UNA2 |
| F. oxysporum | 505A1 | Q9Y8G7 |
| G. moniliformis | X | AAG27132 |
| G. zeae PH1 | 505A7 | EAA67736 |
| G. zeae PH1 | 505C2 | EAA77183 |
| M. grisea 70-15 syn | 505A5 | XP 365223 |
| N. crassa OR74 A | 505A2 | XP 961848 |
| Oryza sativa* | 97A | |
| Oryza sativa* | 97B | |
| Oryza sativa | 97C | ABB47954 |

The start methionine ("M") may be present or absent from these sequences.
*See, M. Z. Lv et al., Plant Cell Physiol., 53(6): 987-1002 (2012).

In some embodiments, the heme enzyme in the reaction mixture is a globin enzyme. Globins are a superfamily of globular heme proteins that are typically involved in the transport and binding of oxygen. A characteristic of globins is a three-dimensional fold consisting of eight alpha helices, often labeled A-H, that can fold into a three-over-three sandwich structure. Some globins also contain additional terminal helix extensions. So-called "truncated hemoglobins" contain four alpha helices arranged in a two-over-two sandwich. Globins can be divided into three groups: single-domain globins, flavohemoglobins (not observed in archaea), and globin-coupled sensors (not observed in eukaryotes). All three groups are observed in bacteria. Globin proteins include hemoglobin, myoglobin, neuroglobin, cytoglobin, erythrocruorin, leghemoglobin, non-symbiotic hemoglobin, flavohemoglobins (one group of chimeric globins), globin E, globin-coupled sensors (another group of chimeric globins), protoglobin, truncated 2/2 globin, HbN, cyanoglobin, HbO, and Glb3.

In some embodiments, the globin is M. infernorum hemoglobin comprising the amino acid sequence set forth in SEQ ID NO:5, or a variant thereof containing one or more mutations. Other examples of globins include, but are not limited to, C. jejuni globin (SEQ ID NO:6), V. stercoraria hemoglobin (SEQ ID NO:7), murine neuroglobin (SEQ ID NO:8), human neuroglobin (SEQ ID NO:9), sperm whale myoglobin (SEQ ID NO:10), human cytoglobin (SEQ ID NO:11), and A. suum hemoglobin (SEQ ID NO:12). One or more mutations may reside with the distal binding pocket of M. infernorum hemoglobin, such as at F28, Y29, L32, F43, Q44, N45, Q50, K53, L54 and/or V95 with respect to SEQ ID NO:5, or within the analogous regions of other globins such those containing a three-over-three helix sandwich fold.

In some embodiments, the globin is a truncated globin such as B. subtilis truncated hemoglobin comprising the amino sequence set forth in SEQ ID NO:13 or a variant thereof having one or more mutations. One or more mutations may reside within the distal binding pocket of B. subtilis truncated hemoglobin, for example at T45 and/or at Q49 with respect to SEQ ID NO:13, or at analogous positions of other truncated globins. In some embodiments, the heme protein is a myoglobin or a variant thereof.

Protoglobins were the first globins identified in Archaea such as M. acetivorans, A. pernix, and P. ferrireducens. Protoglobin tertiary structure frequently includes the canonical globin fold, as well as a pre-A helix (termed "Z" in certain instances) and an N-terminal extension. In some embodiments, the heme protein used for formation of C—H insertion products is a protoglobin or a variant thereof. For example, the protoglobin may be an M. acetivorans protoglobin comprising the amino acid sequence set forth in SEQ ID NO:14, an A. pernix protoglobin comprising the amino sequence set forth in SEQ ID NO:15, a P. ferrireducens protoglobin comprising the amino sequence set forth in SEQ ID NO:16, or a variant thereof containing one or more mutations.

Flavohemoglobins (flavoHbs) are typically characterized by an N-terminal heme b binding globin domain, as well as an FAD binding domain and an NADH binding domain. Electrons are transferred from NAD+/NADH via FAD to heme b, where redox chemistry occurs. Flavohemoglobin activity has been implicated in nitric oxide (NO) detoxification and in NO signaling in organisms such as E. coli and R. eutropha. Nitric oxide dioxygenases (NODs) include such flavoHbs, as well as globin-type proteins lacking the NADH binding domain or lacking the NADH binding domain and the FAD binding domain. In some embodiments, the heme protein used for formation of C—H insertion products is an NOD or a variant having one or more mutations in the NOD globin domain. For example, the NOD variant may be a C. necator NOD variant containing one or more mutations at any one residues 1-145 in SEQ ID NO:17 (i.e., within the globin domain of the C. necator NOD). Other structurally similar NOD proteins, including R. marinus NOD comprising the amino acid sequence set forth in SEQ ID NO:4 may also contain such mutations. In some embodiments, the heme protein is R. marinus NOD comprising the amino acid sequence set forth in SEQ ID NO:4, or a variant thereof. In some embodiments, the R. marinus NOD variant comprises one or mutations at Y32 or V97 relative to the amino acid sequence set forth in SEQ ID NO:4.

Accordingly, some embodiments of the present disclosure provide reaction mixtures wherein the heme protein is a globin, a heme-binding globin homolog, or a variant thereof. In some embodiments, the globin is selected from C. jejuni globin, V. stercoraria hemoglobin, murine neuroglobin, human neuroglobin, human cytoglobin, A. suum hemoglobin, B. subtilis truncated hemoglobin, an M. acetivorans protoglobin, an A. pernix protoglobin, a P. ferrireducens protoglobin, C. necator NOD, R. marinus NOD, or a variant thereof. In some embodiments, the globin is not a myoglobin. In some embodiments, the heme-binding globin homolog is a nitric oxide dioxygenase protein from Rhodothermus marinus or a variant thereof. In some embodiments, the nitric oxide dioxygenase protein from Rhodothermus marinus contains a mutation at the position Y32 as determined with reference to SEQ ID NO:4. In some embodiments, the nitric oxide dioxygenase protein from *Rhodothermus marinus* contains the mutation Y32G.

In some embodiments, the reaction mixture further comprises a reducing agent. In some embodiments, the reducing agent is selected from sodium dithionite, NADPH, NADH, L-ascorbic acid, dithiothreitol, β-mercaptoethanol, and tris (2-carboxyethyl)phosphine.

Also provided here are methods for producing C—H insertion products. The methods include:
(a) providing a substrate having an $sp^3$-hybridized C—H bond, a carbene precursor for modification of the carbon atom in the $sp^3$-hybridized C—H bond, and a heme protein comprising an iron porphyrin; and
(b) admixing the components of step (a) under conditions sufficient to produce the C—H insertion product.

In some embodiments, the method is carried out in vitro. In other embodiments, the heme protein is localized within a whole cell and the method is carried out in vivo. In some embodiments, the heme protein is expressed in a bacterial, archaeal, yeast or fungal host organism. In some embodiments, the method is carried out under anaerobic conditions. In other embodiments, the process is carried out under aerobic conditions.

The heme proteins, fragments thereof, homologs thereof, or variants thereof can be, for example, purified prior to addition to a reaction mixture or secreted by a cell present in the reaction mixture. The reaction mixture can contain a cell lysate including the heme protein, fragment thereof, homolog thereof, or variant thereof, as well as other proteins and other cellular materials. Alternatively, a heme protein, fragment thereof, homolog thereof, or variant thereof can catalyze the reaction within a cell expressing the heme protein, fragment thereof, homolog thereof, or variant thereof. Any suitable amount of heme protein can be used in the methods. In general, carbon-hydrogen carbene insertion reaction mixtures contain from about 0.01 mol % to about 10 mol % heme protein with respect to the carbene precursor (e.g., diazo reagent) and/or carbon-containing reagent. The reaction mixtures can contain, for example, from about 0.01 mol % to about 0.1 mol % heme protein, or from about 0.1 mol % to about 1 mol % heme protein, or from about 1 mol % to about 10 mol % heme protein. The reaction mixtures can contain from about 0.01 mol % to about 5 mol % heme protein, or from about 0.05 mol % to about 0.5 mol % heme protein. The reaction mixtures can contain about 0.01, 0.02, 0.05, 0.1, 0.2, 0.3, 0.4, 0.5, 0.6, 0.7, 0.8, 0.9, or about 1 mol % heme protein. In some embodiments, the molar concentration of the heme protein in the reaction mixture ranges from about 0.1 µM to about 100 µM (e.g., 0.1-10 µM or 1-5 µM).

The concentration of the substrate (e.g., a compound of Formula I, Formula Ia, or Formula III) and carbene precursor (e.g., a diazo reagent according to Formula II) are typically in the range of from about 100 µM to about 1 M. The concentration can be, for example, from about 100 µM to about 1 mM, or about from 1 mM to about 100 mM, or from about 100 mM to about 500 mM, or from about 500 mM to 1 M. The concentration can be from about 500 µM to about 500 mM, 500 µM to about 50 mM, or from about 1 mM to about 50 mM, or from about 15 mM to about 45 mM, or from about 15 mM to about 30 mM, or from about 5 mM to about 25 mM, or from about 5 mM to about 15 mM. The concentration of the substrate having the $sp^3$ hybridized C—H bond or carbene precursor can be, for example, about 100, 200, 300, 400, 500, 600, 700, 800, or 900 µM. The concentration of substrate having the $sp^3$ hybridized C—H bond or carbene precursor can be about 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, or 500 mM.

Reaction mixtures can contain additional reagents. As non-limiting examples, the reaction mixtures can contain buffers (e.g., M9-N buffer, 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline, sodium citrate, sodium acetate, and sodium borate), cosolvents (e.g., dimethylsulfoxide, dimethylformamide, ethanol, methanol, isopropanol, glycerol, tetrahydrofuran, acetone, acetonitrile, and acetic acid), salts (e.g., NaCl, KCl, $CaCl_2$, and salts of $Mn^{2+}$ and $Mg^{2+}$), denaturants (e.g., urea and guanadinium hydrochloride), detergents (e.g., sodium dodecylsulfate and Triton-X 100), chelators (e.g., ethylene glycol-bis(2-aminoethylether)-N,N, N',N'-tetraacetic acid (EGTA), 2-({2-[Bis(carboxymethyl) amino]ethyl} (carboxymethyl)amino)acetic acid (EDTA), and 1,2-bis(o-aminophenoxy)ethane-N,N,N',N'-tetraacetic acid (BAPTA)), sugars (e.g., glucose, sucrose, and the like), and reducing agents (e.g., sodium dithionite, NADPH, dithiothreitol (DTT), β-mercaptoethanol (BME), and tris(2-carboxyethyl)phosphine (TCEP)). Buffers, cosolvents, salts, denaturants, detergents, chelators, sugars, and reducing agents can be used at any suitable concentration, which can be readily determined by one of skill in the art. In general, buffers, cosolvents, salts, denaturants, detergents, chelators, sugars, and reducing agents, if present, are included in reaction mixtures at concentrations ranging from about 1 µM to about 1 M. For example, a buffer, a cosolvent, a salt, a denaturant, a detergent, a chelator, a sugar, or a reducing agent can be included in a reaction mixture at a concentration of about 1 µM, or about 10 µM, or about 100 µM, or about 1 mM, or about 10 mM, or about 25 mM, or about 50 mM, or about 100 mM, or about 250 mM, or about 500 mM, or about 1 M. In some embodiments, a reducing agent is used in a sub-stoichiometric amount with respect to the olefin substrate and the diazo reagent. Cosolvents, in particular, can be included in the reaction mixtures in amounts ranging from about 1% v/v to about 75% v/v, or higher. A cosolvent can be included in the reaction mixture, for example, in an amount of about 5, 10, 20, 30, 40, or 50% (v/v).

Reactions are conducted under conditions sufficient to catalyze the formation of the C—H insertion product. The reactions can be conducted at any suitable temperature. In general, the reactions are conducted at a temperature of from about 0° C. to about 40° C. The reactions can be conducted, for example, at about 25° C. or about 37° C. In certain embodiments, high stereoselectivity can be achieved by conducting the reaction at a temperature less than 25° C. (e.g., around 20° C., 10° C., or 4° C.) without reducing the total turnover number of the enzyme catalyst. The reactions can be conducted at any suitable pH. In general, the reactions are conducted at a pH of from about 6 to about 10. The reactions can be conducted, for example, at a pH of from about 6.5 to about 9 (e.g., about 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0). The reactions can be conducted for any suitable length of time. In general, the reaction mixtures are incubated under suitable conditions for anywhere between about 1 minute and several hours. The reactions can be conducted, for example, for about 1 minute, or about 5 minutes, or about 10 minutes, or about 30 minutes, or about 1 hour, or about 2 hours, or about 4 hours, or about 8 hours, or about 12 hours, or about 18 hours, or about 24 hours, or about 48 hours, or about 72 hours. In some embodiments, the reaction is conducted for a period of time ranging from about 6 hours to about 24 hours (e.g., about 6, 7, 8, 9, 10, 11, 12, 13, 14, 15, 16, 17, 18, 19, 20 21, 22, 23, or 24 hours). Reactions can be conducted under aerobic conditions or anaerobic conditions. Reactions can be conducted under an inert atmosphere, such as a nitrogen atmosphere or argon atmosphere. In some embodiments, a solvent is added to the reaction mixture. In some embodiments, the solvent forms a second phase, and the carbene insertion into C—H bonds occurs in the aqueous phase. In some embodiments, the heme protein, fragment thereof, variant thereof, or homolog thereof, is located in the aqueous layer whereas the substrates and/or products are located in an organic layer. Other reaction conditions may be employed in the methods disclosed herein, depending on the identity of a particular heme protein, substrate for C—H insertion, or carbene precursor.

Reactions can be conducted in vivo with intact cells expressing a heme enzyme of the present disclosure. The in vivo reactions can be conducted with any of the host cells used for expression of the heme enzymes, as described herein. A suspension of cells can be formed in a suitable medium supplemented with nutrients (such as mineral micronutrients, glucose and other fuel sources, and the like). Product yields from reactions in vivo can be controlled, in part, by controlling the cell density in the reaction mixtures. Cellular suspensions exhibiting optical densities ranging from about 0.1 to about 50 at 600 nm can be used for the carbene insertion reactions. Other densities can be useful, depending on the cell type, specific heme proteins, or other factors.

The methods can be assessed in terms of the diastereoselectivity and/or enantioselectivity of carbene insertion into carbon-hydrogen bonds—that is, the extent to which the reaction produces a particular isomer, whether a diastereomer or enantiomer. A perfectly selective reaction produces a single isomer, such that the isomer constitutes 100% of the product. As another non-limiting example, a reaction producing a particular enantiomer constituting 90% of the total product can be said to be 90% enantioselective. A reaction producing a particular diastereomer constituting 30% of the total product, meanwhile, can be said to be 30% diastereoselective.

In general, the methods disclosed herein include reactions that are from about 1% to about 99% diastereoselective. The reactions are from about 1% to about 99% enantioselective. The reaction can be, for example, from about 10% to about 90% diastereoselective, or from about 20% to about 80% diastereoselective, or from about 40% to about 60% diastereoselective, or from about 1% to about 25% diastereoselective, or from about 25% to about 50% diastereoselective, or from about 50% to about 75% diastereoselective. The reaction can be about 10%, 15%, 20%, 25%, 30%, 35%, 40%, 45%, 50%, 55%, 60%, 65%, 70%, 75%, 80%, 85%, 90%, or about 95% diastereoselective. The reaction can be from about 10% to about 90% enantioselective, from about 20% to about 80% enantioselective, or from about 40% to about 60% enantioselective, or from about 1% to about 25% enantioselective, or from about 25% to about 50% enantioselective, or from about 50% to about 75% enantioselective. The reaction can be about 10%, 15%, 20%, 25%, 30%, 35%, 40%, 45%, 50%, 55%, 60%, 65%, 70%, 75%, 80%, 85%, 90%, or about 95% enantioselective. Accordingly, some embodiments of the present disclosure provide methods wherein the reaction is at least 30% to at least 90% diastereoselective. In some embodiments, the reaction is at least 30% to at least 90% enantioselective. Preferably, the reaction is at least 80% (e.g., at least about 80%, 81%, 82%, 83%, 84%, 85%, 86%, 87%, 88%, 89%, 90%, 91%, 92%, 93%, 94%, 95%, 96%, 97%, 98%, 99%, or 100%) enantioselective. More preferably, the reaction is at least 90% (e.g., at least about 90%, 91%, 92%, 93%, 94%, 95%, 96%, 97%, 98%, 99%, or 100%) enantioselective.

Any of the heme proteins or heme protein variants described herein can be used in the methods for preparation of C—H insertion products. In some embodiments, the heme protein is a cytochrome P450 or a variant thereof. In some embodiments, the cytochrome P450 is $P450_{BM3}$, a truncated $P450_{BM3}$ comprising residues 1-664 of the amino acid sequence set forth in SEQ ID NO:1, or a variant thereof.

In some embodiments, the P450 polypeptide comprises one or more mutations at positions corresponding to residues N70, A74, V78, A82, F87, M118, P142, F162, T175, M177, A184, S226, H236, E252, I263, H266, T268, A290, T327, A328, A330, L353, I366, C400, I401, T436, L437, T438, E442 as determined with reference to SEQ ID NO.1.

III. HEME PROTEIN VARIANTS FOR C—H INSERTION CATALYSIS

Also provided herein are heme protein variants useful for catalysis of C—H insertion reactions. The heme protein variants include an iron porphyrin and a cytochrome P450 polypeptide, wherein the cytochrome P450 polypeptide comprises one or more amino acid mutations that increase the C—H insertion activity of the enzyme variant relative to the cytochrome P450 polypeptide without the amino acid mutations.

In some embodiments, the cytochrome P450 polypeptide is a CYP102A sub-family polypeptide. In some embodiments, the cytochrome P450 polypeptide is has at least 70% identity to the amino acid sequence for $P450_{BM3}$ set forth in SEQ ID NO:1. In some embodiments, the cytochrome P450 polypeptide is a truncated variant having at least 70% identity to residues 1-644 of $P450_{BM3}$ set forth in SEQ ID NO:1. In some embodiments, the P450 polypeptide contains one or more mutations at positions corresponding to residues N70, A74, V78, A82, F87, M118, P142, F162, T175, M177, A184, S226, H236, E252, I263, H266, T268, A290, T327, A328, A330, L353, I366, C400, I401, T436, L437, T438, and E442 as determined with reference to SEQ ID NO.1. Mutations in one or more groupings of residues can be introduced as described above. In some embodiments, the heme protein variant contains an amino acid sequence that has about 50% or greater (e.g., about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) identity to any one of the amino acid sequences set forth herein, or any particular variant thereof.

In some embodiments, the heme protein variant has a turnover frequency (TOF) between about 1 $min^{-1}$ and 10 $min^{-1}$ (e.g., about 1 $min^{-1}$, 1.5 $min^{-1}$, 2 $min^{-1}$, 2.5 $min^{-1}$, 3 $min^{-1}$, 3.5 $min^{-1}$, 4 $min^{-1}$, 4.5 $min^{-1}$, 5 $min^{-1}$, 5.5 $min^{-1}$, 6 $min^{-1}$, 6.5 $min^{-1}$, 7 $min^{-1}$, 7.5 $min^{-1}$, 8 $min^{-1}$, 8.5 $min^{-1}$, 9 $min^{-1}$, 9.5 $min^{-1}$, or 10 $min^{-1}$). In other embodiments, the TOF is between about 10 $min^{-1}$ and 100 $min^{-1}$ (e.g., about 10 $min^{-1}$, 11 $min^{-1}$, 12 $min^{-1}$, 13 $min^{-1}$, 14 $min^{-1}$, 15 $min^{-1}$, 16 $min^{-1}$, 17 $min^{-1}$, 18 $min^{-1}$, 19 $min^{-1}$, 20 $min^{-1}$, 21 $min^{-1}$, 22 $min^{-1}$, 23 $min^{-1}$, 24 $min^{-1}$, 25 $min^{-1}$, 26 $min^{-1}$, 27 $min^{-1}$, 28 $min^{-1}$, 29 $min^{-1}$, 30 $min^{-1}$, 31 $min^{-1}$, 32 $min^{-1}$, 33 $min^{-1}$, 34 min$^{-1}$, 35 min$^{-1}$, 36 min$^{-1}$, 37 min$^{-1}$, 38 min$^{-1}$, 39 min$^{-1}$, 40 min$^{-1}$, 41 min$^{-1}$, 42 min$^{-1}$, 43 min$^{-1}$, 44 min$^{-1}$, 45 min$^{-1}$, 46 min$^{-1}$, 47 min$^{-1}$, 48 min$^{-1}$, 49 min$^{-1}$, 50 min$^{-1}$, 55 min$^{-1}$, 60 min$^{-1}$, 65 min$^{-1}$, 70 min$^{-1}$, 75 min$^{-1}$, 80 min$^{-1}$, 85 min$^{-1}$, 90 min$^{-1}$, 95 min$^{-1}$, or 100 min$^{-1}$). In other instances, the TOF is greater than about 100 min$^{-1}$ to 1,000 min$^{-1}$ (e.g., greater than about 100 min$^{-1}$, 150 min$^{-1}$, 200 min$^{-1}$, 250 min$^{-1}$, 300 min$^{-1}$, 350 min$^{-1}$, 400 min$^{-1}$, 450 min$^{-1}$, 500 min$^{-1}$, 550 min$^{-1}$, 600 min$^{-1}$, 650 min$^{-1}$, 700 min$^{-1}$, 750 min$^{-1}$, 800 min$^{-1}$, 850 min$^{-1}$, 900 min$^{-1}$, 950 min$^{-1}$, 1,000 min$^{-1}$, or more). In some instances, the TOF is greater than about 10 min$^{-1}$. In other instances, the TOF is greater than about 45 min$^{-1}$.

In other embodiments, the heme protein variant has a total turnover number (TTN), which refers to the maximum number of molecules of a substrate that the protein can convert before becoming inactivated, of between about 1 and 100 (e.g., about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100). In some other embodiments, the TTN is between about 100 and 1,000 (e.g., about 100, 150, 200, 250, 300, 350, 400, 450, 500, 550, 600, 650, 700, 750, 800, 850, 900, 950, or 1,000). In some embodiments, the TTN is between about 1,000 and 2,000 (e.g., about 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950 or 2,000). In other embodiments, the TTN is at least about 2,000 (e.g., at least about 2,000, 2,500, 3,000, 3,500, 4,000, 4,500, 5,000, 5,500, 6,000, 6,500, 7,000, 7,500, 8,000, 8,500, 9,000, 9,500, or 10,000). In some instances, the TTN is greater than about 70. In other instances, the TTN is greater than about 2,000.

In some embodiments, the heme protein variant has enhanced activity of at least about 1.5 to 2,000 fold (e.g., at least about 1.5, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950, 2,000, or more) fold compared to the corresponding wild-type heme protein.

In some embodiments, activity is expressed in terms of turnover frequency (TOF). In particular embodiments, the TOF of the heme protein variant or fragment thereof is at least about 1.5, 2, 2.5, 3, 3.5, 4, 4.5, 5, 5.5, 6, 6.5, 7, 7.5, 8, 8.5, 9, 9.5, or 10 fold higher than the corresponding wild-type protein.

In other instances, activity is expressed in terms of total turnover number (TTN). In particular instances, the TTN of the theme protein variant or fragment thereof is about at least about 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950, or 2,000 fold higher than the corresponding wild-type protein.

In certain embodiments, mutations can be introduced into the target gene using standard cloning techniques (e.g., site-directed mutagenesis, site-saturated mutagenesis) or by gene synthesis to produce the heme proteins. In some embodiments, the heme variant is recombinantly expressed and optionally isolated and/or purified for carrying out the in vitro carbon-hydrogen carbene insertion reactions of the present disclosure. In other embodiments, the heme protein, fragment thereof, variant thereof, or homolog thereof is expressed in whole cells such as bacterial cells, archaeal cells, yeast cells, fungal cells, insect cells, plant cells, or mammalian cells, and these cells are used for carrying out the in vivo carbon-hydrogen carbene insertion reactions. The wild-type or mutated gene can be expressed in a whole cell using an expression vector under the control of an inducible promoter or by means of chromosomal integration under the control of a constitutive promoter. Carbon-hydrogen carbene insertion activity can be screened in vivo or in vitro by following product formation by GC or HPLC.

Suitable bacterial host cells include, but are not limited to, BL21 *E. coli*, DE3 strain *E. coli*, *E. coli* M15, DH5α, DH10β, HB101, T7 Express Competent *E. coli* (NEB), *B. subtilis* cells, *Pseudomonas fluorescens* cells, and cyanobacterial cells such as *Chlamydomonas reinhardtii* cells and *Synechococcus elongates* cells. Non-limiting examples of archaeal host cells include *Pyrococcus furiosus*, *Metallosphera sedula*, *Thermococcus litoralis*, *Methanobacterium thermoautotrophicum*, *Methanococcus jannaschii*, *Pyrococcus abyssi*, *Sulfolobus solfataricus*, *Pyrococcus woesei*, *Sulfolobus shibatae*, and variants thereof. Fungal host cells include, but are not limited to, yeast cells from the genera *Saccharomyces* (e.g., *S. cerevisiae*), *Pichia* (*P. Pastoris*), *Kluyveromyces* (e.g., *K. lactis*), *Hansenula* and *Yarrowia*, and filamentous fungal cells from the genera *Aspergillus*, *Trichoderma*, and *Myceliophthora*. Suitable insect host cells include, but are not limited to, Sf9 cells from *Spodoptera frugiperda*, Sf21 cells from *Spodoptera frugiperda*, Hi-Five cells, BTI-TN-5B1-4 *Trichophusia ni* cells, and Schneider 2 (S2) cells and Schneider 3 (S3) cells from *Drosophila melanogaster*. Non-limiting examples of mammalian host cells include HEK293 cells, HeLa cells, CHO cells, COS cells, Jurkat cells, NSO hybridoma cells, baby hamster kidney (BHK) cells, MDCK cells, NIH-3T3 fibroblast cells, and any other immortalized cell line derived from a mammalian cell. Non-limiting examples of plant host cells include those from tobacco, tomato, potato, maize, rice, lettuce, and spinach. In general, cells from plants that have short generation times and/or yield reasonable biomass with standard cultivation techniques are preferable.

In certain embodiments, heme proteins inside living cells are provided. As a non-limiting example, bacterial cells (e.g., *E. coli*) can be used as host whole cell catalysts for the in vivo carbon-hydrogen carbene insertion reactions, although any number of host whole cells may be used, including but not limited to the host cells described herein. In some embodiments, host whole cell catalysts containing heme proteins can significantly enhance the total turnover number (TTN) compared to the in vitro reactions using isolated heme proteins.

The expression vector comprising a nucleic acid sequence that encodes the heme protein can be a viral vector, a plasmid, a phage, a phagemid, a cosmid, a fosmid, a bacteriophage (e.g., a bacteriophage P1-derived vector (PAC)), a baculovirus vector, a yeast plasmid, or an artificial chromosome (e.g., bacterial artificial chromosome (BAC), a yeast artificial chromosome (YAC), a mammalian artificial chromosome (MAC), and human artificial chromosome (HAC)). Expression vectors can include chromosomal, non-chromosomal, and synthetic DNA sequences. Equivalent expression vectors to those described herein are known in the art and will be apparent to the ordinarily skilled artisan.

The expression vector can include a nucleic acid sequence encoding a heme protein that is operably linked to a promoter, wherein the promoter comprises a viral, bacterial, archaeal, fungal, insect, plant, or mammalian promoter. In certain embodiments, the promoter is a constitutive promoter. In some embodiments, the promoter is an inducible promoter. In other embodiments, the promoter is a tissue-specific promoter or an environmentally regulated or a developmentally regulated promoter.

In some embodiments, the nucleic acid sequence encodes a heme protein that comprises an amino acid sequence that has about 70% or greater (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) identity to any one of the amino acid sequences set forth herein, or any particular variant thereof. In other embodiments, the nucleic acid sequence encodes a heme protein that comprises an amino acid sequence that has about 80% or greater (e.g., about 80%, 81%, 82%, 83%, 84%, 85%, 86%, 87%, 88%, 89%, 90%, 91%, 92%, 93%, 94%, 95%, 96%, 97%, 98%, 99%, or 100%) identity to any one of the amino acid sequences set forth herein, or any particular variant thereof. In particular embodiments, the nucleic acid sequence encodes a heme protein that comprises an amino acid sequence that has about 90% or greater (e.g., about 90%, 91%, 92%, 93%, 94%, 95%, 96%, 97%, 98%, 99%, or 100%) identity to any one of the amino acid sequences set forth herein, or any particular variant thereof. In some instances, the nucleic acid sequence encodes a heme protein that comprises an amino acid sequence that is about 95%, 96,%, 97%, 98%, 99%, or 100% identical to any one of the amino acid sequences set forth herein, or any particular variant thereof.

In other embodiments, the nucleic acid sequence encodes a heme protein that comprises an amino acid sequence that contains between about 5 and 125 (e.g., about 5, 10, 15, 20, 25, 30, 35, 40, 45, 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, or 125) of the amino acids in any one of the polypeptide sequences disclosed herein, or any particular variant thereof. The amino acids may be contiguous, or separated by any number of amino acids.

It is understood that affinity tags may be added to the N- and/or C-terminus of a heme protein, fragment thereof, variant thereof, or homolog thereof expressed using an expression vector to facilitate protein purification. Non-limiting examples of affinity tags include metal binding tags such as His6-tags (SEQ ID NO: 18) and other tags such as glutathione S-transferase (GST).

Non-limiting expression vectors for use in bacterial host cells include pCWori, pET vectors such as pET22 (EMD Millipore), pBR322 (ATCC37017), pQE™ vectors (Qiagen), pBluescript™ vectors (Stratagene), pNH vectors, lambda-ZAP vectors (Stratagene); ptrc99a, pKK223-3, pDR540, pRIT2T (Pharmacia), pRSET, pCR-TOPO vectors, pET vectors, pSyn_1 vectors, pChlamy_1 vectors (Life Technologies, Carlsbad, Calif.), pGEM1 (Promega, Madison, Wis.), and pMAL (New England Biolabs, Ipswich, Mass.). Non-limiting examples of expression vectors for use in eukaryotic host cells include pXT1, pSG5 (Stratagene), pSVK3, pBPV, pMSG, pSVLSV40 (Pharmacia), pcDNA3.3, pcDNA4/TO, pcDNA6/TR, pLenti6/TR, pMT vectors (Life Technologies), pKLAC1 vectors, pKLAC2 vectors (New England Biolabs), pQE™ vectors (Qiagen), BacPak baculoviral vectors, pAdeno-X™ adenoviral vectors (Clontech), and pBABE retroviral vectors. Any other vector may be used as long as it is replicable and viable in the host cell.

IV. EXAMPLES

Example 1

Testing of C—H Alkylation Activity in Enzyme Panel

Biological systems use a limited set of chemical strategies to form C—C bonds during construction of organic molecules. Whereas many of these approaches rely on the manipulation of functional groups, certain enzymes, including members of the radical S-adenosylmethionine (SAM) family, can perform direct alkylation of $sp^3$ C—H bonds. This has been an especially versatile strategy for structural diversification, as seen by its essential role in the biosynthesis of structurally varied natural products and cofactors. Known biological machineries for this transformation, however, are limited to enzymes that transfer a methyl group or conjugate an activated radical acceptor substrate to specific molecules, with methylation as a common mode for $sp^3$ C-alkyl installation by radical SAM enzymes (FIG. 1A). Inspired by the significant impact of this chemistry on natural metabolite diversity, but recognizing the limitations of known enzymes, a new enzymatic strategy for the alkylation of $sp^3$ C—H bonds was sought as described below.

Figure 1B:
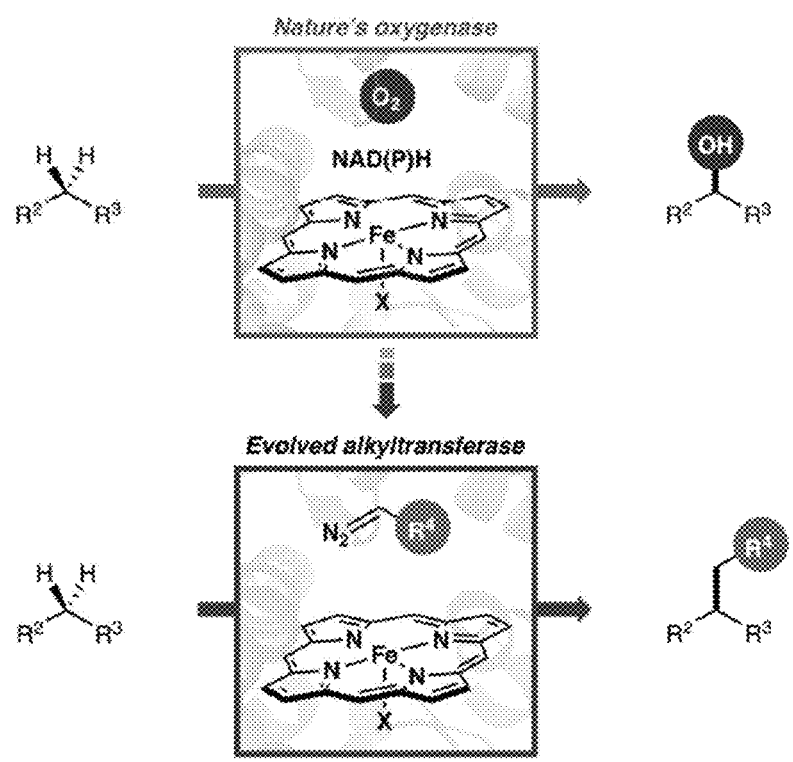
FIG. 1B shows oxygenation catalyzed by cytochrome P450 monooxygenase (top) and envisioned alkylation reaction achieved under heme protein catalysis (bottom). Structural illustrations are adapted from PDB: 5UL4 (radical SAM enzyme) and PDB: 2IJ2 (cytochrome P450$_{BM3}$). Ad, adenosyl; R, organic functional group; X, amino acid.

In designing the new enzymatic strategy, inspiration was drawn from the most widely used biological C—H functionalization transformation, C—H oxygenation. It was envisioned that proteins which naturally have this function, and perhaps others with the same cofactor, could be repurposed for C—H alkylation chemistry. Enzymes such as the cytochromes P450, which accept a vast range of structurally distinct substrates, accomplish C—H oxygenation using an iron-heme cofactor. Their activities rely on the activation of molecular oxygen for the controlled generation of a high-energy iron-oxo intermediate, which selectively inserts into a substrate C—H bond to produce the hydroxylated product. In analogy to the C—H oxygenation reaction, it was envisioned that the combination of a heme protein and a diazo compound would generate a protein-bound iron-carbene species and that this carbene could participate in a selective C—H insertion reaction with an alkane substrate (FIG. 1B). While it has been shown that heme proteins are capable of performing carbene transfer processes such as cyclopropanation and heteroatom-hydrogen bond insertions, their functionalization of $sp^3$ C—H bonds remained elusive.

Metal-carbene $sp^3$ C—H insertion in small-molecule catalysis, especially intermolecular and stereoselective versions of this reaction, typically relies on transition metal complexes based on rhodium, iridium, and others. Artificial metalloproteins for carbene C—H insertion have been created by introducing an iridium-heme into variants of apo heme proteins. Though rare, there are a few examples of iron-carbene $sp^3$ C—H insertion. The iron-catalyzed examples employ elevated temperatures (e.g., 80° C.), are stoichiometric, or are restricted to intramolecular reactions, indicating a high activation energy barrier for C—H insertion with an iron-carbene. However, because the protein framework of an enzyme can impart significant rate enhancements to reactions and even confer activity to an otherwise unreactive cofactor, it was surmised that directed evolution could be used to reconfigure a heme protein to overcome the barrier for the iron-carbene C—H insertion reaction and acquire this new function (FIG. 1B).

Figure 2A:
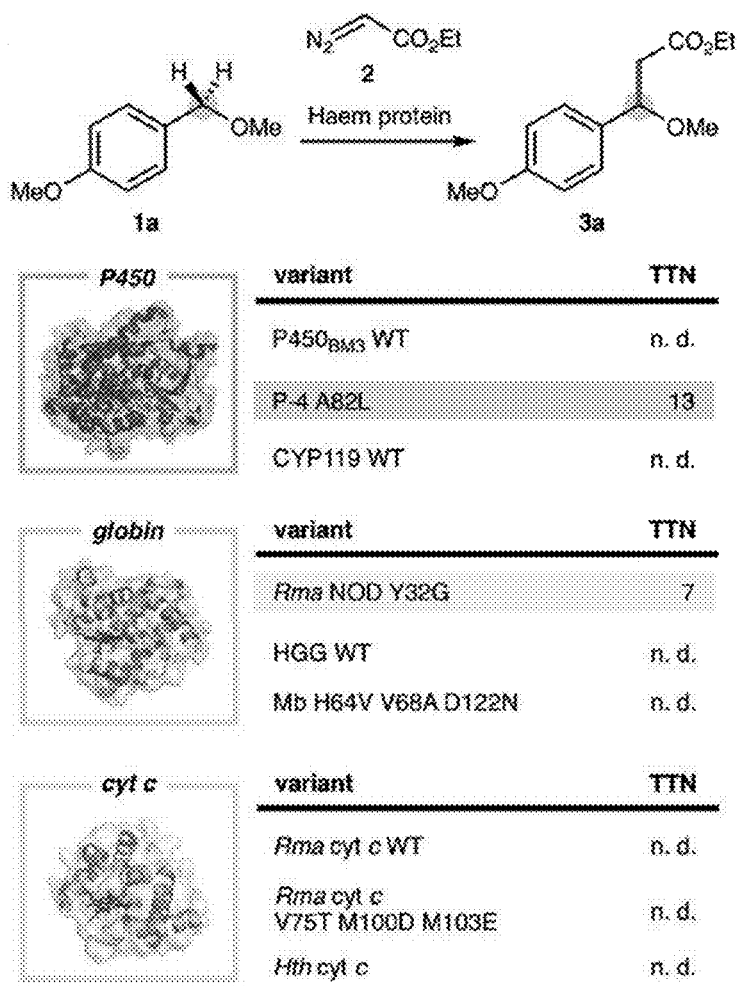
FIG. 2A shows heme protein-catalyzed $sp^3$ C—H alkylation. A select subset of heme proteins tested for promiscuous C—H alkylation activity is shown. Structural illustrations are of representative superfamily members with the heme cofactor shown as sticks: cytochrome P450$_{BM3}$ (PDB: 2IJ2), sperm whale myoglobin (PDB: 1A6K), and Rma cytochrome c (PDB: 3CP5). TTN=total turnover number; n.d.=not detected; WT=wild type; cyt c=cytochrome c; HGG=Hell's Gate globin; Hth=*Hydrogenobacter thermophilus*.

In initial studies, a panel of seventy-eight heme proteins, which included variants of cytochromes P450, cytochromes c, and globin homologs, was tested. The heme proteins in whole *Escherichia coli* (*E. coli*) cells were combined with p-methoxybenzyl methyl ether (1a) and ethyl diazoacetate (2) at room temperature under anaerobic conditions; the resulting reactions were analyzed for formation of C—H alkylation product 3a (FIG. 2A). It was discovered that heme proteins from two superfamilies showed low levels of this promiscuous activity, establishing the possibility of creating C—H alkylation enzymes with very different protein architectures. An engineered variant of cytochrome P450$_{BM3}$ from *Bacillus megaterium* with an axial cysteine-to-serine mutation (cytochrome "P411"), P-4 A82L, provided 3a with 13 total turnovers (TTN). In addition, nitric oxide dioxygenase from *Rhodothermus marinus* containing the Y32G mutation (Rma NOD Y32G) catalyzed the reaction with 7 TTN. A second alkane substrate, 4-ethylanisole (1i), was also accepted by the nascent C—H alkylation enzymes, albeit with lower turnover numbers (Table 5). The heme cofactor alone (iron protoporphyrin IX) or in the presence of bovine serum albumin were inactive (Tables 4 and 5).

TABLE 4

Initial results for C-H alkylation of p-methoxybenzyl methyl ether (1a) with ethyl diazoacetate (2) catalyzed by heme proteins and control reactions.

| Entry | Catalyst | Catalyst concentration | TTN to 3a |
|---|---|---|---|
| 1 | P-4 A82L (in *E. coli* cells, OD600 = 29) | 4.0 μM | 13 |
| 2 | Rma NOD Y32G (in *E. coli* cells, OD600 = 30) | 11.6 μM | 7 (12†) |
| 3 | Vector control (in *E. coli* cells, OD600 = 30)* | N. A. | n.d. |
| 4 | Hemin | 25.0 μM | n.d.† |
| 5 | Hemin + BSA | 25.0 μM (hemin), 37.5 μg/mL (BSA) | n.d.† |

Reactions summarized in Table 4 were performed with 10 mM 1a and 10 mM 2; results are the average of duplicate reactions. BSA=bovine serum albumin; TTN=total turnover number; n. d.=not detected. Reactions marked with † in entries 2, 4, and 5 contained 1 mM Na$_2$S$_2$O$_4$, used as reductant. The vector control in Entry 3 indicates that *E. coli* harboring pET22b(+) encoding a protein which does not have a transition metal cofactor (halohydrin dehalogenase, UniProt ID: Q93D82) was employed in the reaction.

TABLE 5

Initial results for C-H alkylation of 4-ethylanisole (1i) with ethyl diazoacetate (2) catalyzed by heme proteins and control reactions.

| Entry | Catalyst | Catalyst concentration | TTN to 3i |
|---|---|---|---|
| 1 | P-4 A82L (in *E. coli* cells, OD600 = 21) | 4.0 μM | 3 |
| 2 | Rma NOD Y32G (in *E. coli* cells, OD600 = 30) | 11.6 μM | <1 (2†) |
| 3 | Vector control (in *E. coli* cells, OD600 = 30) | N. A. | n.d. |
| 4 | Hemin | 25.0 μM | n.d.† |
| 5 | Hemin + BSA | 25.0 μM (hemin), 37.5 μg/mL (BSA) | n.d.† |

Reactions summarized in Table 5 were performed with 10 mM 1i and 10 mM 2; results are the average of duplicate reactions. Otherwise, the reactions were conducted as noted for Table 4. Reactions marked with † for Entries 2, 4, and 5 contained 1 mM Na$_2$S$_2$O$_4$, used as reductant.

Example 2

Directed Evolution of a C—H Alkylation Enzyme Catalyst

Figure 2B:
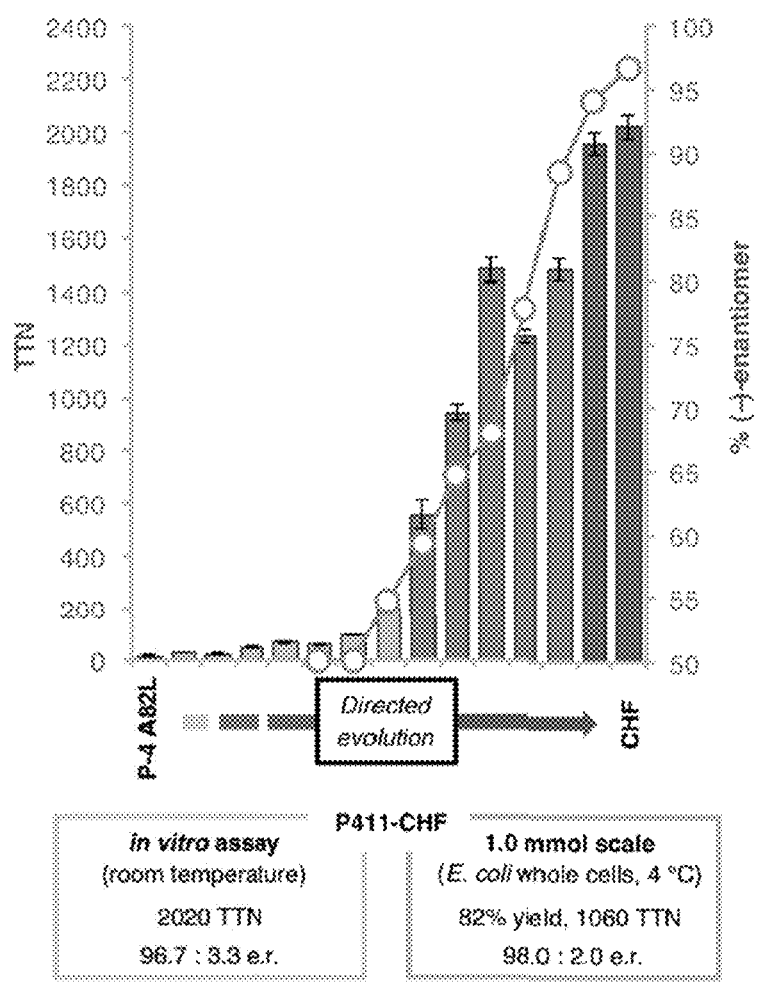
FIG. 2B shows the directed evolution of a cytochrome P411 for enantioselective C—H alkylation (reaction shown in FIG. 2A). Data in the bar graph are average TTNs from reactions performed in quadruplicate; error bars represent one standard deviation. Unless otherwise indicated, reaction conditions were heme protein in *E. coli* whole cells (OD600=30, (FIG. 2A)) or in clarified *E. coli* lysate (FIG. 2B), 10 mM alkane 1a, 10 mM ethyl diazoacetate, 5 vol % EtOH in M9-N buffer at room temperature under anaerobic conditions for 18 hours. Reactions performed with lysate contain 1 mM $Na_2S_2O_4$. TTN is defined as the amount of indicated product divided by total heme protein as measured by the hemochrome assay.
Figure 2C:
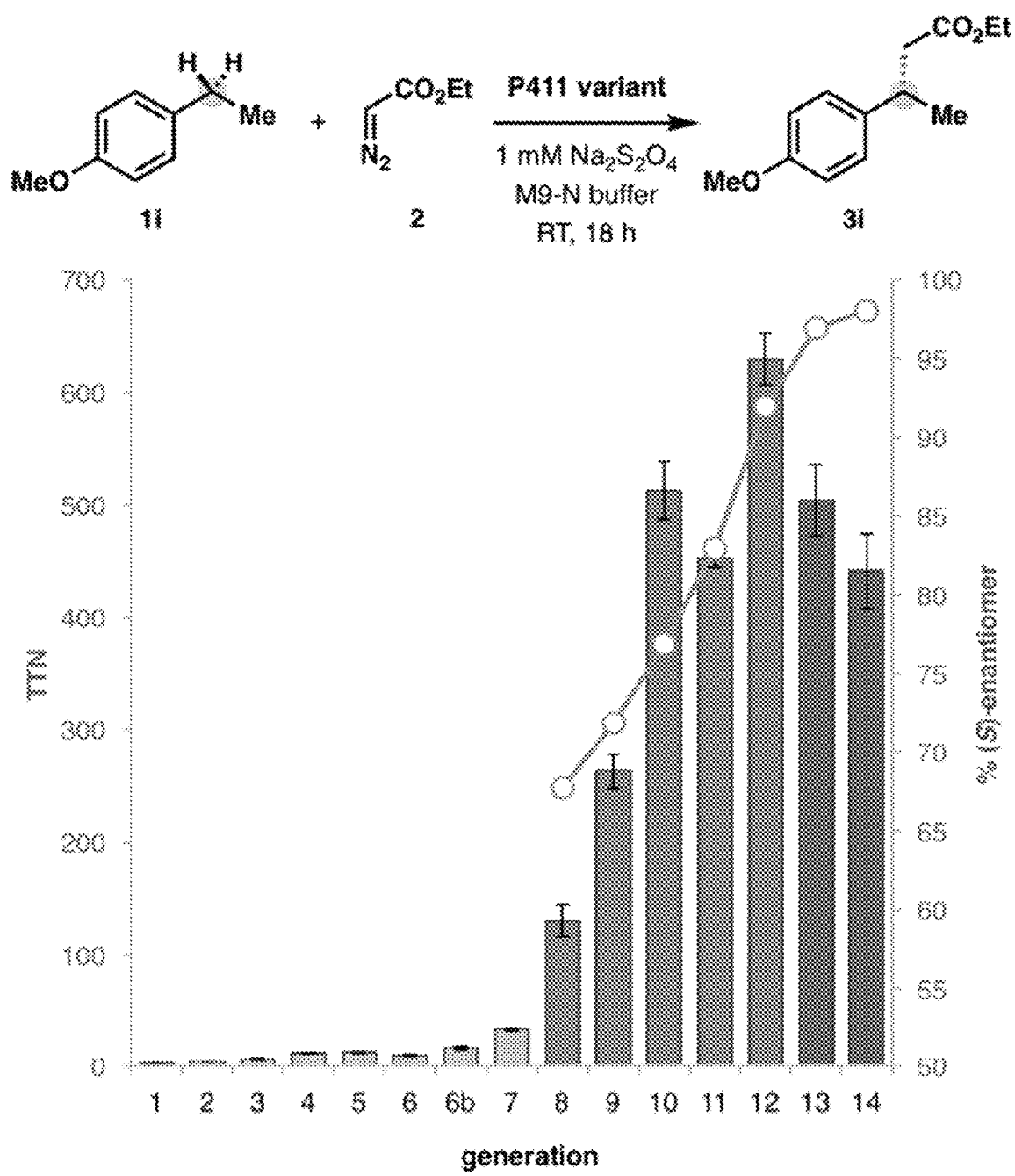
FIG. 2C shows the evolutionary lineage from P-4 A82L to P411-CHF evaluated for C—H alkylation of 4-ethylanisole (1i).

With P411 P-4 A82L as the starting template, sequential rounds of site-saturation mutagenesis and screening in whole *E. coli* cells were performed to identify increasingly active and enantioselective biocatalysts for C—H alkylation. Amino acid residues chosen for mutagenesis included those which line the active site pocket, reside on loops and other flexible regions of the protein, or possess a nucleophilic side chain. Improved variants were subsequently evaluated in reactions using clarified *E. coli* lysate with alkanes p-methoxybenzyl methyl ether (1a) and 4-ethylanisole (1i) (FIG. 2B and FIG. 2C).

Site-saturation libraries were generated employing the "22c-trick" method and screened in one 96-well plate; double site-saturation libraries were generated using the same method to target two different sites and these were screened in three 96-well plates.

Cells in deep-well 96-well plates were pelleted (3,000×g, 5 min, RT) and resuspended in M9-N buffer (20 μL/well) by gentle vortexing. A GOX oxygen depletion system was added (20 μL/well of a stock solution containing 14,000 U/mL catalase and 1,000 U/mL glucose oxidase in 0.1 M potassium phosphate buffer, pH 8.0) and the 96-well plate was transferred into an anaerobic chamber. In the anaerobic chamber, argon-sparged reaction buffer (50 mM glucose in M9-N or 33 mM glucose in M9-N, 300 μL/well) was added, followed by alkane (10 μL/well, 400 mM in EtOH) and ethyl diazoacetate (10 μL/well, 400 mM in EtOH). In some cases, the substrates and reaction buffer were mixed together prior to addition to the plate. The plate was sealed with an aluminum foil and shaken at room temperature and 500 rpm in the anaerobic chamber. After 5-20 hours, the seal was removed and the reactions were worked up for analysis using the methods described below.

Product formation screening using GC and GC-MS. After 5-20 hours, a solution of 0.4 mM 1,3,5-trimethoxybenzene (internal standard) in a mixed solvent system (cyclohexane/ethyl acetate=1:1, 510 μL) was added. The plate was tightly sealed with a reusable silicone mat, vortexed (15 s×3) and centrifuged (3,000×g, 5 min) to completely separate the organic and aqueous layers. The organic layers (180 μL/well) were transferred to 300 μL vial inserts, which were then placed in 2 mL vials and analyzed by GC.

Product formation screening using HPLC. After 5-20 hours, the reaction mixtures, or an aliquot thereof (150 μL/well), were quenched by the addition of an equal or greater volume of acetonitrile (400 μL/well or 150-200 μL/well). This step was kept consistent within each round of directed evolution. The plate containing the resulting mixture was tightly sealed with a reusable silicone mat, vortexed (15 s×3) and centrifuged (3,000×g, 5 min) to pellet the cells. The supernatant was filtered through an AcroPrep 96-well filter plate (0.2 μm) into a shallow-well plate and analyzed by reverse-phase HPLC.

Enantioselectivity screening. After 5-24 hours, mixed solvent (cyclohexane/ethyl acetate=1:1, 250-500 μL/well) was added to the reaction mixtures or aliquots thereof (250 μL). The plate containing the resulting mixture was tightly sealed with a reusable silicone mat, vortexed (15 s×3) and centrifuged (3,000×g, 5 min) to completely separate the organic and aqueous layers. When smaller volumes of mixed solvent were used for the extraction (<400 μL), the extraction mixture was transferred to a 1.6 mL Eppendorf tube, vortexed (15 s×3), and centrifuged (20,000×g, 1 min). The organic layers (180 µL/well) were transferred to 300 µL vial inserts, which were then placed in 2 mL vials and analyzed by chiral HPLC (IC column, 2% i-PrOH in n-hexane).

Figure 7:
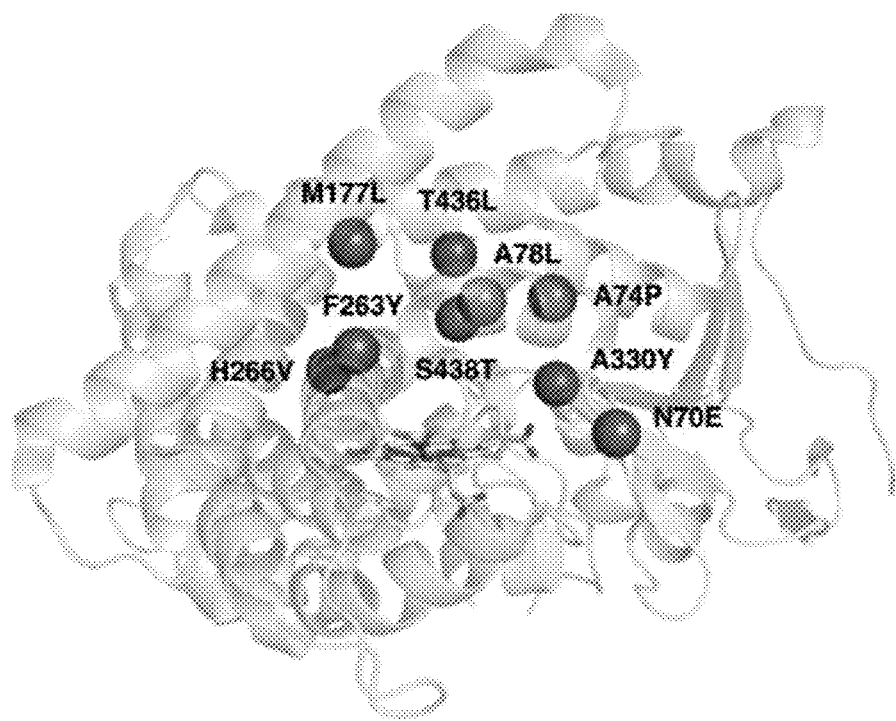
FIG. 7 shows the structural visualization of amino acids mutated during directed evolution of P-4 A82L to P411-CHF.

Following the general screening in 96-well plate procedure, variants which exhibited higher formation of C—H alkylation product (3a or 3i) or improved enantioselectivity for product 3a were identified. A summary of the amino acid residues targeted for mutagenesis is presented in Table 6, as well as the beneficial mutation(s) selected for each round of mutagenesis. The locations of the selected beneficial mutations are displayed on a structural model of the P411 enzyme shown in FIG. 7.

For the evolution study summarized in Table 6, some residues were saturated more than once, in different parents. "Gen"=generation; "N. A."=not applicable. Residues for site-saturation mutagenesis libraries are listed relative to the amino acid at that position in wild-type $P450_{BM3}$. Beneficial mutations are listed relative to the amino acid at that position in the parent protein. Only NDT libraries were constructed and screened for the P329X-F331X double-site saturation experiment in Entry 12.

The structure of P-4 A82L (heme domain) was modeled using the crystal structure of a related P411 variant (PDB: 5UCW), which contains two additional mutations. Considering only the changes incurred in the heme domain, the following mutations were accumulated in going from P-4

TABLE 6

Summary of directed evolution for C-H alkylation.

| Round | Parent | Diversification Strategy | Screening substrate (selection criteria) | Changes Identified* |
|---|---|---|---|---|
| 1 | P-4 A82L | Individual variants identified as active for C-H amination14 | 4-ethylanisole (1i) (activity) | F263Y |
| 2 | P-4 A82L F263Y | Site-saturation mutagenesis A78X | 4-ethylanisole (1i) (activity) | A78L |
| 3 | P-4 A82L F263Y A78L | Site-saturation mutagenesis T327X | 4-ethylanisole (1i) (activity) | T327I |
| 4 | P411-gen4 (P-4 A82L F263Y A78L T327I) | Site-saturation mutagenesis A74X, E267X | 4-ethylanisole (1i) (activity) | A74G |
| 5 | P411-gen5 (P411-gen4 A74G) | Site-saturation mutagenesis A328X, H92X, R255X, A264X, H100X, F393X, L437X | p-methoxybenzyl methyl ether (1a) (activity) | L437Q |
| 6 | P411-gen6 (P411-gen5 L437Q) | Protein truncations: full-length P411, ΔFAD domain, heme-domain only | p-methoxybenzyl methyl ether (1a) (activity) | ΔFAD domain |
| 6b | P411-gen6b (P411ΔFAD-gen6) | Site-saturation mutagenesis A78X, F87X, I263X, T438X | p-methoxybenzyl methyl ether (1a) (activity) | S438T |
| 7 | P411-gen7 (P411-gen6b S438T) | Site-saturation mutagenesis A330X, F331X, T436X, A82X, L181X, L188X | p-methoxybenzyl methyl ether (1a) (activity) | T436L |
| 8 | P411-gen8 (P411-gen7 T436L) | Site-saturation mutagenesis D63X, F162X, M177X, V178X, L439X | 4-ethylanisole (1i) (activity) | M177L |
| 9 | P411-gen9 (P411-gen8 M177L) | Site-saturation mutagenesis F87X, E267X, M118X, L437X, H266X, S332X, T260X, T365X | 4-ethylanisole (1i) (activity) | H266V |
| 10 | P411-gen10 (P411-gen9 H266V) | Site-saturation mutagenesis N70X, T88X, H171X, H361X, P329X, T269X, L75X, L52X | 4-ethylanisole (1i) (activity) & p-methoxybenzyl methyl ether (1a) (enantioselectivity) | N70E |
| 11 | P411-gen11 (P411-gen10 N70E) | Site-saturation mutagenesis L71X, S72X, F261X, G265X, L86X, I401X, A330X, C400X | p-methoxybenzyl methyl ether (1a) (activity & enantioselectivity) | A330Y |
| 12 | P411-gen12 (P411-gen11 A330Y) | Double site-saturation mutagenesis P329X-F331X, T327X-T268X, A74X-L437X | p-methoxybenzyl methyl ether (1a) (activity & enantioselectivity) | I327T |
| 13a | P411-gen13 (P411-gen12 I327T) | Double site-saturation mutagenesis L181X-L437X, V178XE267X, M118X-I401X | p-methoxybenzyl methyl ether (1a) (activity & enantioselectivity) | None |
| 13b | P411-gen13 (P411-gen12 I327T) | Testing previously identified beneficial mutations | p-methoxybenzyl methyl ether (1a) (activity & enantioselectivity) | G74P, Q437L |
| 14 | P411-CHF P411-gen13 G74P Q437L | N.A. | N.A. | N.A. |

A82L to P411-CHF: N70E, A74P, A78L, M177L, F263Y, H266V, A330Y, T436L, S438T (shown as spheres, residues 327 and 437 were not included in this analysis because P-4 A82L and P411-CHF contain the same amino acid residues at those positions). Most of the mutations are at positions that line the distal heme pocket and all of the mutated residues are within 15 Å of the iron atom in the heme cofactor.

Variants which were identified to show higher activity and/or enantioselectivity during screening were streaked out on LBamp agar plates. A single colony was selected, sequenced, and the TTN measured for both products 3a and 3i using clarified lysate of E. coli cells overexpressing the desired protein.

Lysates for biocatalytic reactions were prepared as follows: E. coli cells expressing the appropriate heme protein variant were resuspended in M9-N buffer and adjusted to OD600=60. The cell suspension, in 3 mL portions, was lysed by sonication using a Qsonica Q500 sonicator equipped with a microtip (2 mins, 1 second on, 1 second off, 25% amplitude); samples were kept on wet ice for this process. The resulting lysed solution was centrifuged (20,000×g, 10 min, 4° C.) to remove cell debris.

Protein concentration of the supernatant (clarified lysate) was determined using the hemochrome assay. In a falcon tube, a solution of 0.2 M NaOH, 40% (v/v) pyridine, 0.5 mM $K_3Fe(CN)_6$ was prepared (pyridine-NaOH—$K_3Fe(CN)_6$ solution). Separately, a solution of 0.5 M $Na_2S_2O_4$ (sodium dithionite) was prepared in 0.1 M NaOH. To an Eppendorf tube containing 500 µL of clarified lysate in M9-N buffer was added 500 µL of the pyridine-NaOH—$K_3Fe(CN)_6$ solution, mixed, and transferred to a cuvette; the UV-Vis spectrum of the oxidized FeIII state was recorded immediately. To the cuvette was then added 10 µL of the sodium dithionite solution. The cuvette was sealed with parafilm and the UV-Vis spectrum of the reduced FeII state was recorded immediately. A cuvette containing 500 µL of M9-N, 100 µL 1 M NaOH, 200 µL pyridine, and 200 µL water (complete mixture without protein and $K_3Fe(CN)_6$) was used as a reference for all absorbance measurements. Concentrations of cytochromes P450, cytochromes P411, and globins were determined using a published extinction coefficient for heme b, $\varepsilon 556(\text{reduced})-540(\text{oxidized})=23.98$ mM$^{-1}$ cm$^{-1}$. See, Berry, et al. *Anal. Biochem.* 161, 1-15 (1987). Cytochrome c concentration was measured using a modified procedure, reported previously. See, Kan et al. *Science* 354, 1048-1051 (2016).

The protein concentration in lysate was adjusted to the desired amount by the addition of M9-N buffer. Lysate was placed in a sealed vial and the headspace of the vial was purged with a stream of argon for at least 40 minutes. The lysate was kept on ice during all parts of this procedure. Separately, D-glucose solution (500 mM in M9-N buffer) and $Na_2S_2O_4$ (20 mM in M9-N) were degassed by bubbling the solutions with argon for at least 40 minutes. All solutions were then transferred into an anaerobic chamber for reaction set up. To a 2 mL vial were added a GOX oxygen depletion solution (20 µL of stock solution containing 14,000 U/mL catalase and 1,000 U/mL glucose oxidase in 0.1 M potassium phosphate buffer, pH 8.0), D-glucose (20 µL of 500 mM stock solution in M9-N buffer), lysate (320 µL), $Na_2S_2O_4$ (20 µL of 20 mM solution in M9-N), alkane (10 µL of 400 mM stock solution in EtOH), and ethyl diazoacetate (10 µL of 400 mM stock solution in EtOH) in the listed order. Final reaction volume was 400 µL; final concentrations were typically 2.0 µM heme protein, 1 mM $Na_2S_2O_4$, 10 mM alkane, 10 mM ethyl diazoacetate, and 25 mM D-glucose. The vials were sealed, removed from the anaerobic chamber, and shaken at room temperature and 500 rpm for 18 hours.

FIG. 2C shows the results of reactions using clarified lysate of E. coli expressing the indicated heme protein variant, 10 mM alkane 1i, 10 mM ethyl diazoacetate (2), and 1 mM $Na_2S_2O_4$. Reactions with generation 1, 2, and 3 variants employed 4.0 µM heme protein; all other reactions used 2.0 µM heme protein. Data in the bar graph are average TTNs from reactions performed in quadruplicate; error bars represent one standard deviation. TTN=total turnover number; RT=room temperature. Enantiomeric ratios of the enzymatic products produced by P411-gen6 and further evolved variants were also characterized. The results are summarized in Tables 7 and 8.

TABLE 7

Enzymatic C-H alkylation data presented in FIG. 2B.

| Variant | [P411], µM | TTN ± SD | e.r. |
|---|---|---|---|
| P-4 A82L | 4.0 | 14 ± 2 | N.A. |
| P-4 A82L F263Y | 4.0 | 29 ± 1 | N.A. |
| P-4 A82L F263Y A78L | 4.0 | 23 ± 5 | N.A. |
| P411-gen4 | 2.0 | 48 ± 3 | N.A. |
| P411-gen5 | 2.0 | 68 ± 3 | N.A. |
| P411-gen6 | 2.0 | 59 ± 4 | rac |
| P411-gen6b | 2.0 | 98 ± 2 | rac |
| P411-gen7 | 2.0 | 200 ± 4 | 55.0:45.0 |
| P411-gen8 | 2.0 | 560 ± 50 | 59.4:40.6 |
| P411-gen9 | 2.0 | 940 ± 30 | 64.7:35.3 |
| P411-gen10 | 2.0 | 1480 ± 50 | 68.1:31.9 |
| P411-gen11 | 2.0 | 1240 ± 30 | 77.9:22.1 |
| P411-gen12 | 2.0 | 1490 ± 40 | 88.5:11.5 |
| P411-gen13 | 2.0 | 1960 ± 40 | 94.0:6.0 |
| P411-CHF | 2.0 | 2020 ± 40 | 96.7:3.3 |

TABLE 8

Enzymatic C-H alkylation data presented in FIG. 2C.

| Variant | [P411], µM | TTN ± SD | e.r. |
|---|---|---|---|
| P-4 A82L | 4.0 | 2 ± 0 | N.A. |
| P-4 A82L F263Y | 4.0 | 4 ± 0 | N.A. |
| P-4 A82L F263Y A78L | 4.0 | 7 ± 2 | N.A. |
| P411-gen4 | 2.0 | 13 ± 1 | N.A. |
| P411-gen5 | 2.0 | 14 ± 0 | N.A. |
| P411-gen6 | 2.0 | 12 ± 1 | N.A. |
| P411-gen6b | 2.0 | 18 ± 1 | N.A. |
| P411-gen7 | 2.0 | 34 ± 1 | N.A. |
| P411-gen8 | 2.0 | 130 ± 20 | 67.7:32.3 |
| P411-gen9 | 2.0 | 260 ± 20 | 71.9:28.1 |
| P411-gen10 | 2.0 | 510 ± 30 | 76.9:23.1 |
| P411-gen11 | 2.0 | 450 ± 10 | 83.0:17.0 |
| P411-gen12 | 2.0 | 630 ± 20 | 92.0:8.0 |
| P411-gen13 | 2.0 | 500 ± 30 | 96.9:3.1 |
| P411-CHF | 2.0 | 440 ± 30 | 98.0:2.0 |

Five rounds of mutagenesis and screening yielded variant P411-gen6, which furnished product 3a with 60 TTN. Unlike the native monooxygenase activity, the C—H alkylation process does not require reducing equivalents from the FAD and FMN domains of the enzyme. It was surmised that these domains may not be needed for the C—H alkylation reaction, and systematic truncations of P411-gen6 were performed to determine the minimally sufficient domain(s) for retaining catalytic activity. Curiously, removal of the FAD domain, containing 37% of the amino acids in the full-length protein, created an enzyme with higher C—H alkylation activity: P411ΔFAD-gen6 delivers 3a with 100 TTN, a 1.7-fold increase in TTN compared with P411-gen6

(FIG. 3). This indicates that the FAD domain may have (negative) allosteric effects on C—H alkylation activity. Further studies with these truncated enzymes revealed that they could be used in whole *E. coli* cells, in clarified *E. coli* cell lysate, and as purified proteins (Table 9).

TABLE 9

P411-gen9, an evolved P411 C-H alkylation enzyme, is active in whole *E. coli* cells, in clarified *E. coli* lysate, and as a purified protein.

| Form | [P411], µM | Exogenous reductant | TTN to 3a |
|---|---|---|---|
| whole *E. coli* cells (OD600 = 15-17) | 2.0 µM | None | 900 |
| Lysate | 2.0 µM | Na2S2O4, 1 mM | 940 |
| Purified protein | 11.9 µM | Na2S2O4, 1 mM | 150 |
| Purified protein | 11.9 µM | Na2S2O4, 5 mM | 210 |
| Purified protein | 10.0 µM-11.9 µM | NADPH, 10 mM | 250 |

Eight additional rounds of mutagenesis and screening, as summarized in Table 7 and Table 8, yielded "P411-CHF" (P411ΔFAD C—H Functionalization enzyme) having the amino acid sequence set forth in SEQ ID NO:3. P411-CHF displays 140-fold improvement in activity over P-4 A82L and delivers 3a with excellent stereoselectivity (2020 TTN, 96.7:3.3 e.r. using clarified *E. coli* lysate). Subsequent studies showed that the stereoselectivity could be improved by conducting the reaction at lower temperature (e.g., 4° C.) with no significant change to TTN (Table 10). Enzymatic C—H alkylation can be performed on millimole scale: using 1.0 mmol alkane 1a, *E. coli* harboring P411-CHF at 4° C. furnished 3a in 82% isolated yield, 1060 TTN, and 98.0:2.0 e.r. (FIG. 2B).

TABLE 10

Enzymatic C-H alkylation reactions performed using *E. coli* cells harboring P411-CHF under non-standard conditions.

| Conditions | TTN to 3a | e.r. |
|---|---|---|
| Anaerobic, full system, room temp. | 2150 | 96.7:3.3 |
| Anaerobic, full system, 4° C. | 2090 | 98.0:2.0 |
| Anaerobic, no GOX, room temp. | 2100 | 96.7:3.3 |
| Anaerobic, no GOX, no D-glucose, room temp. | 1770 | 96.7:3.3 |
| Aerobic, no GOX, no D-glucose, room temp. | 30 | not measured |

Example 3

Mechanistic Investigations of Enzyme Catalyzed C—H Insertion Reactions

Preliminary mechanistic investigations were pursued to interrogate the nature of the C—H insertion step. Independent initial rates measured for reactions with alkane 1a or deuterated alkane 1a-d2 revealed a normal kinetic isotope effect (KIE) of 5.1 for C—H alkylation catalyzed by P411-CHF, suggesting that C—H insertion is rate-determining (FIG. 4). Data points in FIG. 4 represent an average of duplicate measurements; error bars represent one standard deviation. Data collected at the 10-minute time point using alkane 1a-d2 were excluded due to non-linear behavior.

Initial rates were measured from independent reactions set up in parallel using clarified lysate of *E. coli* cells overexpressing P411-CHF. The concentration of P411-CHF was normalized to be 2.0 µM in each reaction. A modified version of the procedure for reactions with lysate was followed. The modification was as follows: after combining all components of the reaction mixture except the alkane and diazo substrates, the 2 mL reaction vial was allowed to shake in the anaerobic chamber at 500 rpm for at least 10 minutes to ensure even mixing. Reaction vials were then charged with alkane (10 µL, 400 mM in EtOH) and ethyl diazoacetate (10 µL, 400 mM in EtOH) and shaken at 500 rpm, room temp. Final concentrations were 2.0 µM P411-CHF, 1 mM $Na_2S_2O_4$, 10 mM alkane, 10 mM ethyl diazoacetate, and 25 mM D-glucose. Reactions were set up in duplicate and products quantified at 1-minute intervals by quenching with acetonitrile (400 µL) and internal standard (10 µL, 60 mM ethyl phenoxyacetate in MeCN). This mixture was then removed from the anaerobic chamber, transferred to a microcentrifuge tube, and centrifuged (20,000×g, 10 minutes). The supernatant was transferred to a vial and analyzed by HPLC). Turnover number was calculated by dividing the concentration of product (mM) by concentration of P411-CHF (0.002 mM).

Independent rate experiments with P411-CHF show an intermolecular kinetic isotope effect (KIE, kH/kD) of 5.1. This suggests that C—H insertion is rate-determining and could possibly involve a linear transition state. In contrast, kinetic isotope effects for rhodium catalysts with carboxylate ligands are significantly less (KIE=1.55–3.2); this has been invoked as evidence to support a widely accepted three-centered transition state for C—H insertion with these systems=. See, Demonceau, et al. *J. Mol. Catal.* 58, 21-26 (1990); Davies, et al. *J. Am. Chem. Soc.* 122, 3063-3070 (2000); Doyle, et al. *J. Am. Chem. Soc.* 115, 958-964 (1993). The difference in KIE between P411-CHF and the rhodium-carboxylate catalysts suggests that these systems may have different transitions states or different mechanisms for the C—H insertion step. Since the nature of the C—H insertion step could influence the substrate and product profiles of the catalyst, this is one strong motivation to develop diverse systems for this chemistry.

Example 3

Substrate Synthesis and Characterization

Commercially available alkane and diazo substrates were used as received: 1a, 1d, 1f, 1g, 1m, 7a, 7c-7f, 9a, 9e, 9f (custom synthesis, Arch Bioscience). Compound 1c was also commercial (Combi-Blocks), though the commercial product was used only for synthesis. Ethyl diazoacetate (2, Sigma-Aldrich) was concentrated under reduced pressure and its concentration relative to residual dichloromethane was determined by $^1$H NMR. Diazo compounds 9h and 9i are known and were prepared according to literature procedures. Caution: although no safety issues were encountered, diazo compounds are reactive and should be used with caution.

General Procedure A: Methylation of alcohols. To a 250 mL round bottom flask was added NaH (60% dispersion in mineral oil, 15-30 mmol, 1.2-1.5 equiv.). The flask was evacuated and filled with argon (3 times). Anhydrous THF (45-80 mL) was added by syringe and the reaction mixture was cooled to 0° C. in an ice bath. Alcohol (10-20 mmol, 1.0 equiv.) in THF (5-10 mL) was added dropwise and the reaction mixture was allowed to warm to room temperature and stirred for 30 minutes. Following, iodomethane (20-40 mmol, 2.0 equiv.) in THF (10 mL) was added and the reaction was stirred at room temperature (8-15 hours). The reaction was quenched by the addition of brine (60 mL) or NH₄Cl (sat. aq., 60 mL) and the phases were separated. The aqueous layer was extracted with diethyl ether (3×60 mL); the combined organics were washed with aq. sodium thiosulfate (10% w/v, 50 mL, when necessary), dried over Na₂SO₄ and concentrated under reduced pressure. Purification by silica column chromatography with hexanes/ethyl acetate or pentane/diethyl ether afforded compounds the desired products in 37-99% yield.

1-Methoxy-4-(methoxymethyl-d₂)benzene (1a-d₂)

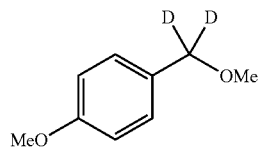 [SMILES: [2H]C([2H])(OC)c1ccc(OC)cc1]

Labeled substrate 1a-d₂ was prepared from methyl 4-methoxybenzoate using a two-step sequence to 98% deuterium incorporation at the benzylic position. First, to a dry round bottom flask, under argon, was added LiAlD4 (0.23 g, 5.5 mmol, 1.1 equiv.) and anhydrous Et₂O (10 mL). A solution of methyl 4-methoxybenzoate (0.83 g, 5 mmol, 1.0 equiv.) in dry Et₂O (5 mL) was added dropwise and the reaction was allowed to stir at room temperature for 12 hours. Following, the reaction mixture was cooled to 0° C. and diluted with Et₂O. The reaction was quenched by the addition of 0.2 mL H₂O, 0.2 mL NaOH (aq., 1M), and 0.6 mL H₂O. The mixture was allowed to warm to room temperature and stirred for 15 minutes. MgSO₄ was added and the mixture was stirred for a further 15 minutes, filtered, and concentrated under reduced pressure. The crude product was purified by silica column chromatography with hexanes/ethyl acetate to give (4-methoxyphenyl)methanol-d₂ (0.43 g, 61% yield, 98% deuterium incorporation), with spectral data in agreement with literature report. Methylation of this compound was performed following General Procedure A (note: reaction performed on 3.0 mmol scale) to afford 1a-d₂ (0.43 g, 61% yield, 98% deuterium incorporation).

¹H NMR (400 MHz, CDCl₃) δ 7.27 (d, J=8.4 Hz, 2H), 6.90 (d, J=8.5 Hz, 2H), 3.81 (s, 3H), 3.36 (s, 3H). ¹³C NMR (101 MHz, CDCl₃) δ 159.3, 130.3, 129.5, 113.9, 73.7 (m, labeled), 57.8, 55.4. HRMS (EI) m/z: 154.0964 (M⁺⁺); calc. for C₉H₁₀O₂²H₂: 154.0963.

1-(Methoxymethyl)-4-methylbenzene (1b)

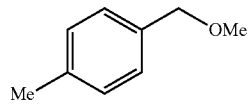

Prepared from p-tolylmethanol using General Procedure A. ¹H NMR (400 MHz, CDCl₃) δ 7.23 (d, J=8.0 Hz, 2H), 7.17 (d, J=7.9 Hz, 2H), 4.43 (s, 2H), 3.37 (s, 3H), 2.35 (s, 3H).

1-Bromo-4-(methoxymethyl)benzene (1c)

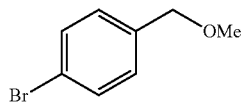

Prepared from (4-bromophenyl)methanol using General Procedure A. ¹H NMR (400 MHz, CDCl₃) δ 7.47 (d, J=8.4 Hz, 2H), 7.21 (d, J=8.6 Hz, 2H), 4.41 (s, 2H), 3.38 (s, 3H).

1-(Methoxymethyl)-3-methylbenzene (1e)

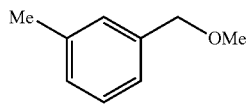

Prepared from m-tolylmethanol using General Procedure A. ¹H NMR (400 MHz, CDCl₃) δ 7.28-7.21 (m, 1H), 7.19-7.08 (m, 3H), 4.43 (s, 2H), 3.40 (s, 3H), 2.36 (s, 3H). ¹³C NMR (101 MHz, CDCl₃) δ 138.2, 128.6, 128.5, 128.4, 124.9, 74.9, 58.3, 21.5. HRMS (FAB) m/z: 135.0810 [(M+H⁺)—H₂]; calc. for C₉H₁₁O: 135.0810.

(4-(Methoxymethyl)phenyl)dimethylsilane (1h)

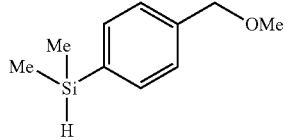 [SMILES: COCc1ccc([SiH](C)C)cc1]

In a 250 mL round bottom flask, under argon, 1-bromo-4-(methoxymethyl)benzene (3.0 g, 15 mmol, 1.0 equiv.) in anhydrous THF (60 mL) was cooled to −78° C. A solution of n-butyllithium (9 mL, 2.5 M in hexanes, 22.5 mmol, 1.5 equiv.) was added dropwise. The resulting mixture was stirred at −78° C. for 2 hours before the dropwise addition of chlorodimethylsilane (2.4 mL, 22.5 mmol, 1.5 equiv.). The reaction was allowed to warm to room temperature and stirred overnight. The reaction mixture was cooled to 0° C. and quenched with NH₄Cl (sat. aq., 20 mL). The aqueous layer was extracted with diethyl ether (3×30 mL); the combined organics were washed with brine (30 mL), dried over Na₂SO₄ and concentrated under reduced pressure. The crude reaction mixture was purified by silica column chromatography with hexanes/ethyl acetate to afford 1h (2.14 g, 79% yield). A second round of purification by silica column chromatography with hexanes/ether was performed on a portion of the product.

¹H NMR (400 MHz, CDCl₃) δ 7.54 (d, J=8.1 Hz, 2H), 7.35 (d, J=8.1 Hz, 2H), 4.47 (s, 2H), 4.43 (hept, J=3.7 Hz, 1H), 3.40 (s, 3H), 0.35 (d, J=3.7 Hz, 6H). ¹³C NMR (101 MHz, CDCl₃) δ 139.3, 136.9, 134.3, 127.3, 74.7, 58.3, −3.6. HRMS (FAB) m/z: 179.0894 [(M+H⁺)—H₂]; calc. for C₁₀H₁₅OSi: 179.0892.

1-Ethyl-4-isopropylbenzene (1l)

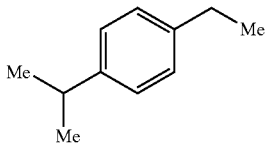 [SMILES: CCc1ccc(C(C)C)cc1]

The following procedure was modified from the literature. To a 250 mL round bottom flask were added Pd/C (10% Pd on activated charcoal, 486 mg, 20% w/w), 4-isopropylacetophenone (2.43 g, 15 mmol), and methanol (60 mL). The solution was sparged with $H_2$ and stirred under 1 atm $H_2$ for 48 hours; monitoring the mixture by TLC showed that that the reaction did not go to completion under these conditions. The crude reaction mixture was filtered through a pad of Celite, dried over dried over $Na_2SO_4$, and concentrated under reduced pressure. Purification by silica column chromatography with hexanes afforded product 1l (218 mg, 1.47 mmol, 10% yield).

$^1$H NMR (500 MHz, $CDCl_3$) δ 7.19-7.13 (m, 4H), 2.90 (hept, J=6.9 Hz, 1H), 2.65 (q, J=7.6 Hz, 2H), 1.29-1.24 (m, 9H). $^{13}$C NMR (126 MHz, $CDCl_3$) δ 146.2, 141.7, 127.9, 126.5, 33.8, 28.5, 24.2, 15.7. HRMS (FAB) m/z: 149.1327 (M+H$^+$); calc. for $C_{11}H_{17}$: 149.1330.

(E)-1-Methoxyoct-2-ene (4a)

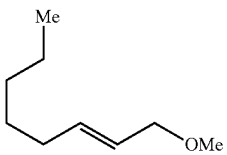

Prepared from (E)-oct-2-en-1-ol using General Procedure A. $^1$H NMR (400 MHz, $CDCl_3$) δ 5.70 (dtt, J=15.6, 6.6, 1.2 Hz, 1H), 5.54 (dtt, J=15.3, 6.2, 1.4 Hz, 1H), 3.86 (dq, J=6.2, 1.0 Hz, 2H), 3.31 (s, 3H), 2.08-1.99 (m, 2H), 1.43-1.34 (m, 2H), 1.34-1.21 (m, 4H), 0.88 (t, J=7.0 Hz, 3H). $^{13}$C NMR (101 MHz, $CDCl_3$) δ 135.2, 126.1, 73.5, 57.8, 32.4, 31.5, 28.9, 22.7, 14.2.

(E)-1-Methoxyhex-2-ene (4b)

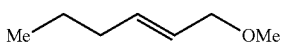

Prepared from (E)-hex-2-en-1-ol using a modified version of General Procedure A. To a 100 mL dry round bottom flask, cooled under argon, were added (E)-hex-2-en-1-ol (2.0 g, 20 mmol, 1.0 equiv.), DMF (35 mL), and iodomethane (5.7 g, 40 mmol, 2.0 equiv.). The resulting solution was cooled to 0° C. and NaH (60% dispersion in mineral oil, 960 mg, 24 mmol, 1.2 equiv.) was added portion-wise. The mixture was stirred at 0° C. for 30 minutes, then allowed to warm to room temperature and stirred for an additional 3 hours. The reaction mixture was cooled to 0° C., quenched with the addition of $NH_4Cl$ (sat. aq., 30 mL), and diluted with diethyl ether (50 mL). Phases were separated and the aqueous layer was extracted with diethyl ether (3×50 mL). The combined organics were washed with $H_2O$ (2×25 mL) and brine (25 mL), dried over $Na_2SO_4$, and concentrated under reduced pressure (≥200 mbar). Purification by silica column chromatography with pentane/diethyl ether afforded compound 4b (746 mg, 6.5 mmol, 33% yield).

$^1$H NMR (500 MHz, $CDCl_3$) δ 5.70 (dtt, J=15.4, 6.6, 1.2 Hz, 1H), 5.55 (dtt, J=15.4, 6.3, 1.4 Hz, 1H), 3.87 (dq, J=6.3, 1.1 Hz, 2H), 3.32 (s, 3H), 2.06-2.00 (m, 2H), 1.42 (app. sext, J=7.4 Hz, 2H), 0.91 (t, J=7.3 Hz, 3H). $^{13}$C NMR (126 MHz, $CDCl_3$) δ 134.9, 126.3, 73.4, 57.8, 34.5, 22.4, 13.8.

(E)-7-Bromo-1-methoxyhept-2-ene (4c)

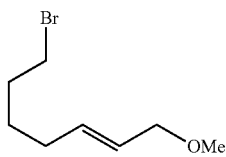

To a 100 mL flamed dried flask was added Grubbs' catalyst 2$^{nd}$ generation (85 mg, 1 mol %). The flask was then evacuated and backfilled with argon for three times. Under argon, a dry $CH_2Cl_2$ solution containing 6-bromo-1-hexene (1.63 g, 10 mmol, 1.0 equiv.) and crotonaldehyde (3.50 g, 50 mmol, 5.0 equiv.) was added to the flask. The mixture was stirred under reflux for 20 hours and then cooled to room temperature and filtered through a silica plug. The solvent was removed under reduced pressure and the crude product was purified by flash chromatography (hexanes/ethyl acetate) to give (E)-7-bromohept-2-enal (1.6 g, 84% yield). This product was then dissolved in 10 mL dry THF and then added slowly to a suspension of $NaBH_4$ (375 mg, 10 mmol, 1.0 equiv.) in dry THF (10 mL) at 0° C. To this reaction mixture, iodine (1.27 g, 5 mmol, 0.5 equiv.) in 10 mL of THF was slowly added at 0° C. Reaction was stirred until the aldehyde was fully reduced as indicated by TLC. The reaction was quenched with $NH_4Cl$ (sat. aq.), the phases were separated, and the aqueous phase was extracted with ethyl acetate (3×20 mL). The combined organic layers were washed with brine and dried over $Na_2SO_4$. The solvent was removed under reduced pressure and the crude alcohol product was used directly without purification. General Procedure A was used for the methylation step and the final product 4c was obtained with 50% overall yield (1.03 g, 5 mmol).

$^1$H NMR (400 MHz, $CDCl_3$) δ 5.68 (dtt, J=15.3, 6.4, 1.1 Hz, 1H), 5.57 (dtt, J=15.4, 6.0, 1.2 Hz, 1H), 3.86 (dq, J=5.9, 1.0 Hz, 2H), 3.41 (t, J=6.8 Hz, 2H), 3.32 (s, 3H), 2.14-2.05 (m, 2H), 1.92-1.82 (m, 2H), 1.57-1.49 (m, 2H). $^{13}$C NMR (101 MHz, $CDCl_3$) δ 133.9, 127.0, 73.3, 57.9, 33.8, 32.3, 31.5, 27.7. HRMS (EI) m/z: 205.0216 (M–H$^+$); calc. for $C_8H_{14}{}^{79}BrO$: 205.0228.

(E)-1-(But-1-en-1-yl)-4-methoxybenzene (4d)

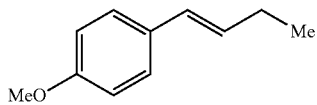 [SMILES: CC/C=C/c1ccc(OC)cc1]

This compound was accessed in a two-step sequence. First, to propyltriphenylphosphonium bromide (7.6 g, 19.7 mmol, 1.0 equiv.) suspended in anhydrous THF (70 mL) and cooled to 0° C. was added n-butyllithium (2.5 M in hexanes, 7.9 mL, 19.7 mmol, 1.0 equiv.) dropwise over 10 min to form a bright orange solution. After stirring for 1 hour, 4-methoxybenzaldehyde (2.7 g, 19.7 mmol, 1.0 equiv.) was added dropwise over 5 min. The reaction mixture was allowed to slowly warm to room temperature and stirred at room temperature overnight. The reaction mixture was diluted with pentane (50 mL) and the resulting solution was washed with HCl (aq., 0.1 M, 50 mL), $H_2O$ (50 mL), $NaHCO_3$ (sat. aq., 50 mL), and brine (50 mL). The organics were dried over sodium sulfate and concentrated under reduced pressure. The crude product was purified by silica column chromatography with pentane/diethyl ether to afford (E:Z)-4d (2:1 E:Z, 2.50 g, 15.4 mmol, 78% yield).

Next, (E:Z)-4d was isomerized following a literature method. To a dry 25 mL round bottom flask, under argon, were added (E:Z)-4d (300 mg, 1.85 mmol), $(MeCN)_2PdCl_2$ (235 mg, 50 mol %), and 4 mL anhydrous dichloromethane. The resulting mixture was stirred at room temperature for 24 hours. The crude reaction mixture was filtered through Celite and concentrated under reduced pressure. Purification by silica column chromatography using hexanes/diethyl ether delivered 4d (>20:1 E:Z, 279 mg, 1.72 mmol, 93% yield).

$^1$H NMR (400 MHz, $CDCl_3$) δ 7.28 (d, J=8.7 Hz, 2H), 6.85 (d, J=8.8 Hz, 2H), 6.33 (dt, J=15.7, 1.6 Hz, 1H), 6.13 (dt, J=15.8, 6.5 Hz, 1H), 3.80 (s, 3H), 2.26-2.16 (m, 2H), 1.08 (t, J=7.5 Hz, 3H). $^{13}$C NMR (101 MHz, $CDCl_3$) δ 158.7, 130.9, 130.7, 128.2, 127.1, 114.0, 55.4, 26.2, 14.0.

1-Methoxyoct-2-yne (4e)

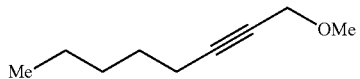

To a solution of 3-methoxyprop-1-yne (845 μL, 10 mmol, 1.0 equiv.) in anhydrous THF (50 mL) at −20° C., was added n-butyllithium (2 M in THF, 6 mL, 12 mmol, 1.2 equiv.) and HMPA (869 μL, 5 mmol, 0.5 equiv.) dropwise over 5 min. The resulting mixture was stirred at −20° C. for 3 hours before the addition of 1-iodopentane (1.96 mL, 15 mmol, 1.5 equiv.). The reaction was allowed to slowly warm to room temperature in 2 hours and stirred for additional 18 hours. The reaction was then quenched by $NH_4Cl$ (sat. aq., 20 mL) and $H_2O$ (30 mL), and extracted by diethyl ether (40 mL×3). The combined organic layer was washed by $H_2O$ (50 mL) and brine (50 mL), and then dried over sodium sulfate and concentrated under reduced pressure. The crude product was purified by silica column chromatography with pentane/diethyl ether to afford 4e (1.04 g, 7.4 mmol, 74% yield).

$^1$H NMR (400 MHz, $CDCl_3$) δ 4.07 (t, J=2.2 Hz, 2H), 3.37 (s, 3H), 2.22 (tt, J=7.2, 2.2 Hz, 2H), 1.56-1.47 (m, 2H), 1.41-1.26 (m, 4H), 0.89 (t, J=7.1 Hz, 3H). NMR (101 MHz, $CDCl_3$) δ 87.4, 75.8, 60.4, 57.5, 31.2, 28.5, 22.3, 18.9, 14.1. HRMS (EI) m/z: 139.1128 [(M−H·)+]; calc. for $C_9H_{15}O$: 139.1123.

4-Ethyl-N,N-dimethylaniline (7b)

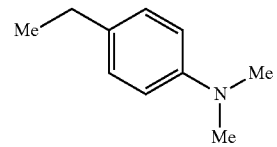 [SMILES: CCc1ccc(N(C)C)cc1]

4-Ethylaniline (0.605 g, 5 mmol, 1.0 equiv.) and formaldehyde (1.8 mL, 50 mmol, 10.0 equiv.) were mixed in acetic acid (30 mL). The solution was stirred for 30 min at 0° C. before portionwise addition of $NaBH_3CN$ (1.57 g, 25 mmol, 5.0 equiv.). After the reaction was stirred overnight, NaOH (aq., 2M) was used to neutralize the reaction at 0° C. until pH 8-10. The crude product was extracted with diethyl ether (30 mL×3). The combined organic layer was washed with $H_2O$ (50 mL) and brine (50 mL), and then dried over sodium sulfate and concentrated under reduced pressure. The crude product was purified by silica column chromatography with hexanes/ethyl acetate to afford 7b (635 mg, 4.25 mmol, 85% yield).

$^1$H NMR (400 MHz, $CDCl_3$) δ 7.09 (d, J=8.8 Hz, 2H), 6.72 (d, J=8.7 Hz, 2H), 2.92 (s, 6H), 2.57 (q, J=7.6 Hz, 2H), 1.21 (t, J=7.6 Hz, 3H). $^{13}$C NMR (101 MHz, $CDCl_3$) δ 149.1, 132.8, 128.5, 113.3, 41.2, 27.9, 16.1.

3-Diazodihydrofuran-2(3H)-one (9b)

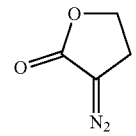

The preparation of the title compound 9b followed a modified procedure reported by Sattely et al. Sodium azide (4.83 g, 74.3 mmol, 4 equiv.), sodium hydroxide (80 mL of 2 M in water, 160 mmol), tetrabutylammonium bromide (60.0 mg, 0.190 mmol, 0.01 equiv.), and hexane (80 mL) were combined in a 500-mL flask with magnetic stir bar open to the air and cooled to 0° C. With vigorous stirring, triflic anhydride (6.20 mL, 37.1 mmol, 2 equiv.) was added dropwise. After 15 min, a solution of 2-acetyl-butyrolactone (2.00 mL, 18.6 mmol) in acetonitrile (70 mL) was poured into the vessel through a funnel, followed by an additional 10 mL of acetonitrile to complete the transfer. The initially colorless reaction mixture immediately turned yellow. After stirring for 20 min at 0° C., the mixture was diluted with ice water (50 mL) and chilled EtOAc (50 mL) and transferred to a separatory funnel. After phase separation and removal of the organic fraction, the aqueous layer was washed with chilled EtOAc (50 mL×5). The combined organic layer was dried over $Na_2SO_4$, filtered, and concentrated under reduced pressure. The resulting crude product was purified by silica column chromatography with hexanes/ethyl acetate as eluents. The yellow-colored fractions were concentrated to afford the product as a bright yellow crystalline solid (1.2-1.6 g, 60-75% yield). Spectral data are consistent with Sattely et al.

2-Diazo-N-methoxy-N-methylacetamide (9c)

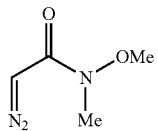

4-Methylbenzenesulfonohydrazide (9.31 g, 50 mmol, 1.0 equiv.) was dissolved in aqueous hydrochloric acid (2 M, 30 mL) and warmed to 50° C. (solution 1). 2-Oxoacetic acid (7.40 g of 50% in water, 50 mmol, 1.0 equiv.) was dissolved in water (100 mL) and heated to 50° C. (solution 2). Pre-warmed solution 1 was slowly transferred to solution 2. The reaction mixture was then stirred at 60° C. for 4 h until all the hydrozone product crashed out. The mixture was cooled to 0° C. and kept for 2 h. The product 2-(2-tosylhydrazineylidene)acetic acid (9.88 g, 82% yield) was collected by filtration, washed with hexane: ethyl acetate (10:1) and dried under vaccum.

2-(2-Tosylhydrazineylidene)acetic acid (4.84 g, 20 mmol, 1.0 equiv.) was dissolved in dry dichloromethane (30 mL). Thionyl chloride (16 mL) and N,N-dimethyl formaldehyde (3 drops, cat.) were added to the solution. The reaction mixture was stirred at room temperature for 1 h and then heated to reflux (~50° C.) for 5 h until the starting material was completely dissolved and the reaction turned clear and light yellow. After the reaction was cooled to room temperature, organic solvent and the excess thionyl chloride was removed under reduced pressure. The resulting mixture (solid) was then dissolved in dry dichloromethane (20 mL) and used for the next step.

N,O-Dimethylhydroxylamine hydrochloride (3.91 g, 40 mmol, 2.0 equiv.) and triethylamine (11.2 mL, 80 mmol, 4.0 equiv.) were mixed in dry dichloromethane (80 mL) and stirred for 30 min. The solution of acyl chloride was added dropwise over 20 min to the reaction mixture at 0° C. The reaction was then stirred at room temperature for 5 h before water (80 mL) was added to quench the reaction. The liquid phases were transferred to a separatory funnel, and the aqueous phase was extracted with dichloromethane (50 mL×4). The combined organic phase was washed with water (40 mL) and brine (40 mL), dried over $Na_2SO_4$, filtered, and concentrated under reduced pressure. The resulting crude product was purified by silica column chromatography with hexanes/ethyl acetate to afford 9c as a yellow liquid (0.82 g, 32% yield).

$^1$H NMR (400 MHz, $CDCl_3$) δ 5.33 (s, 1H), 3.66 (s, 3H), 3.19 (s, 3H).

1-Diazopropan-2-one (9d)

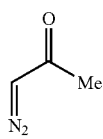

The preparation of the title compound 9d followed a modified procedure reported by Zhang et al. To a solution of acetylacetone (3.4 mL, 33.0 mmol, 1.10 equiv.) and triethylamine (5.04 mL, 36.4 mmol, 1.21 equiv.) in dry acetonitrile (25 mL), a solution of p-acetamidobenzenesulfonyl azide (7.20 g, 30.0 mmol, 1.0 equiv.) in dry acetonitrile (25 mL) was added dropwise. The reaction mixture was stirred at room temperature for 4 h. Then, the solvent was removed under reduced pressure and the resulting mixture was then purified by silica column chromatography with hexanes/ethyl acetate to give 3-diazopentane-2,4-dione (3.65 g, 96% yield) as a pale yellow liquid.

3-Diazopentane-2,4-dione (1.89 g, 15 mmol, 1.0 equiv.) was dissolved in diethyl ether (25 mL). An aqueous solution (25 mL) of NaOH (3.00 g, 75 mmol, 5.0 equiv.) was added dropwise over 10 min to the ether layer with vigorous stirring at 0° C. The reaction mixture turned dark brown within 20 min and was then stirred at room temperature for 4 h. The liquid phases were transferred to a separatory funnel, and the aqueous phase was extracted with diethyl ether (30 mL×5). The combined organic phase was dried over $Na_2SO_4$, filtered, and concentrated under reduced pressure (T=24° C., P≥20 kPa) to give product 9d as a volatile yellow liquid (0.892 g, 71% yield). Spectral data is consistent with Zhang et al.

Ethyl 2-diazobutanoate (9g)

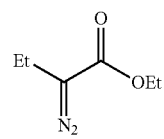

The preparation of the title compound 9g followed a modified procedure reported by Huang et al. To a solution of ethyl 2-ethylacetoacetate (3.16 g, 20.0 mmol, 1.0 equiv.) and p-acetamidobenzenesulfonyl azide (7.21 g, 30.0 mmol, 1.5 equiv.) in dry acetonitrile (50 mL) was added 1,8-diazabicyclo[5.4.0]undec-7-ene (DBU, 4.5 mL, 30.0 mmol, 1.5 equiv.) dropwise at 0° C. The reaction mixture was stirred at 0° C. for 1 h and at room temperature for 2 h. Water (50 mL) was added to quench the reaction. Acetonitrile was removed under reduced pressure (T=24° C., P≥20 kPa). The mixture was extracted with diethyl ether (25 mL×4). The combined ether layer extract was washed with water (30 mL) and brine (30 mL), dried over $Na_2SO_4$, filtered, and concentrated under reduced pressure (T=24° C., P≥30 kPa). The crude product was purified by silica column chromatography with hexanes/ethyl acetate to give product 9g as a volatile yellow liquid (2.40 g, 84% yield). Spectral data is consistent with Huang et al.

Example 4

Study of Substrate Scope in Enzyme-Catalyzed C—H Insertion Reactions

Using *E. coli* harboring P411-CHF, a range of aromatic alkanes were assayed for coupling with ethyl diazoacetate (FIG. 5). Both electron-rich and electron-deficient functionalities on the aromatic ring are well-tolerated (3a-3e, 3h); cyclic substrates are also suitable coupling partners (3f, 3g). Functionalization of alkyl benzene-type substrates is successful at secondary benzylic sp$^3$ C—H bonds (3i-3l). Notably, in the biotransformation of substrate 11 containing both tertiary and secondary benzylic C—H bonds, P411-CHF preferentially functionalizes the secondary position despite its higher C—H bond dissociation energy (BDE). The carbene intermediate derived from ethyl diazoacetate belongs to the acceptor-only class. In contrast to the more widely-used donor/acceptor carbenes, acceptor only intermediates are more electrophilic, and as a result selective reactions with this carbene class are still a major challenge for small-molecule catalysts. The results described herein show that P411-CHF can control this highly reactive intermediate to furnish the desired $sp^3$ C—H alkylation products and do so with exceptionally high enantioselectivity.

Figure 5A:
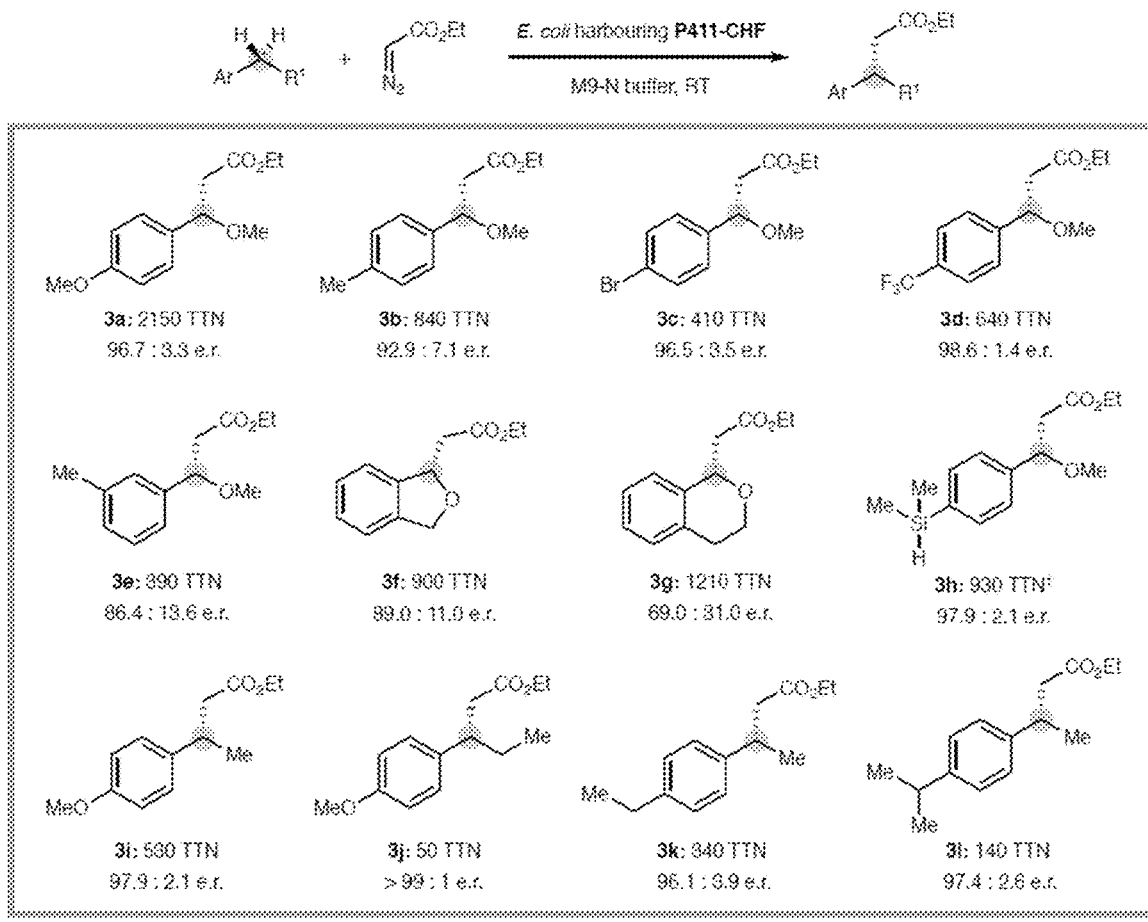
FIG. 5A shows the substrate scope for benzylic C—H alkylation with P411-CHF. Experiments were performed using *E. coli* expressing cytochrome P411-CHF (OD$_{600}$=30) with 10 mM alkane 1a-1l and 10 mM ethyl diazoacetate at room temperature (RT) under anaerobic conditions. Each reported TTN is the average of quadruplicate reactions. Si—H insertion product 3h' was also observed for reactions marked with † (see, FIG. 5D).
Figure 5B:
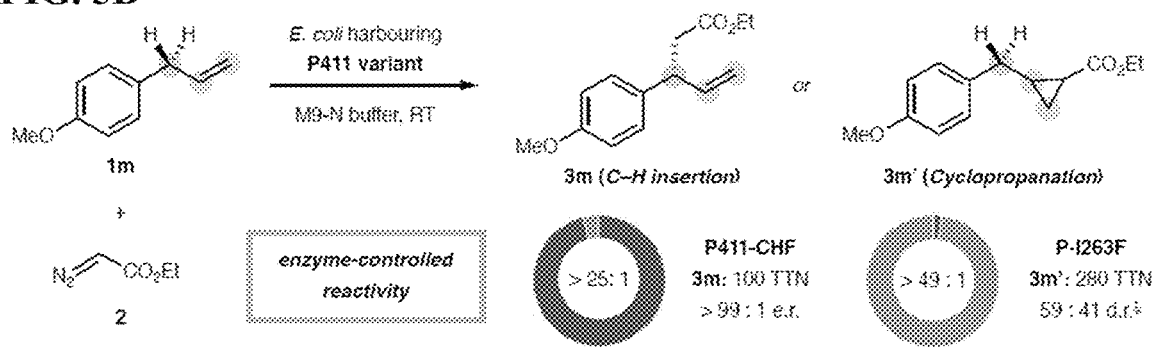
FIG. 5B shows that reaction selectivity for carbene C—H insertion or cyclopropanation can be controlled by the protein scaffold. Experiments were performed as in described for FIG. 5A using the indicated P411 variant. For the cyclopropanation product, d.r. is given as cis:trans; e.r. was not determined.
Figure 5C:
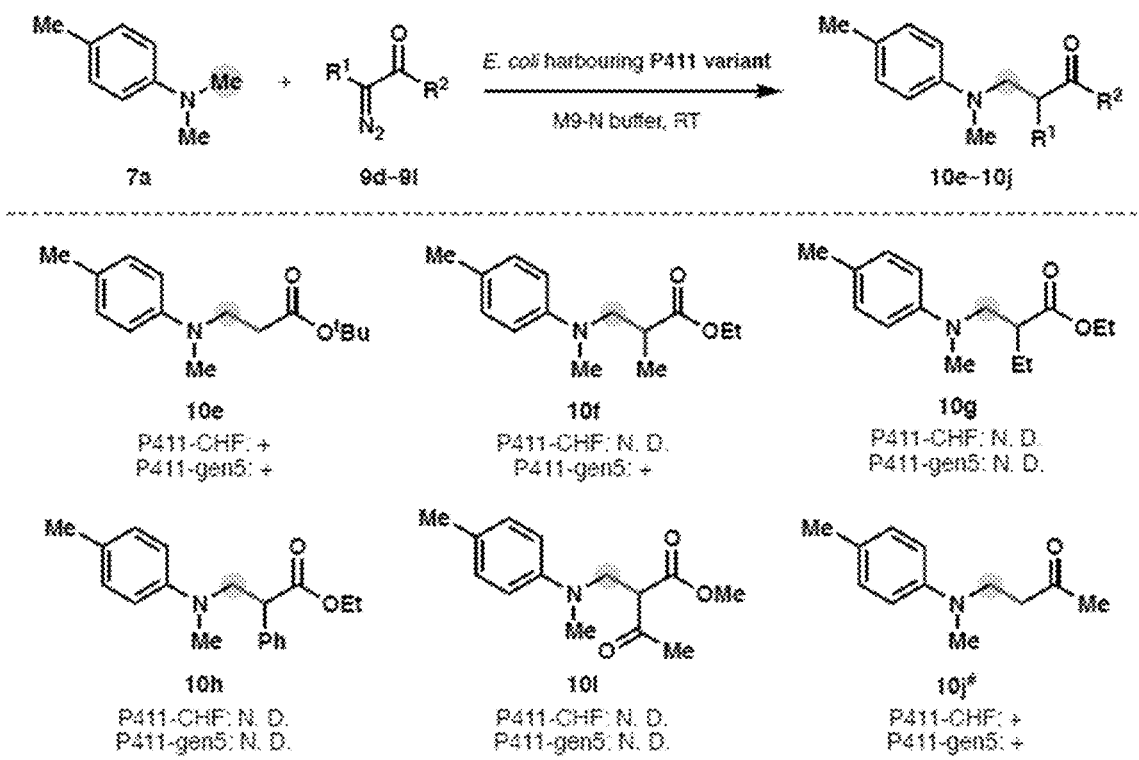
FIG. 5C shows additional diazo substrates tested with P411-CHF and P411-gen5. '+' indicates product was detected; N. D.=not detected. Other products derived from alkane 7a were also observed by GC-MS for the reaction marked with "#".
Figure 5D:
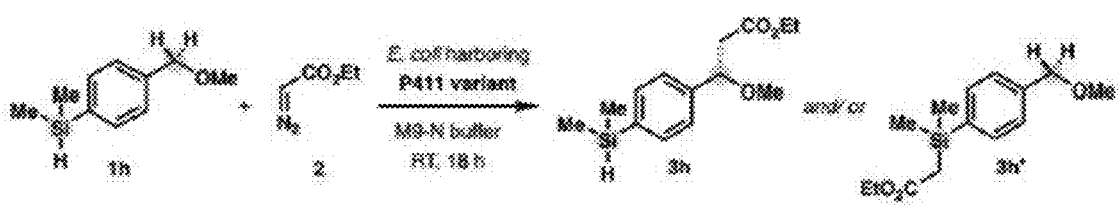
FIG. 5D shows a scheme for P411-CHF-catalyzed C—H alkylation of 1h with ethyl diazoacetate (2) to form compound 3h'.

Enzymes can exhibit excellent reaction selectivity arising from their ability to form multiple interactions with substrates and intermediates throughout a reaction cycle. It was hypothesized that the protein scaffold could be tuned to create complementary enzymes which access different reaction outcomes available to an alkane substrate. When P411-CHF was challenged with 4-allylanisole (1m), a substrate which can undergo both C—H alkylation and cyclopropanation, it was observed that the benzylic C—H alkylation product 3m dominates, with selectivity >25:1 (FIG. 5B). In contrast, a related full-length P411 variant P-I263F, containing thirteen mutations in the heme domain relative to P411-CHF, catalyzed only the formation of cyclopropane product 3m'. Additionally, despite the established reactivity of silanes with iron-carbene10, P411-CHF delivered C—H alkylation product 3h when alkane 1h was employed in the reaction (Si—H insertion product 3h' was also observed but its formation is likely catalyzed by other cellular components and not by P411-CHF). Reaction with P-I263F, in contrast, provided only the Si—H insertion product. These examples demonstrate an exceptional feature of macromolecular enzymes: different products can be obtained simply by changing the amino acid sequence of the protein catalyst.

Figure 6A:
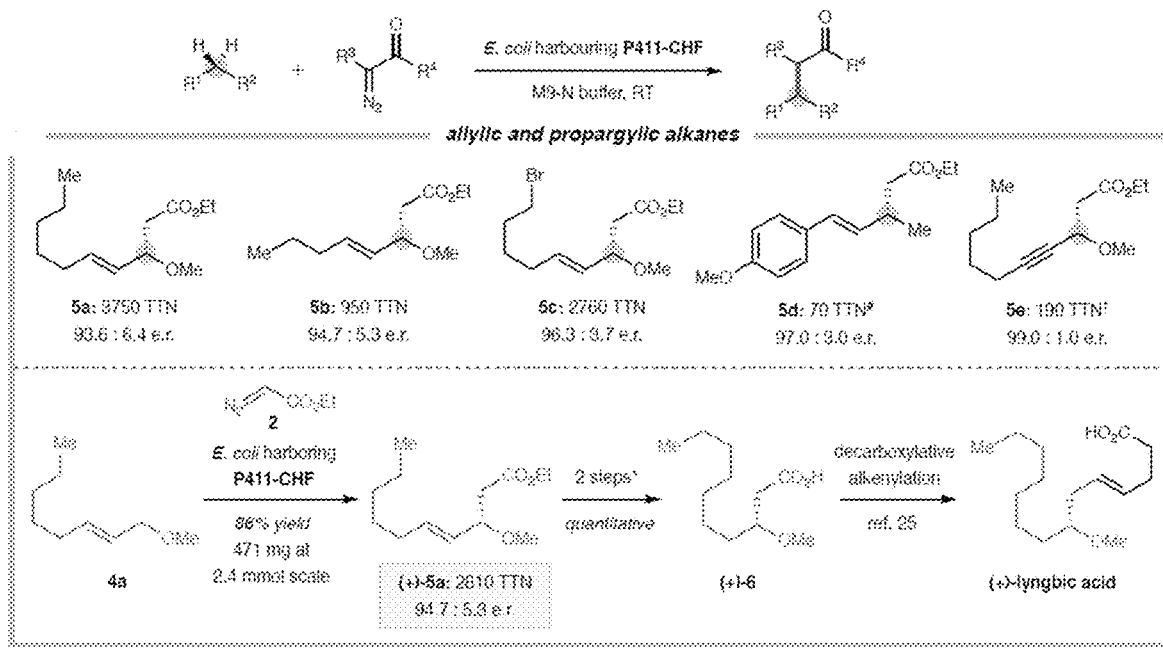
FIG. 6A shows the application of P411 enzymes for C—H alkylation. Allylic and propargylic C—H alkylation are shown. Unless otherwise indicated, experiments were performed using *E. coli* expressing cytochrome P411-CHF with 10 mM alkane 4a-4e and 10 mM ethyl diazoacetate; each reported TTN is the average of quadruplicate reactions. TTN was calculated based on isolated yield from a reaction performed at 0.25 mmol scale for reactions marked with "#." Cyclopropene product was also observed for reactions marked with "†" (see, FIG. 6D). Steps marked with "*" included hydrogenation, followed by hydrolysis.

Enzymatic C—H alkylation is not limited to functionalization of benzylic C—H bonds. Structurally dissimilar alkanes containing allylic or propargylic C—H bonds are excellent substrates for this chemistry (FIG. 6A). In contrast to alkanes 1a-1m, which contain a rigid benzene ring, substrates 4a-4c and 4e feature flexible linear alkyl chains. Their successful enantioselective alkylation suggests that the enzyme active site can accommodate substrate conformational flexibility while enforcing a favored alkane orientation relative to the carbene intermediate.

Example 5

Synthesis and Characterization of Reference Compounds

Racemic reference compounds corresponding to enzymatic products and side-products were prepared according to the following procedures. Reference compounds are characterized below.

General Procedure B: Aldol reaction and methylation synthetic sequence. In a dry 100 or 250 mL round bottom flask, under argon, a solution of diisopropylamine (6-24 mmol, 1.1-1.2 equiv.) in THF (15-30 mL) was cooled to 0° C. (General Procedure B-1) or −78° C. (General Procedure B-2). n-Butyllithium (6-25 mmol, 1.1-1.2 equiv., 1.6 or 2.5 M in hexanes) was added dropwise and the resulting mixture was stirred at the appropriate temperature for 15-30 min. The mixture was cooled to −78° C. and kept at this temperature for the remainder of the reaction. Ethyl acetate (14-28 mmol, 1.4 equiv., General Procedure B-1 or 6-10 mmol, 1.0 equiv., General Procedure B-2) was added dropwise and the mixture was stirred for an additional 30-45 min. Then, aldehyde (10-20 mmol, 1.0 equiv., General Procedure B-1 or 9-11 mmol, 1.1-1.5 equiv., General Procedure B-2) as a solution in THF (15-30 mL, General Procedure B-1) or neat (General Procedure B-2) was added slowly and the solution was stirred for a further 0.5-3 hours. The reaction mixture was quenched at −78° C. by the addition of $NH_4Cl$ (sat. aq., 10-30 mL) and allowed to thaw to room temperature. For General Procedure B-1 only, HCl (1 M aq., 1.5-3.0 mL) was also added. Phases were separated and the aqueous phase was extracted with ethyl acetate or diethyl ether (3×20-30 mL). The combined organics were washed with $NH_4Cl$ (sat. aq., 2×10-15 mL), brine (10 mL), dried over $Na_2SO_4$ and concentrated under reduced pressure. Purification by silica column chromatography with hexanes/ethyl acetate afforded the desired aldol adducts in 56-95% yield.

In the appropriate reaction vessel, aldol adduct (3-4 mmol, 1.0 equiv.), $Ag_2O$ (9-10 mmol, 2.5-3.0 equiv.), and solvent (10-15 mL) were combined, followed by iodomethane (40-60 mmol, 10-15 equiv., General Procedure B-1 or 9 mmol, 3.0 equiv., General Procedure B-2). The reaction was then stirred at the specified temperature for 24-48 hours, with additional equivalents of iodomethane (10-20 mmol, 2.5-5 equiv., General Procedure B-1) added as necessary. For General Procedure B-1, the reaction was performed in a vial equipped with a pressure release cap, toluene was employed as the solvent, and the reaction mixture was stirred at 70° C. For General Procedure B-2, diethyl ether was employed as solvent and the reaction mixture was stirred at room temperature; the reaction vessel was covered in aluminum foil to protect its contents from light. The crude mixture was filtered through a pad of Celite and concentrated under reduced pressure. Purification was performed by silica column chromatography with hexanes/ethyl acetate; if necessary, a second purification by reverse phase chromatography was performed (Biotage Isolera equipped with Biotage SNAP Ultra C18 column, water/acetonitrile eluent system). The desired products were obtained in 25-57% yield.

General Procedure C: Horner-Wadsworth-Emmons reaction and Pd/C alkene reduction synthetic sequence. In a dry round bottom flask, under argon, NaH (60% dispersion in mineral oil, 7.4-12 mmol, 1.1-2.0 equiv.) in anhydrous THF (8-23 mL) was cooled to 0° C. Triethyl phosphonoacetate (7.4-18 mmol, 1.1-3.0 equiv.) was added dropwise and the mixture was allowed to warm to room temperature and stirred for 1 hour. Ketone (5-6.7 mmol, 1.0 equiv.) in THF (2-4 mL) was added and the reaction was stirred at room temperature for 12-18 hours (for the preparation of 3j and 3l) or heated to reflux (for the preparation of 3i, 3k, 8a', and 8b'). The reaction was quenched with $NH_4Cl$ (sat. aq., 20 mL). Phases were separated and the aqueous layer was extracted with ethyl acetate (3×30 mL). The combined organics were washed with brine (10-20 mL), dried over $Na_2SO_4$, and concentrated under reduced pressure. When necessary, the crude product was purified by silica column chromatography with hexanes/ethyl acetate to afforded the desired alkene compounds in 23% to quantitative yield.

To a round bottom flask were added Pd/C (10% Pd on activated charcoal, 24-30% w/w of alkene), methanol (5-6 mL), and alkene (1.2-2.3 mmol). $H_2$ was bubbled through the solution for ~30 minutes. The reaction was stirred at room temperature under 1 atm $H_2$ until complete reduction of the alkene was observed by TLC (typically 3-8 hours). The crude product was filtered through a pad of Celite and concentrated under reduced pressure. Purification by silica column chromatography with hexanes/ethyl acetate afforded the desired products in quantitative yield.

Ethyl 3-methoxy-3-(4-methoxyphenyl)propanoate (3a)

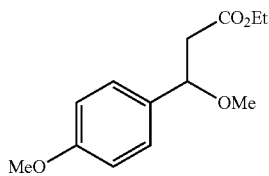 [SMILES: CCOC(=O)CC(OC)c1ccc(OC)cc1]

This compound was prepared from 4-methoxybenzaldehyde using General Procedure B-1. $^1$H NMR (400 MHz, CDCl$_3$) δ 7.25 (d, J=8.5 Hz, 2H), 6.89 (d, J=8.8 Hz, 2H), 4.58 (dd, J=9.0, 4.9 Hz, 1H), 4.14 (qd, J=7.1, 1.2 Hz, 2H), 3.81 (s, 3H), 3.19 (s, 3H), 2.80 (dd, J=15.2, 9.0 Hz, 1H), 2.55 (dd, J=15.2, 4.9 Hz, 1H), 1.23 (t, J=7.1 Hz, 3H). Spectral data are in agreement with that for the enzymatic product.

Ethyl 3-methoxy-3-(p-tolyl)propanoate (3b)

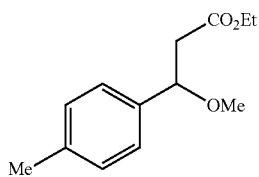 [SMILES: CCOC(=O)CC(OC)c1ccc(C)cc1]

This compound was prepared from 4-methylbenzaldehyde using General Procedure B-1. $^1$H NMR (400 MHz, CDCl$_3$) δ 7.22 (d, J=8.0 Hz, 2H), 7.16 (d, J=7.9 Hz, 2H), 4.60 (dd, J=9.2, 4.7 Hz, 1H), 4.14 (qd, J=7.1, 1.2 Hz, 2H), 3.21 (s, 3H), 2.79 (dd, J=15.3, 9.2 Hz, 1H), 2.55 (dd, J=15.3, 4.7 Hz, 1H), 2.35 (s, 3H), 1.24 (t, J=7.2 Hz, 3H). $^{13}$C NMR (101 MHz, CDCl$_3$) δ 171.2, 137.9, 137.6, 129.4, 126.7, 80.0, 60.7, 56.9, 43.7, 21.3, 14.3. HRMS (FAB) m/z: 221.1169 [(M+H$^+$)—H$_2$]; calc. for C$_{13}$H$_{17}$O$_3$: 221.1178

Ethyl 3-(4-bromophenyl)-3-methoxypropanoate (3c)

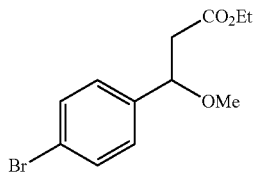 [SMILES: CCOC(=O)CC(OC)c1ccc(Br)cc1]

This compound was prepared from 4-bromobenzaldehyde using General Procedure B-1. $^1$H NMR (400 MHz, CDCl$_3$) δ 7.48 (d, J=8.4 Hz, 2H), 7.22 (d, J=8.3 Hz, 2H), 4.59 (dd, J=8.9, 5.0 Hz, 1H), 4.14 (qd, J=7.1, 0.7 Hz, 2H), 3.21 (s, 3H), 2.77 (dd, J=15.4, 8.9 Hz, 1H), 2.53 (dd, J=15.4, 5.0 Hz, 1H), 1.23 (t, J=7.1 Hz, 3H). $^{13}$C NMR (101 MHz, CDCl$_3$) δ 170.8, 139.8, 131.9, 128.5, 122.0, 79.6, 60.8, 57.1, 43.5, 14.3. HRMS (FAB) m/z: 287.0282 (M+H$^+$); calc. for C$_{12}$H$_{16}$$^{79}$BrO$_3$: 287.0283

Ethyl 3-methoxy-3-(4-(trifluoromethyl)phenyl)propanoate (3d)

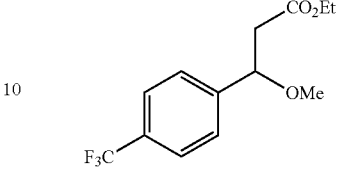

This compound was prepared from 4-(trifluoromethyl)benzaldehyde using General Procedure B-1. $^1$H NMR (400 MHz, CDCl$_3$) δ 7.62 (d, J=8.0 Hz, 2H), 7.46 (d, J=8.2 Hz, 2H), 4.70 (dd, J=8.8, 4.9 Hz, 1H), 4.15 (qd, J=7.2, 0.7 Hz, 2H), 3.24 (s, 3H), 2.79 (dd, J=15.5, 8.9 Hz, 1H), 2.56 (dd, J=15.4, 4.9 Hz, 1H), 1.24 (t, J=7.1 Hz, 3H). $^{13}$C NMR (101 MHz, CDCl$_3$) δ 170.7, 145.0, 130.4 (q, J=32.4 Hz), 127.1, 125.7 (q, J=3.8 Hz), 124.2 (q, J=272.1 Hz), 79.7, 60.9, 57.3, 43.5, 14.3. HRMS (FAB) m/z: 277.1041 (M+H$^+$); calc. for C$_{13}$H$_{16}$F$_3$O$_3$: 277.1052

Ethyl 3-methoxy-3-(m-tolyl)propanoate (3e)

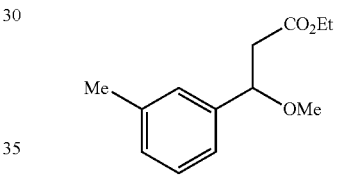

This compound was prepared from 3-methylbenzaldehyde using General Procedure B-1. $^1$H NMR (400 MHz, CDCl$_3$) δ 7.27-7.21 (m, 1H), 7.16-7.08 (m, 3H), 4.60 (dd, J=9.2, 4.6 Hz, 1H), 4.15 (qd, J=7.1, 1.3 Hz, 2H), 3.22 (s, 3H), 2.79 (dd, J=15.3, 9.3 Hz, 1H), 2.56 (dd, J=15.3, 4.6 Hz, 1H), 2.36 (s, 3H), 1.24 (t, J=7.1 Hz, 3H). $^{13}$C NMR (101 MHz, CDCl$_3$) δ 171.2, 140.7, 138.3, 128.9, 128.6, 127.4, 123.8, 80.2, 60.7, 57.0, 43.7, 21.6, 14.3. HRMS (FAB) m/z: 223.1338 (M+H$^+$); calc. for C$_{13}$H$_{19}$O$_3$: 223.1334.

Ethyl 2-(1,3-dihydroisobenzofuran-1-yl)acetate (3f)

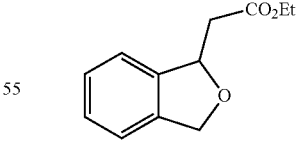

This compound was prepared by the method of U. S. Dakarapu et al. To a flame-dried Schlenk flask under argon was added [Ir(coe)$_2$Cl]$_2$ (5 mg, 0.0056 mmol, 0.11 mol %), phthalide (671 mg, 5 mmol, 1.0 equiv.), anhydrous dichloromethane (1.6 mL), and H$_2$SiEt$_2$ (1.3 mL, 10 mmol, 2 equiv.). The reaction mixture was stirred for 14 hours at room temperature. The reaction mixture was concentrated under reduced pressure to afford the crude silyl acetal, which was used without purification.

In a dry round bottom flask, the crude silyl acetal (5 mmol, 1.0 equiv.) was combined with THF (5 mL) and the resulting mixture cooled to 0° C. To the mixture were added triethyl phosphonoacetate (1.23 g, 5.5 mmol, 1.1 equiv.) and KOSiMe₃ (713 mg, 5 mmol, 1.0 equiv.) in THF (7.5 mL). The reaction was allowed to warm to room temperature and stirred for 1.5 hours. The reaction was quenched with the addition of NH₄Cl (sat. aq., 12 mL) and the aqueous phase was extracted with diethyl ether (3×15 mL). The combined organics were washed with brine (15 mL), dried over Na₂SO₄, and concentrated under reduced pressure. Purification by silica column chromatography with hexanes/ethyl acetate afforded desired product 3f with impurities (667 mg, 3.2 mmol, 65% yield). A portion of the product was taken for a second purification by reverse phase chromatography (Biotage Isolera equipped with Biotage SNAP Ultra C18 column, water/acetonitrile eluent system).

Spectral data are in agreement with literature report. $^1$H NMR (400 MHz, CDCl₃) δ 7.33-7.26 (m, 2H), 7.25-7.16 (m, 2H), 5.71-5.63 (m, 1H), 5.19-5.13 (m, 1H), 5.11-5.04 (m, 1H), 4.20 (q, J=7.1 Hz, 2H), 2.80 (dd, J=15.6, 4.9 Hz, 1H), 2.73 (dd, J=15.6, 7.9 Hz, 1H), 1.27 (t, J=7.1 Hz, 3H). $^{13}$C NMR (101 MHz, CDCl₃) δ 171.0, 140.8, 139.3, 128.0, 127.6, 121.3, 121.2, 80.5, 72.9, 60.8, 41.8, 14.3.

Ethyl 2-(isochroman-1-yl)acetate (3g)

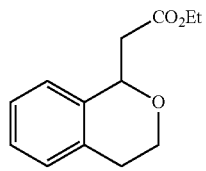 [SMILES: CCOC(=O)CC1OCCc2ccccc21]

This compound was prepared by the method of R. E. TenBrink et al. To a 100 mL dry round bottom flask, under argon, were added 2-phenylethanol (1.47 g, 12 mmol, 1.0 equiv.), ethyl 3,3-diethoxypropionate (90% technical grade, 2.51 g, 13.2 mmol, 1.1 equiv.), and anhydrous dichloromethane (5 mL). The resulting mixture was cooled to 0° C. and TiCl₄ (1 M in dichloromethane, 26.4 mL, 26.4 mmol, 2.2 equiv.) was added slowly. The reaction was stirred for 2 hours at 0° C. and a second portion of ethyl 3,3-diethoxypropionate (90% technical grade, 0.12 g, 0.6 mmol, 0.05 equiv.) was added. The reaction was stirred for an additional 2 hours at 0° C. The mixture was poured into ice cold HCl (aq., 1 M, 20 mL) and the aqueous phase was extracted with dichloromethane (2×20 mL). The combined organics were washed with brine (30 mL), dried over Na₂SO₄, and concentrated under reduced pressure. Purification by silica column chromatography with hexanes/ethyl acetate afforded desired product 3g with minor impurities (2.59 g, ~11.8 mmol, ~98% yield). A portion of the product was taken for a second purification by reverse phase chromatography (Biotage Isolera equipped with Biotage SNAP Ultra C18 column, water/acetonitrile eluent system).

Spectral data are in agreement with literature report. $^1$H NMR (400 MHz, CDCl₃) δ 7.22-7.15 (m, 2H), 7.15-7.09 (m, 1H), 7.08-7.02 (m, 1H), 5.25 (dd, J=9.6, 3.5 Hz, 1H), 4.22 (q, J=7.1 Hz, 2H), 4.13 (ddd, J=11.4, 5.2, 4.2 Hz, 1H), 3.82 (ddd, J=11.4, 9.0, 3.9 Hz, 1H), 3.04-2.93 (m, 1H), 2.88 (dd, J=15.2, 3.6 Hz, 1H), 2.80-2.68 (m, 2H), 1.28 (t, J=7.2 Hz, 3H). $^{13}$C NMR (101 MHz, CDCl₃) δ 171.4, 136.9, 134.1, 129.2, 126.8, 126.4, 124.6, 73.1, 63.2, 60.8, 41.9, 28.9, 14.3.

Ethyl 3-(4-(dimethylsilyl)phenyl)-3-methoxypropanoate (3h)

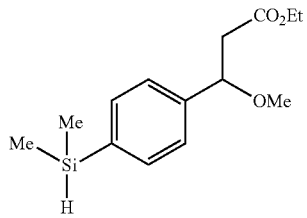 [SMILES: CCOC(=O)CC(OC)c1ccc([SiH](C)C)cc1]

This compound was prepared from ethyl 3-(4-bromophenyl)-3-methoxypropanoate (3c). The following procedure was modified from the literature. To a 25 mL round bottom flask was added Mg turnings* (48 mg, 2.0 mmol, 2.0 equiv.), flame dried, and cooled under positive argon pressure. (*Mg turnings were prepared by washing with 0.1 M HCl, sonication, then washing with H₂O and acetone.) THF (3 mL), LiCl (64 mg, 1.5 mmol, 1.5 equiv.), and Me₂SiHCl (170 mg, 1.8 mmol, 1.8 equiv.) were added and the resulting mixture was stirred for 30 minutes at room temperature under positive argon pressure. Aryl bromide 3c (287 mg, 1.0 mmol, 1.0 equiv.) was added dropwise via syringe and the reaction was stirred for an additional 2 hours. The crude reaction mixture was filtered through a pad of Celite and concentrated under reduced pressure. Purification by silica column chromatography with hexanes/ethyl acetate afforded desired product 3h (145 mg, 0.54 mmol, 54% yield).

$^1$H NMR (400 MHz, CDCl₃) δ 7.54 (d, J=8.0 Hz, 2H), 7.33 (d, J=7.9 Hz, 2H), 4.63 (dd, J=9.3, 4.5 Hz, 1H), 4.42 (hept, J=3.8 Hz, 1H), 4.15 (qd, J=7.1, 1.6 Hz, 2H), 3.23 (s, 3H), 2.79 (dd, J=15.3, 9.3 Hz, 1H), 2.56 (dd, J=15.3, 4.5 Hz, 1H), 1.24 (t, J=7.2 Hz, 3H), 0.35 (d, J=3.8 Hz, 6H). $^{13}$C NMR (101 MHz, CDCl₃) δ 171.1, 141.8, 137.4, 134.4, 126.2, 80.2, 60.7, 57.1, 43.7, 14.3, −3.6. HRMS (FAB) m/z: 265.1253 [(M+H⁺)—H₂]; calc. for C₁₄H₂₁SiO₃: 265.1260.

Ethyl 2-((4-(methoxymethyl)phenyl)dimethylsilyl) acetate (3h')

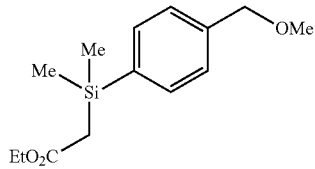 [SMILES: CCOC(=O)C[Si](C)(C)c1ccc(COC)cc1]

This compound was prepared by rhodium-catalyzed Si—H insertion. To a dry 50 mL round bottom flask, under argon, was added (4-(methoxymethyl)phenyl)dimethylsilane (1h) (541 mg, 3 mmol, 1.0 equiv.), Rh₂(OAc)₄ (13.3 mg, ~1 mol %), and anhydrous dichloromethane (12 mL). The mixture was cooled to −78° C., after which ethyl diazoacetate (393 mg, 3.0 mmol, 1.0 equiv.) in dichloromethane (3 mL) was added dropwise to the solution over 2 hours. The reaction was allowed to slowly warm to room temperature and stirred for a total of 12 hours. The crude reaction mixture was filtered through a pad of Celite and concentrated under reduced pressure. The crude mixture was purified by silica column chromatography using hexanes/ethyl acetate to deliver 3h' with impurities. A second purification by silica column chromatography using hexanes/diethyl ether/dichloromethane afforded 3h' (92.6 mg, 0.35 mmol, 12% yield).

$^1$H NMR (400 MHz, CDCl$_3$) δ 7.52 (d, J=8.1 Hz, 2H), 7.34 (d, J=8.1 Hz, 2H), 4.46 (s, 2H), 4.04 (q, J=7.2 Hz, 2H), 3.39 (s, 3H), 2.11 (s, 2H), 1.16 (t, J=7.1 Hz, 3H), 0.40 (s, 6H). $^{13}$C NMR (101 MHz, CDCl$_3$) δ 172.7, 139.7, 136.4, 133.8, 127.2, 74.6, 60.1, 58.3, 26.4, 14.5, −2.6. HRMS (FAB) m/z: 265.1260 [(M+H$^+$)—H$_2$]; calc. for C$_{14}$H$_{21}$SiO$_3$: 265.1260.

Ethyl 3-(4-methoxyphenyl)butanoate (3i)

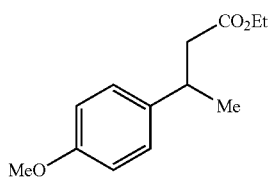 [SMILES: CCOC(=O)CC(C)c1ccc(OC)cc1]

This compound was prepared from 1-(4-methoxyphenyl)ethan-1-one using General Procedure C. $^1$H NMR (500 MHz, CDCl$_3$) δ 7.14 (d, J=8.5 Hz, 2H), 6.84 (d, J=8.7 Hz, 2H), 4.08 (qd, J=7.2, 1.2 Hz, 2H), 3.79 (s, 3H), 3.24 (h, J=7.1 Hz, 1H), 2.57 (dd, J=14.9, 7.2 Hz, 1H), 2.51 (dd, J=14.9, 8.0 Hz, 1H), 1.28 (d, J=7.0 Hz, 3H), 1.19 (t, J=7.1 Hz, 3H). Spectral data are in agreement with that for the enzymatic product.

Ethyl 3-(4-methoxyphenyl)pentanoate (3j)

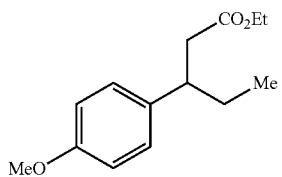 [SMILES: CCOC(=O)CC(CC)c1ccc(OC)cc1]

This compound was prepared from 1-(4-methoxyphenyl)propan-1-one using General Procedure C. Spectral data are in agreement with literature report; $^1$H NMR (400 MHz, CDCl$_3$) δ 7.09 (d, J=8.6 Hz, 2H), 6.83 (d, J=8.8 Hz, 2H), 4.03 (qd, J=7.2, 1.3 Hz, 2H), 3.78 (s, 3H), 2.95 (tdd, J=9.0, 7.0, 5.3 Hz, 1H), 2.60 (dd, J=15.0, 7.0 Hz, 1H), 2.51 (dd, J=14.9, 8.3 Hz, 1H), 1.68 (ddq, J=13.3, 7.4, 5.4 Hz, 1H), 1.56 (ddq, J=13.5, 9.4, 7.3 Hz, 1H), 1.14 (t, J=7.1 Hz, 3H), 0.78 (t, J=7.4 Hz, 3H). $^{13}$C NMR (101 MHz, CDCl$_3$) δ 172.7, 158.2, 136.1, 128.5, 113.8, 60.3, 55.3, 43.3, 41.9, 29.4, 14.3, 12.1.

Ethyl 3-(4-ethylphenyl)butanoate (3k)

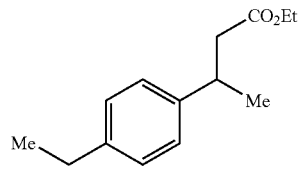 [SMILES: CCOC(=O)CC(C)c1ccc(CC)cc1]

This compound was prepared from 1-(4-ethylphenyl)ethan-1-one using General Procedure C. $^1$H NMR (400 MHz, CDCl$_3$) δ 7.14 (app. s, 4H), 4.08 (q, J=7.1 Hz, 2H), 3.25 (dp, J=8.3, 7.0 Hz, 1H), 2.66-2.48 (m, 4H), 1.29 (d, J=6.9 Hz, 3H), 1.26-1.15 (m, 6H). $^{13}$C NMR (101 MHz, CDCl$_3$) δ 172.7, 143.1, 142.3, 128.0, 126.8, 60.4, 43.2, 36.2, 28.5, 22.0, 15.7, 14.3. HRMS (FAB) m/z: 221.1532 (M+H$^+$); calc. for C$_{14}$H$_{21}$O$_2$: 221.1542

Ethyl 3-(4-isopropylphenyl)butanoate (3l)

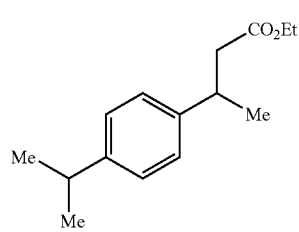 [SMILES: CCOC(=O)CC(C)c1ccc(C(C)C)cc1]

This compound was prepared from 1-(4-isopropylphenyl)ethan-1-one using General Procedure C. $^1$H NMR (400 MHz, CDCl$_3$) δ 7.15 (app. s, 4H), 4.08 (q, J=7.1 Hz, 2H), 3.25 (dp, J=8.5, 6.9 Hz, 1H), 2.87 (hept, J=6.9 Hz, 1H), 2.60 (dd, J=14.9, 6.7 Hz, 1H), 2.51 (dd, J=14.9, 8.4 Hz, 1H), 1.29 (d, J=7.0 Hz, 3H), 1.23 (d, J=6.9 Hz, 6H), 1.18 (t, J=7.1 Hz, 3H). $^{13}$C NMR (101 MHz, CDCl$_3$) δ 172.7, 147.0, 143.2, 126.8, 126.6, 60.4, 43.3, 36.2, 33.8, 24.2, 21.9, 14.3. HRMS (FAB) m/z: 235.1696 (M+H$^+$); calc. for C$_{15}$H$_{23}$O$_2$: 235.1698.

Ethyl 3-(4-methoxyphenyl)pent-4-enoate (3m)

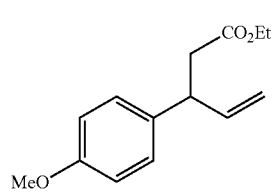 [SMILES: C=CC(CC(=O)OCC)c1ccc(OC)cc1]

This compound was accessed in a two-step sequence. First, p-methoxycinnamaldehyde (811 mg, 5 mmol, 1.0 equiv.) was reduced using NaBH$_4$ (227 mg, 6 mmol, 1.2 equiv.) in methanol (15 mL) under standard reaction conditions (0° C. for 2 hours). The reaction mixture was quenched with NH$_4$Cl (sat. aq., 10 mL) and diluted with dichloromethane (15 mL). Phases were separated and the aqueous layer was extracted with dichloromethane (4×15 mL). The combined organics were washed with brine (25 mL), dried over Na$_2$SO$_4$, and concentrated under reduced pressure. Purification by silica column chromatography with hexanes/ethyl acetate delivered p-methoxycinnamyl alcohol (752 mg, 4.6 mmol, 92% yield), with spectral data that match literature report.

Next, to a 50 mL round bottom flask equipped with short-path condenser were added p-methoxycinnamyl alcohol (740 mg, 4.5 mmol, 1.0 equiv.), triethyl orthoacetate (7.3 g, 45 mmol, 10 equiv.), and propionic acid (52 mg, 0.7 mmol, 0.15 equiv.). Following standard Johnson-Claisen rearrangement conditions, this mixture was heated to 140° C. until complete conversion of p-methoxycinnamyl alcohol was observed by TLC (~23 hours). Additional propionic acid (2×52 mg) was added after 6 hours and 9 hours reaction time. The reaction mixture was removed from heat, concentrated under reduced pressure, and purified using silica gel chromatography with hexanes/ethyl acetate as eluents. A second purification by silica gel chromatography with hexanes/ether afforded 3m (357 mg, 1.6 mmol, 36% yield).

Spectral data for 3m are in agreement with literature report. $^1$H NMR (400 MHz, CDCl$_3$) δ 7.13 (d, J=8.6 Hz, 2H), 6.85 (d, J=8.8 Hz, 2H), 5.96 (ddd, J=17.5, 9.9, 6.9 Hz, 1H), 5.09-5.05 (m, 1H), 5.03 (dt, J=5.4, 1.3 Hz, 1H), 4.07 (qd, J=7.1, 1.0 Hz, 2H), 3.86-3.80 (m, 1H), 3.78 (s, 3H), 2.73 (dd, J=15.0, 8.0 Hz, 1H), 2.65 (dd, J=15.0, 7.6 Hz, 1H), 1.18 (t, J=7.1 Hz, 3H). $^{13}$C NMR (101 MHz, CDCl$_3$) δ 172.1, 158.4, 140.7, 134.6, 128.6, 114.6, 114.0, 60.5, 55.4, 44.9, 40.6, 14.3.

Ethyl 2-(4-methoxybenzyl)cyclopropane-1-carboxylate (3m′)

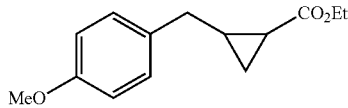 [SMILES: CCOC(=O)C1CC1Cc1ccc(OC)cc1]

This compound was prepared by rhodium-catalyzed alkene cyclopropanation. To a dry 100 mL round bottom flask, under argon, were added 4-allylanisole (3.0 g, 20 mmol, 10 equiv.), Rh$_2$(OAc)$_4$ (8.8 mg, ~1 mol %), and anhydrous dichloromethane (10 mL). Ethyl diazoacetate (262 mg, 2 mmol, 1.0 equiv.) in dichloromethane (10 mL) was added over ~8 hours using a syringe pump; the reaction mixture was allowed to stir for a total of 20 hours at room temperature. The reaction mixture was diluted with diethyl ether (20 mL), filtered through a pad of Celite, and concentrated under reduced pressure. Several rounds of purification by silica column chromatography with hexanes/ethyl acetate or hexanes/diethyl ether eluent systems afforded cis-3m′ and trans-3m′ as individual isomers (combined mass 148.1 mg, 0.632 mmol, 32% yield).

Spectral data are in agreement with literature report. Characterization data for cis-3m′: $^1$H NMR (400 MHz, CDCl$_3$) δ 7.13 (d, J=8.7 Hz, 2H), 6.83 (d, J=8.8 Hz, 2H), 4.13 (q, J=7.2 Hz, 2H), 3.79 (s, 3H), 2.86 (dd, J=14.9, 6.9 Hz, 1H), 2.77 (dd, J=15.0, 7.6 Hz, 1H), 1.77 (ddd, J=8.8, 7.6, 5.9 Hz, 1H), 1.56-1.44 (m, 1H), 1.24 (t, J=7.1 Hz, 3H), 1.14-1.06 (m, 2H). $^{13}$C NMR (101 MHz, CDCl$_3$) δ 173.1, 158.0, 133.7, 129.3, 113.9, 60.5, 55.4, 32.1, 23.1, 18.7, 14.5, 13.7. Characterization data for trans-3m′: $^1$H NMR (400 MHz, CDCl$_3$) δ 7.12 (d, J=8.7 Hz, 2H), 6.84 (d, J=8.7 Hz, 2H), 4.11 (qd, J=7.1, 1.1 Hz, 2H), 3.79 (s, 3H), 2.71 (dd, J=14.7, 6.3 Hz, 1H), 2.52 (dd, J=14.8, 7.1 Hz, 1H), 1.65 (ddtd, J=8.7, 7.1, 6.4, 4.1 Hz, 1H), 1.52-1.46 (m, 1H), 1.27-1.20 (m, 4H), 0.81 (ddd, J=8.2, 6.3, 4.2 Hz, 1H). $^{13}$C NMR (101 MHz, CDCl$_3$) δ 174.4, 158.2, 132.3, 129.5, 113.9, 60.5, 55.4, 37.6, 23.4, 20.3, 15.3, 14.4.

Ethyl (E)-3-methoxydec-4-enoate (5a)

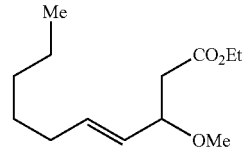 [SMILES: CCCCC/C=C/C(CC(=O)OCC)OC]

This compound was prepared from (E)-oct-2-enal using General Procedure B-2. $^1$H NMR (400 MHz, CDCl$_3$) δ 5.69 (dt, J=15.4, 6.8 Hz, 1H), 5.28 (ddt, J=15.4, 8.3, 1.5 Hz, 1H), 4.14 (qd, J=7.2, 0.8 Hz, 2H), 3.97 (td, J=8.2, 5.5 Hz, 1H), 3.25 (s, 3H), 2.59 (dd, J=14.9, 8.1 Hz, 1H), 2.42 (dd, J=14.9, 5.5 Hz, 1H), 2.10-1.97 (m, 2H), 1.43-1.20 (m, 9H), 0.88 (t, J=6.9 Hz, 3H). Spectral data are in agreement with that for the enzymatic product.

Ethyl (E)-3-methoxyoct-4-enoate (5b)

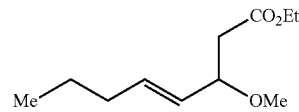 [SMILES: CCC/C=C/C(CC(=O)OCC)OC]

This compound was prepared from (E)-hex-2-enal using General Procedure B-2. $^1$H NMR (400 MHz, CDCl$_3$) δ 5.69 (dt, J=15.4, 6.8 Hz, 1H), 5.29 (ddt, J=15.4, 8.2, 1.5 Hz, 1H), 4.14 (qd, J=7.1, 0.8 Hz, 2H), 3.97 (td, J=8.1, 5.5 Hz, 1H), 3.25 (s, 3H), 2.59 (dd, J=14.9, 8.1 Hz, 1H), 2.42 (dd, J=14.9, 5.6 Hz, 1H), 2.06-1.99 (m, 2H), 1.40 (sext, J=7.3 Hz, 2H), 1.25 (t, J=7.1 Hz, 3H), 0.89 (t, J=7.4 Hz, 3H). $^{13}$C NMR (101 MHz, CDCl$_3$) δ 171.2, 135.3, 128.9, 79.0, 60.6, 56.2, 41.5, 34.3, 22.4, 14.4, 13.7. HRMS (FAB) m/z: 199.1320 [(M+H$^+$)—H$_2$]; calc. for C$_{11}$H$_{19}$O$_3$: 199.1334.

Ethyl (E)-9-bromo-3-methoxynon-4-enoate (5c)

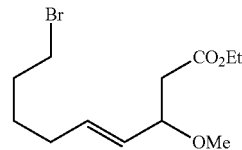 [SMILES: CCOC(=O)CC(/C=C/CCCCBr)OC]

This compound as prepared from (E)-7-bromohept-2-enal using General Procedure B-2. The synthesis of (E)-7-bromohept-2-enal was described in the synthesis of compound 4c. $^1$H NMR (400 MHz, Chloroform-d) δ 5.67 (dt, J=15.4, 6.7 Hz, 1H), 5.31 (dd, J=15.4, 8.1 Hz, 1H), 4.13 (q, J=7.1 Hz, 2H), 3.97 (td, J=8.0, 5.5 Hz, 1H), 3.40 (t, J=6.7 Hz, 2H), 3.25 (s, 3H), 2.59 (dd, J=15.0, 8.0 Hz, 1H), 2.41 (dd, J=15.0, 5.6 Hz, 1H), 2.08 (q, J=7.2 Hz, 2H), 1.91-1.79 (m, 2H), 1.53 (p, J=7.5 Hz, 2H), 1.25 (t, J=7.2 Hz, 3H). $^{13}$C NMR (101 MHz, CDCl$_3$) δ 171.1, 134.3, 129.5, 78.8, 60.6, 56.3, 41.4, 33.7, 32.2, 31.4, 27.7, 14.4. HRMS (FAB) m/z: 293.0764 (M+H⁺); calc. for $C_{12}H_{22}O_3{}^{79}Br$: 293.0752.

Ethyl (E)-5-(4-methoxyphenyl)-3-methylpent-4-enoate (5d)

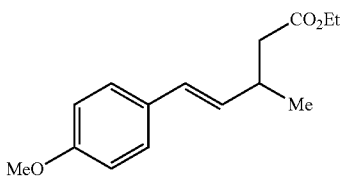 [SMILES: CCOC(=O)CC(C)/C=C/c1ccc(OC)cc1]

To a 6 mL vial equipped with a stir bar was added Grubbs' catalyst 2$^{nd}$ generation (10 mg, 2 mol %). The vial was then evacuated and backfilled with argon for three times. Under argon, a dry CH$_2$Cl$_2$ solution (2 mL) containing 4-vinylanisole (100 mg, 0.75 mmol) and ethyl 3-methylpent-4-enoate (503 mg, 3.75 mmol) was added to the vial via syringe. The mixture was stirred at 40° C. for 24 hours and then cooled to room temperature and filtered through a silica plug. The solvent was removed under reduced pressure and the crude product was purified using silica column chromatography with hexanes/ethyl acetate to give 5d (37 mg, 20% yield).

$^1$H NMR (400 MHz, CDCl$_3$) δ 7.30-7.24 (m, 2H), 6.84 (d, J=8.8 Hz, 2H), 6.34 (d, J=15.9 Hz, 1H), 5.99 (dd, J=15.9, 7.6 Hz, 1H), 4.12 (q, J=7.1 Hz, 2H), 3.80 (s, 3H), 2.90-2.75 (m, 1H), 2.41 (dd, J=14.7, 7.3 Hz, 1H), 2.34 (dd, J=14.7, 7.3 Hz, 1H), 1.23 (t, J=7.1 Hz, 3H), 1.14 (d, J=6.7 Hz, 3H). Spectral data are in agreement with that for the enzymatic product.

Ethyl 3-methoxydec-4-ynoate (5e)

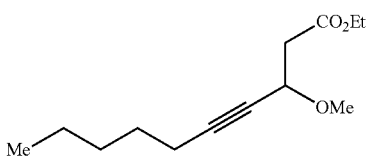 [SMILES: CCCCCC#CC(CC(=O)OCC)OC]

This compound was prepared from oct-2-ynal using General Procedure B-2. $^1$H NMR (400 MHz, CDCl$_3$) δ 4.39 (ddt, J=8.3, 5.4, 2.0 Hz, 1H), 4.16 (qd, J=7.2, 1.0 Hz, 2H), 3.39 (s, 3H), 2.73 (dd, J=15.5, 8.4 Hz, 1H), 2.63 (dd, J=15.5, 5.4 Hz, 1H), 2.20 (td, J=7.1, 2.0 Hz, 2H), 1.50 (p, J=7.2 Hz, 2H), 1.41-1.29 (m, 4H), 1.26 (t, J=7.1 Hz, 3H), 0.89 (t, J=7.1 Hz, 3H). $^{13}$C NMR (101 MHz, CDCl$_3$) δ 170.4, 87.3, 67.7, 60.8, 56.6, 41.7, 31.1, 28.4, 22.3, 18.8, 14.3, 14.1 (one carbon may be overlapping with the solvent peaks). HRMS (FAB) m/z: 227.1638 (M+H⁺); calc. for $C_{13}H_{23}O_3$: 227.1647.

Ethyl 2-(methoxymethyl)-3-pentylcycloprop-2-ene-1-carboxylate (5e')

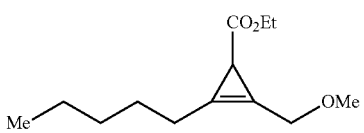 [SMILES: CCCCCC1=C(COC)C1C(=O)OCC]

This compound was prepared by rhodium-catalyzed cyclopropenation. To a dry 50 mL round bottom flask was added 1-methoxyoct-2-yne (4e) (280 mg, 2.0 mmol, 1.0 equiv.), Rh$_2$(OAc)$_4$ (9.0 mg, 1 mol %), and anhydrous dichloromethane (6 mL). The mixture was cooled to −78° C., after which ethyl diazoacetate (87%, 525 mg, 4.0 mmol, 2.0 equiv.) in dichloromethane (5 mL) was added dropwise to the solution over 6 hours. The reaction was allowed to slowly warm to room temperature and stirred for a total of 18 hours. The reaction mixture was concentrated under reduced pressure. The crude product was purified by silica column chromatography using hexanes/ethyl acetate, followed by C18 column using methanol/water, to afford 5e' (26 mg, 0.11 mmol, 6% yield).

$^1$H NMR (400 MHz, CDCl$_3$) δ 4.37 (t, J=1.6 Hz, 2H), 4.12 (q, J=7.1 Hz, 2H), 3.39 (s, 3H), 2.47 (tt, J=7.5, 1.6 Hz, 2H), 2.20 (s, 1H), 1.64-1.52 (m, 2H), 1.37-1.28 (m, 4H), 1.24 (t, J=7.1 Hz, 3H), 0.93-0.86 (m, 3H). $^{13}$C NMR (101 MHz, CDCl$_3$) δ 176.2, 110.3, 102.5, 65.8, 60.2, 58.6, 31.5, 26.7, 24.7, 22.7, 22.5, 14.5, 14.1. HRMS (EI) m/z: 226.1573 (M⁻˙); calc. for $C_{13}H_{22}O_3$: 226.1569.

Ethyl 3-(4-(dimethylamino)phenyl)propanoate (8a')

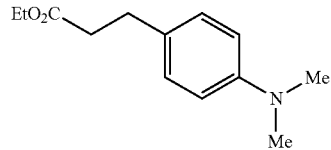 [SMILES: CCOC(=O)CCc1ccc(N(C)C)cc1]

This compound was prepared from 4-(dimethylamino) benzaldehyde using General Procedure C. $^1$H NMR (400 MHz, CDCl$_3$) δ 7.09 (d, J=8.7 Hz, 2H), 6.70 (d, J=8.7 Hz, 2H), 4.13 (q, J=7.2 Hz, 2H), 2.92 (s, 6H), 2.89-2.82 (m, 2H), 2.61-2.54 (m, 2H), 1.25 (t, J=7.1 Hz, 3H). $^{13}$C NMR (101 MHz, CDCl$_3$) δ 173.4, 149.4, 129.0, 128.8, 113.1, 60.4, 41.0, 36.6, 30.2, 14.4. HRMS (EI) m/z: 221.1430 (M⁺˙); calc. for $C_{13}H_{19}NO_2$: 221.1416.

Ethyl 3-(4-(dimethylamino)phenyl)butanoate (8b')

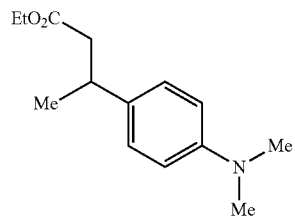 [SMILES: CCOC(=O)CC(C)c1ccc(N(C)C)cc1]

This compound was prepared from 1-(4-(dimethylamino) phenyl)ethan-1-one using General Procedure C. Spectral data are in agreement with literature report. $^1$H NMR (400 MHz, CDCl$_3$) δ 7.10 (d, J=8.7 Hz, 2H), 6.70 (d, J=8.7 Hz, 2H), 4.08 (qd, J=7.1, 1.1 Hz, 2H), 3.20 (dt, J=8.4, 6.8 Hz, 1H), 2.92 (s, 6H), 2.57 (dd, J=14.8, 6.8 Hz, 1H), 2.49 (dd, J=14.8, 8.4 Hz, 1H), 1.27 (d, J=7.0 Hz, 3H), 1.20 (t, J=7.1 Hz, 3H). $^{13}$C NMR (101 MHz, CDCl$_3$) δ 172.8, 149.4, 134.0, 127.4, 113.0, 60.3, 43.5, 41.0, 35.7, 22.0, 14.4.

Ethyl 3-(3,4-dihydroquinolin-1(2H)-yl)propanoate (8f')

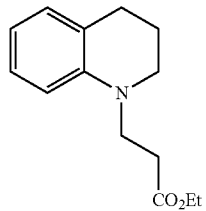 [SMILES: CCOC(=O)CCN1CCCc2ccccc21]

To a 100-mL round-bottom flask were added 1,2,3,4-tetrahydroquinoline (266.4 mg, 2.0 mmol, 1.0 equiv.), ethyl 3-bromopropanoate (0.97 mL, 6.0 mmol, 3.0 equiv.), K$_2$CO$_3$ (0.552 g, 4.0 mmol, 2.0 equiv.), KI (66.0 mg, 0.4 mmol, 0.2 equiv.) and N,N-dimethylformamide (30 mL). The reaction mixture was heated at 120° C. for 4 hours. After the reaction was cooled to room temperature and quenched by H$_2$O (40 mL), the crude product was extracted by diethyl ether (20 mL×3). The combined organic layer was washed by H$_2$O (40 mL) and brine (40 mL), and then dried over sodium sulfate and concentrated under reduced pressure. The crude product was purified by silica column chromatography with pentane/diethyl ether, followed by C18 column with methanol/water, to afford 8f(350 mg, 1.5 mmol, 75% yield).

This compound is known in the literature. $^1$H NMR (400 MHz, CDCl$_3$) δ 7.11-7.01 (m, 1H), 6.95 (dq, J=7.1, 1.1 Hz, 1H), 6.66-6.54 (m, 2H), 4.14 (q, J=7.1 Hz, 2H), 3.65-3.57 (m, 2H), 3.33-3.25 (m, 2H), 2.75 (t, J=6.4 Hz, 2H), 2.64-2.54 (m, 2H), 1.99-1.89 (m, 2H), 1.26 (t, J=7.1 Hz, 3H). $^{13}$C NMR (101 MHz, CDCl$_3$) δ 172.6, 144.6, 129.5, 127.3, 122.8, 116.2, 110.7, 60.7, 49.5, 47.4, 31.5, 28.1, 22.3, 14.4.

4-Methoxy-4-(4-methoxyphenyl)butan-2-one (10d)

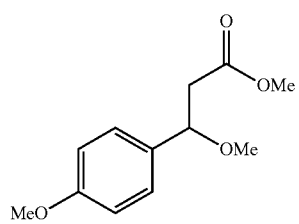 [SMILES: COC(=O)CC(OC)c1ccc(OC)cc1]

This compound was prepared according to the procedure of Yadav et al. Briefly, a mixture of 4-anisaldehyde (10 mmol), 2,2-dimethoxypropane (20 mmol) and iodine (0.2 mmol) in dry methylene chloride (20 mmol) was stirred under Na for 30 min. After the reaction was complete as indicated by TLC, the reaction mixture was diluted with water and extracted with ethyl acetate (2×30 mL). The combined organic extracts were washed with sodium thiosulfate (aq., 15% w/v) and brine, and then dried over sodium sulfate and concentrated under reduced pressure. The crude product was purified by silica column chromatography with hexanes/ethyl acetate.

$^1$H NMR (300 MHz, CDCl$_3$) δ 7.25-7.21 (m, 2H), 6.88 (d, J=8.8 Hz, 2H), 4.58 (dd, J=8.8, 4.5 Hz, 1H), 3.79 (s, 3H), 3.16 (s, 3H), 3.05-2.88 (m, 1H), 2.57 (dd, J=15.8, 4.5 Hz, 1H), 2.14 (s, 3H). Spectral data are in agreement with that for the enzymatic product.

Example 6

Application of New Enzymatic Methodology to Total Synthesis

To demonstrate the utility of this biotransformation, the methodology was applied to the formal synthesis of lyngbic acid (FIG. 6A). Marine cyanobacteria incorporate this versatile biomolecule into members of the malyngamide family of natural products; likewise, total synthesis approaches to these natural products typically access lyngbic acid as a strategic intermediate en route to the target molecules24. Using *E. coli* harboring P411-CHF, intermediate 5a was produced on 2.4 mmol scale in 86% isolated yield, 2810 TTN, and 94.7:5.3 e.r. Subsequent hydrogenation and hydrolysis provided (R)-(+)-6 in quantitative yield, which can be elaborated to (R)-(+)-lyngbic acid by decarboxylative alkenylation.

As part of the substrate scope studies described herein, P411-CHF was challenged with alkyl amine compounds. Substrates of this type are typically challenging substrates for C—H functionalization methods because the amine functionality may coordinate to and inhibit the catalyst or create the opportunity for undesirable side reactions (e.g., ylide formation and its associated rearrangements). Using substrate 7a or 7b, alkanes which have both benzylic C—H bonds and α-amino C—H bonds, P411-CHF delivered the corresponding β-amino ester product with high efficiency (8a and 8b, FIG. 6B). Notably, benzylic C—H insertion was not observed (with 7a) or significantly suppressed (with 7b), despite the typically lower BDEs of benzylic C—H bonds compared to α-amino C—H bonds. Additionally, N-aryl pyrrolidines (7c-7e) served as excellent substrates and were selectively alkylated at the α-amino sp$^3$ position. Using P411-CHF, the sp$^3$ C—H alkylation of 7c outcompetes a Friedel-Crafts type reaction on the aryl ring, which is a favorable process with other iron or rhodium-catalyzed carbene-transfer systems. Furthermore, alkylation product 8d offers a conceivable strategy for the synthesis of β-homoproline, a motif which has been investigated for medicinal chemistry applications.

Figure 6B:
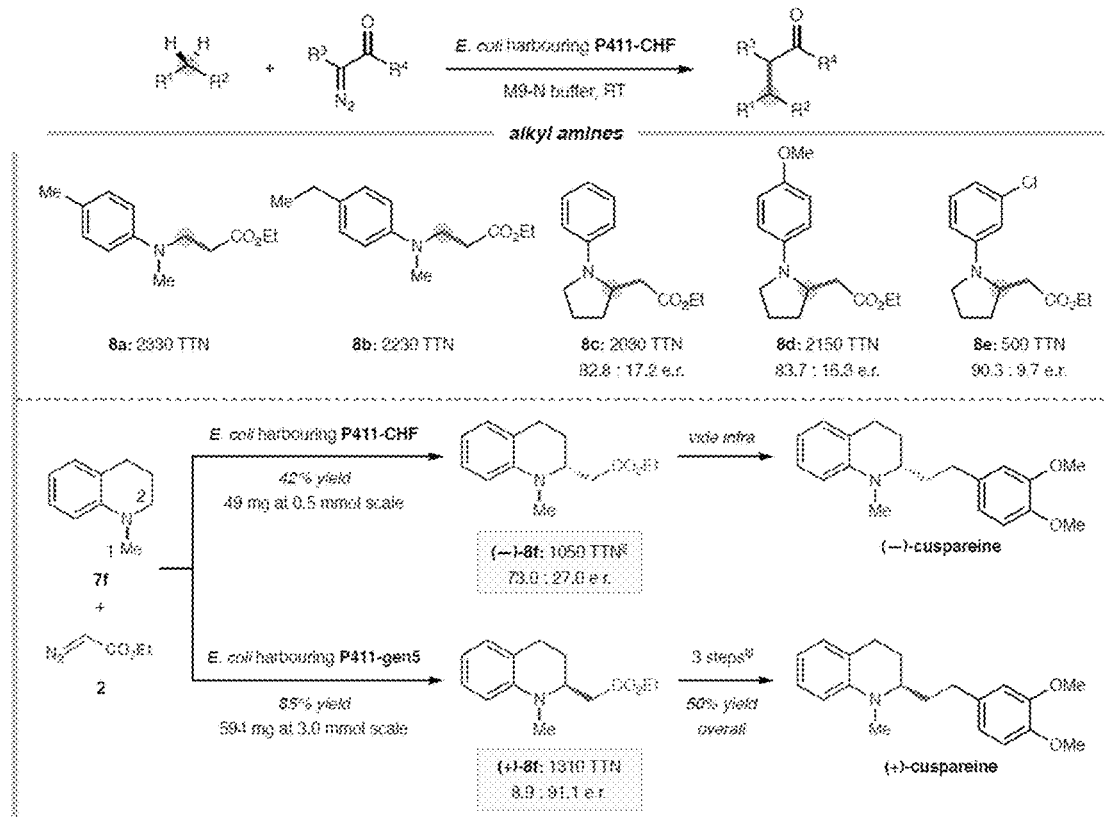
FIG. 6B shows the enzymatic alkylation of substrates containing α-amino C—H bonds. Unless otherwise indicated, experiments were performed at 0.5 mmol scale using *E. coli* expressing cytochrome P411-CHF with alkane 7a-7f and ethyl diazoacetate; TTNs were calculated based on isolated yield of alkylated product. ξIsolated in 9:1 r.r. for 8f:8f', determined by $^1$H nuclear magnetic resonance analysis; TTN is reported for the sum of the regioisomers. Steps marked with "ψ" included reduction, halogen exchange, and Suzuki-Miyaura cross-coupling.
Figure 6C:
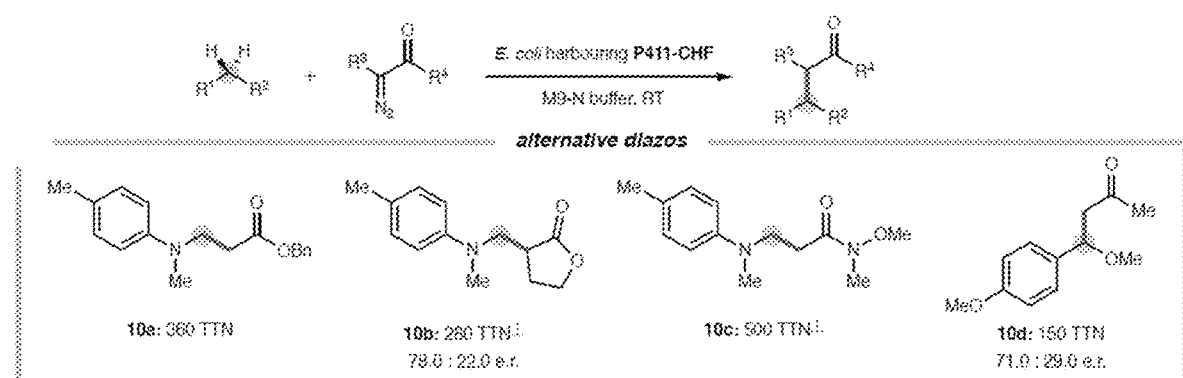
FIG. 6C shows enzymatic alkylation with alternative diazo reagents. Unless otherwise indicated, reactions were performed at 0.5 mmol scale using *E. coli* expressing cytochrome P411-CHF with substrate 1a or 7a and diazo compounds 9a-9d; TTNs were calculated based on isolated yield of alkylated product. For entries marked with "⊥" variant P411-IY T3271 was used. Alkane and diazo substrates are shown in FIG. 6E and FIG. 6F.
Figure 6D:
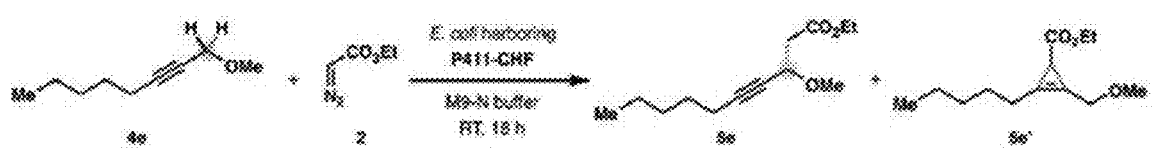
FIG. 6D shows a scheme for the reaction of P411-CHF with alkane 4e and ethyl diazoacetate (2) to produce cyclopropene 5e' as a side product.
Figure 6E:
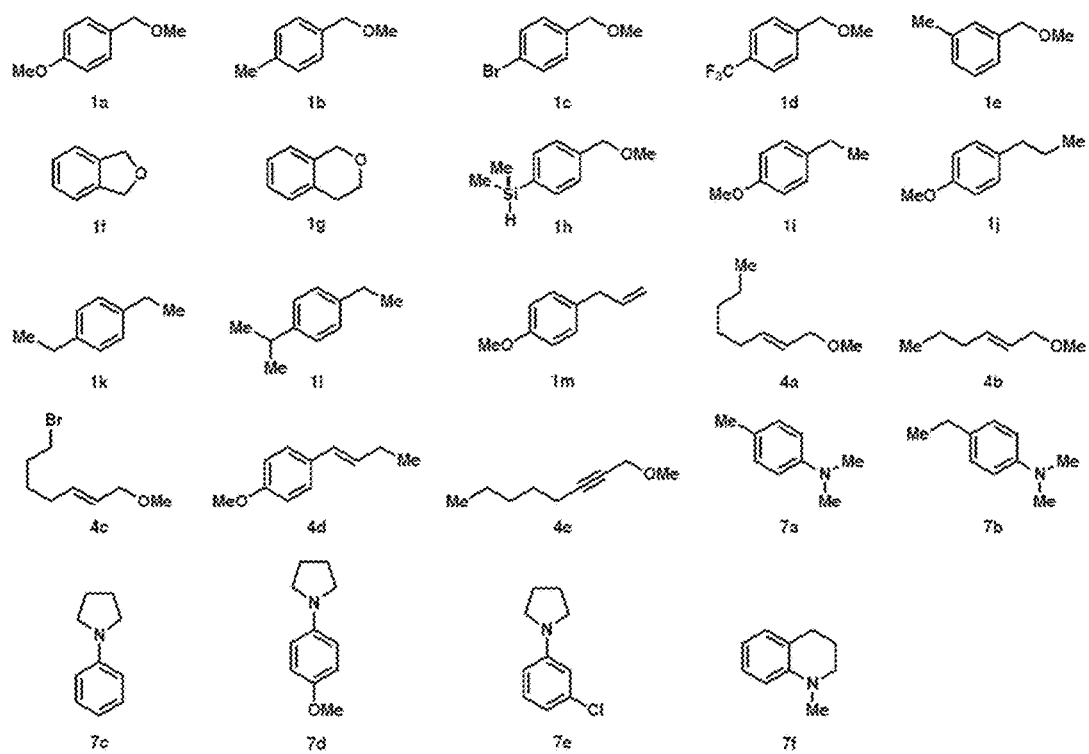
FIG. 6E shows alkane substrates according to the present disclosure.
Figure 6F:
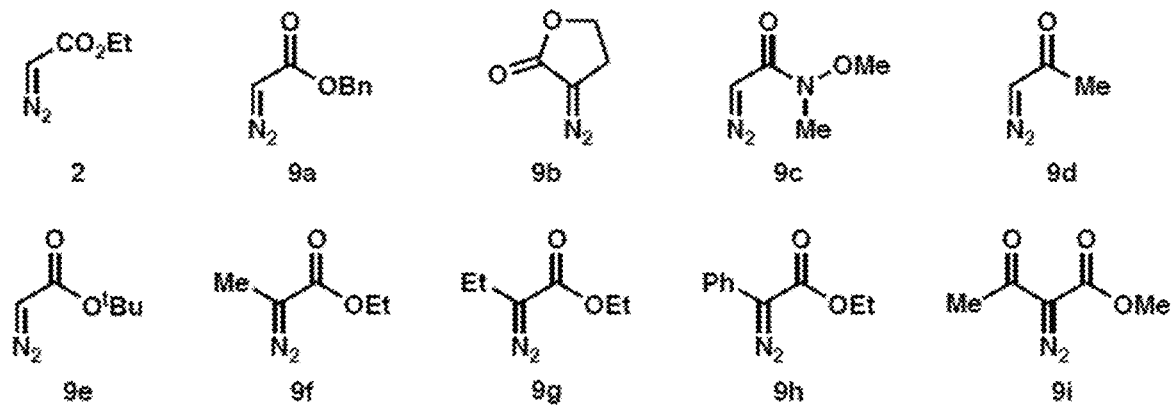
FIG. 6F shows diazo substrates according to the present disclosure.

Given that P411-CHF alkylates both primary and secondary α-amino C—H bonds, subsequent experiments were conducted to interrogate whether the enzyme could be selective for one of these positions. Employing N-methyl tetrahydroquinoline 7f as the alkane substrate, P411-CHF afforded β-amino ester products with 1050 TTN and a 9:1 ratio of regioisomers (C2:C1, and 73.0:27.0 e.r. for 8f) (FIG. 6B). As the tetrahydroquinoline ring system is a privileged structural motif in natural products and bioactive molecules, its selective functionalization could provide a concise strategy for the synthesis of natural alkaloids. To improve the selectivity for the alkylation of 7f, variants along the evolutionary lineage from P-4 A82L to P411-CHF were tested. It was found that P411-gen5 had even better regioselectivity and delivered product with the opposite stereo-preference. In a 3.0 mmol scale reaction, *E. coli* harboring P411-gen5 delivered 8f in 85% yield with excellent selectivity (1310 TTN, >50:1 r.r., 8.9:91.1 e.r.). In only a few steps, the enzymatic product was successfully transformed to alkaloid (R)-(+)-cuspareine (FIG. 6B). Future work with these and other heme proteins can lead to the development of predictable site-selective C—H alkylation enzymes.

Finally, the introduction of different alkyl groups was probed. With different diazo reagents, P411-CHF and related variants can rapidly diversify one alkane, such as 7a, to several products (10a-10c in FIG. 6C and 10e-10j in FIG.

5C). The diazo substrate scope extends beyond ester-based reagents: Weinreb amide diazo compound 9c and diazoketone 9d were found to participate in enzymatic C—H alkylation to furnish products 10c and 10d, respectively. In particular, the Weinreb amide moiety presents a useful functional handle for further product modification.

This study demonstrates that a cytochrome P450 can acquire the ability to construct C—C bonds from $sp^3$ C—H bonds and that activity and selectivity can be greatly enhanced using directed evolution. Unlike the radical SAM enzymes, which are principally known as methyltransferases, the evolved P411-CHF and related variants can install various alkyl fragments to diverse alkane substrates containing benzylic, allylic, and α-amino C—H bonds. Nature provides a huge collection of possible alternative starting points for expanding this scope even further and for achieving other selectivities. The cytochrome P450 superfamily can access an immense set of organic molecules for its native oxygenation chemistry. P411-derived enzymes and other natural heme protein diversity can be leveraged to generate families of C—H alkylation enzymes that emulate the scope and selectivity of nature's C—H oxygenation catalysts.

V. REFERENCES

Anslyn, E. V. & Dougherty, D. A. Modern Physical Organic Chemistry (University Science, Sausalito, Calif., 2006), chap. 8.

Bakos, M., Gyömöre, A., Domján, A. & Soós, T. Auto-tandem catalysis with frustrated lewis pairs for reductive etherification of aldehydes and ketones. Angew. Chem. Int. Ed. 56, 5217-5221 (2017).

Bauerle, M. R., Schwalm, E. L. & Booker, S. J. Mechanistic diversity of radical S-adenosylmethionine (SAM)-dependent methylation. J. Biol. Chem. 290, 3995-4002 (2015).

Berry, E. A. & Trumpower, B. L. Simultaneous determination of hemes a, b, and c from pyridine hemochrome spectra. Anal. Biochem. 161, 1-15 (1987).

Brandenberg, O. F., Fasan, R. & Arnold, F. H. Exploiting and engineering hemoproteins for abiological carbene and nitrene transfer reactions. Curr. Opin. Biotechnol. 47, 102-111 (2017).

Brandenberg, O. F., Prier, C. K., Chen, K., Knight, A. M., Wu, Z., Arnold, F. H. Stereoselective enzymatic synthesis of heteroatom-substituted cyclopropanes. ACS Catal. 8, 2629-2634 (2018).

Caballero, A., Despagnet-Ayoub, E., Díaz-Requejo, M. M., Díaz-Rodríguez, A., González-Núñez, M. E., Mello, R., Muñoz, B. K., Ojo, W.-S., Asensio, G., Etienne, M. & Pérez, P. J. Silver-catalyzed C—C bond formation between methane and ethyl diazoacetate in supercritical CO2. Science 332, 835-838 (2011).

Candish, L. & Lupton, D. W. N-heterocyclic carbene cascade catalysis: Dual Brønsted/Lewis base rearrangement of cyclopropyl enol esters to dihydropyranones. Chem. Sci. 3, 380-383 (2012).

Cardillo, G., Gentilucci, L., Qasem, A. R., Sgarzi, F. & Spampinato, S. Endomorphin-1 analogues containing β-Proline are μ-opioid receptor agonists and display enhanced enzymatic hydrolysis resistance. J. Med. Chem. 45, 2571-2578 (2002).

Coelho, P. S., Brustad, E. M., Kannan, A. & Arnold, F. H. Olefin cyclopropanation via carbene transfer catalyzed by engineered cytochrome P450 enzymes. Science 339, 307-310 (2013).

Coelho, P. S., Wang, Z. J., Ener, M. E., Baril, S. A., Kannan, A., Arnold, F. H. A serine-substituted P450 catalyzes highly efficient carbene transfer to olefins in vivo. Nat. Chem. Biol. 9, 485-487 (2013).

Colomer, I., Barcelos, R. C., Christensen, K. E. & Donohoe, T. J. Orthogonally protected 1,2-diols from electron-rich alkenes using metal-free olefin syn-dihydroxylation. Org. Lett. 18, 5880-5883 (2016).

Dakarapu, U. S., Bokka, A., Asgari, P., Trog, G., Hua, Y., Nguyen, H. H., Rahman, N. & Jeon, J. Lewis base activation of silyl acetals: iridium-catalyzed reductive Horner-Wadsworth-Emmons olefination. Org. Lett. 17, 5792-5795 (2015).

Davies, H. M. L., Hansen, T. & Churchill, M. R. Catalytic asymmetric C—H activation of alkanes and tetrahydrofuran, J. Am. Chem. Soc. 122, 3063-3070 (2000).

Demonceau, A., Noels, A. F., Costa, J.-L. & Hubert, A. J. Rhodium(II) carboxylate-catalyzed reactions of diazoesters: evidence for an equilibrium between free carbene and a metal-carbene complex. J. Mol. Catal. 58, 21-26 (1990).

Doyle, M. P., Westrum, L. J., Wolthuis, W. N. E., See, M. M., Boone, W. P., Bagheri, V. & Pearson, M. M. Electronic and steric control in carbon-hydrogen insertion reactions of diazoacetoacetates catalyzed by dirhodium(II) carboxylates and carboxamides. J. Am. Chem. Soc. 115, 958-964 (1993).

Edwards, J. T., Merchant, R. R., McClymont, K. S., Knouse, K. W., Qin, T., Malins, L. R., Vokits, B., Shaw, S. A., Bao, D.-H., Wei, F.-L., Zhou, T., Eastgate, M. D. & Baran, P. S. Decarboxylative alkenylation. Nature 545, 213-218 (2017).

Farwell, C. C., Zhang, R. K., McIntosh, J. A., Hyster, T. K. & Arnold, F. H. Enantioselective enzyme-catalyzed aziridination enabled by active-site evolution of a cytochrome P450. ACS Cent. Sci. 1, 89-93 (2015).

Frey, P. A. & Hegeman, A. D. Enzymatic Reaction Mechanisms (Oxford University Press, New York, 2007), chap. 14.

Gibson, D. G., Young, L., Chuang, R.-Y., Venter, J. C., Hutchinson III, C. A. & Smith, H. O. Enzymatic assembly of DNA molecules up to several hundred kilobases. Nat. Methods 6, 343-345 (2009).

Govindaraj, S. & Poulos, T. L. The domain architecture of cytochrome P450BM-3. J. Biol. Chem. 272, 7915-7921 (1997).

Griffin, J. R., Wendell, C. I., Garwin, J. A. & White, M. C. Catalytic $C(sp^3)$-H alkylation via an iron carbene intermediate. J. Am. Chem. Soc. 139, 13624-13627 (2017).

Guo, S. & Zhou, J. N,N-Dimethylformamide as hydride source in nickel-catalyzed asymmetric hydrogenation of α,β-unsaturated esters. Org. Lett. 18, 5344-5347 (2016).

Hari, D. P. & Waser, J. Enantioselective copper-catalyzed oxy-alkynylation of diazo compounds. J. Am. Chem. Soc. 139, 8420-8423 (2017).

Harms, A. E., Stille, J. R. & Taylor, S. K. Ring formation through intramolecular SN' displacement of an allylic methoxy substituent. Organometallics 13, 1456-1464 (1994).

Hartwig, J. F. & Larsen, M. A. Undirected, homogeneous C—H bond functionalization: Challenges and opportunities. ACS Cent. Sci. 2, 281-292 (2016).

Hattori, K., Sajiki, H., Hirota, K. Chemoselective control of hydrogenation among aromatic carbonyl and benzyl alcohol derivatives using Pd/C(en) catalyst. Tetrahedron 57, 4817-4824 (2001).

He, J., Hamann, L. G., Davies, H. M. L. & Beckwith, R. E. J. Late-stage C—H functionalization of complex alkaloids and drug molecules via intermolecular rhodium-carbenoid insertion. Nat. Commun. 6, 5943 (2015).

Hernandez, K. E., Renata, H., Lewis, R. D., Kan, S. B. J., Zhang, C., Forte, J., Rozzell, D., McIntosh, J. A. & Arnold, F. H. Highly stereoselective biocatalytic synthesis of key Cyclopropane Intermediate to Ticagrelor. ACS Catal. 6, 7810-7813 (2016).

Herschlag, D. & Natarajan, A. Fundamental challenges in mechanistic enzymology: Progress toward understanding the rate enhancements of enzymes. Biochemistry 52, 2050-2067 (2013).

Huang L., Niu, T., Wu, J. & Zhang, Y. Copper-catalyzed oxidative cross-coupling of N,N-dimethylanilines with heteroarenes under molecular oxygen. J. Org. Chem. 76, 1759-1766 (2011).

Huang, L. & Wulff, W. D. Catalytic asymmetric synthesis of trisubstituted aziridines. J. Am. Chem. Soc. 133, 8892-8895 (2011).

Huo, X., Yang, G., Liu, D., Liu, Y., Gridnev, I. D. & Zhang, W. Palladium-catalyzed allylic alkylation of simple ketones with allylic alcohols and its mechanistic study. Angew. Chem. Int. Ed. 53, 6776-6780 (2014).

Hyster, T. K., Farwell, C. C., Buller, A. R., McIntosh, J. A. & Arnold, F. H. Enzyme-controlled nitrogen-atom transfer enables regiodivergent C—H amination. J. Am. Chem. Soc. 136, 15505-15508 (2014).

Kan, S. B. J., Lewis, R. D., Chen, K. & Arnold, F. H. Directed evolution of cytochrome c for carbon-silicon bond formation: Bringing silicon to life. Science 354, 1048-1051 (2016).

Katritzky, A. R., Strah, S. & Belyakov, S. A. The preparation of functionalized amines and amides using benzotriazole derivatives and organozinc reagents. Tetrahedron 54, 7167-7178 (1998).

Key, H. M., Dydio, P., Clark, D. S. & Hartwig, J. F. Abiological catalysis by artificial haem proteins containing noble metals in place of iron. Nature 534, 534-537 (2016).

Kille, S., Acevedo-Rocha, C. G., Parra, L. P., Zhang, Z.-G., Opperman, D. J., Reetz, M. T. & Acevedo, J. P. Reducing codon redundancy and screening effort of combinatorial protein libraries created by saturation mutagenesis. ACS Synth. Biol. 2, 83-92 (2013).

Kirchhoff, J. H., Netherton, M. R., Hills, I. D. & Fu, G. C. Boronic acids: new coupling partners in room-temperature Suzuki reactions of alkyl bromides. Crystallographic characterization of an oxidative-addition adduct generated under remarkably mild conditions. J. Am. Chem. Soc. 124, 13662-13663 (2002).

Knight, A. M., Kan, S. B. J., Lewis, R. D., Brandenberg, O. F., Chen, K. & Arnold, F. H. Diverse engineered heme proteins enable stereodivergent cyclopropanation of unactivated alkenes. ACS Cent. Sci. 4, 372-377 (2018).

Koszelewski, D., Brodzka, A., Zqdlo, A., Paprocki, D., Trzepizur, D., Zysk, M. & Ostaszewski, R. Dynamic kinetic resolution of 3-aryl-4-pentenoic acids. ACS Catal. 6, 3287-3292 (2016).

Li, Y., Huang, J.-S., Zhou, Z.-Y., Che, C.-M., & You, X.-Z. Remarkably stable iron porphyrins bearing nonheteroatom-stabilized carbene or (alkoxycarbonyl)carbenes: Isolation, X-ray crystal structures, and carbon atom transfer reactions with hydrocarbons. J. Am. Chem. Soc. 124, 13185-13193 (2002).

Liao, K., Pickel, T. C., Boyarskikh, V., Bacsa, J., Musaev, D. G. & Davies, H. M. L. Site-selective and stereoselective functionalization of non-activated tertiary C—H bonds. Nature 551, 609-613 (2017).

Lu, W.-J., Chen, Y.-W. & Hou, X.-L. Highly enantioselective iridium-catalyzed hydrogenation of trisubstituted olefins, α,β-unsaturated ketones and imines with chiral benzylic substituted P,N-ligands. Adv. Synth. Catal. 352, 103-107 (2010).

Mbuvi, H. M. & Woo, L. K. Catalytic C—H insertions using iron(III) porphyrin complexes. Organometallics 27, 637-645 (2008).

McLaughlin, M. I. & van der Donk, W. A. Stereospecific radical-mediated B12-dependent methyl transfer by the fosfomycin biosynthesis enzyme Fom3. Biochemistry 57, 4967-4971 (2018).

Melzig, L., Dennenwaldt, T., Gavryushin, A. & Knochel, P. Direct aminoalkylation of arenes, heteroarenes, and alkenes via Ni-catalyzed Negishi cross-coupling reactions. J. Org. Chem. 76, 8891-8906 (2011).

Mitsudome, T., Mizumoto, K., Mizugaki, T., Jitsukawa, K. & Kaneda, K. Wacker-type oxidation of internal olefins using a PdCl2/N,N-dimethylacetamide catalyst system under copper-free reaction conditions. Angew. Chem. Int. Ed. 49, 1238-1240 (2010).

Park, S. R., Kim, C., Kim, D.-G., Thrimurtulu, N., Yeom, H.-S., Jun, J., Shin, S. & Rhee, Y. H. Entry to β-alkoxyacrylates via gold-catalyzed intermolecular coupling of alkynoates and allylic ethers. Org. Lett. 15, 1166-1169 (2013).

Poulos, T. L. Heme enzyme structure and function. Chem. Rev. 114, 3919-3962 (2014).

Prier, C. K., Zhang, R. K., Buller, A. R., Brinkmann-Chen, S. & Arnold, F. H. Enantioselective, intermolecular benzylic C—H amination catalysed by an engineered iron-haem enzyme. Nat. Chem. 9, 629-634 (2017).

Renata, H., Lewis, R. D., Sweredoski, M. J., Moradian, A., Hess, S., Wang, Z. J. & Arnold, F. H. Identification of mechanism-based inactivation in P450-catalyzed cyclopropanation facilitates engineering of improved enzymes. J. Am. Chem. Soc. 138, 12527-12533 (2016).

Saint-Denis, T. G., Zhu, R.-Y., Chen, G., Wu, Q.-F. & Yu, J.-Q. Enantioselective C(sp$^3$)-H bond activation by chiral transition metal catalysts. Science 359, doi: 10.1126/science.aao4798 (2018).

Sattely, E. S., Meek, S. J., Malcolmson, S. J., Schrock, R. R. & Hoveyda, A. H. Design and stereoselective preparation of a new class of chiral olefin metathesis catalysts and application to enantioselective synthesis of quebrachamine: Catalyst development inspired by natural product synthesis. J. Am. Chem. Soc. 131, 943-953 (2009).

Schwartz, B. D., Denton, J. R., Lian, Y., Davies, H. M. L. & Williams, C. M. Asymmetric [4+3] cyloadditions between vinylcarbenoids and dienes: application to the total synthesis of the natural product (-)-5-epi-Vibsanin E. J. Am. Chem. Soc. 131, 8329-8332 (2009).

Shao, Z., Fu, S., Wei, M., Zhou, S. & Liu, Q. Mild and selective cobalt-catalyzed chemodivergent transfer hydrogenation of nitriles, Angew. Chem. Int. Ed. 55, 14653-14657 (2016).

Shevlin, M., Friedfeld, M. R., Sheng, H., Pierson, N. A., Hoyt, J. M., Campeau, L.-C. & Chirik, P. J. Nickel-catalyzed asymmetric alkene hydrogenation of α,β-unsaturated esters: high-throughput experimentation-enabled reaction discovery, optimization, and mechanistic elucidation. J. Am. Chem. Soc. 138, 3562-3569 (2016).

Shisler, K. A. & Broderick, J. B. Glycyl radical activating enzymes: Structure, mechanism, and substrate interactions. Arch. Biochem. Biophys. 546, 64-71 (2014).

Solé, D. & Serrano, O. Palladium-Catalyzed intramolecular nucleophilic substitution at the alkoxycarbonyl group. Angew. Chem. Int. Ed. 46, 7270-7272 (2007).

Sridharan, V., Suryavanshi, P. A. & Menéndez, J. C. Advances in the chemistry of tetrahydroquinolines. Chem. Rev. 111, 7157-7259 (2011).

Su, B. & Hartwig, J. F. Ir-catalyzed enantioselective, intramolecular silylation of methyl C—H bonds. J. Am. Chem. Soc. 139, 12137-12140 (2017).

Tang, Y., Chen, Q., Liu, X., Wang, G., Lin, L. & Feng, X. Direct synthesis of chiral allenoates from the asymmetric C—H insertion of α-diazoesters into terminal alkynes. Angew. Chem. Int. Ed. 54, 9512-9516 (2015).

Teh, A.-H., Saito, J. A., Baharuddin, A., Tuckerman, J. R., Newhouse, J. S., Kanbe, M., Newhouse, E. I., Rahim, R. A., Favier, F., Didierjean, C., Sousa, E. H. S., Stott, M. B., Dunfield, P. F., Gonzalez, G., Gilles-Gonzalez, M.-A., Najimudin, N. & Alam, M. Hell's Gate globin I: An acid and thermostable bacterial hemoglobin resembling mammalian neuroglobin. FEBS Lett. 585, 3250-3258 (2011).

TenBrink, R. E., Bergh, C. L., Duncan, J. N., Harris, D. W., Huff, R. M., Lahti, R. A., Lawson, C. F., Lutzke, B. S., Martin, I. J., Rees, S. A., Schlachter, S. K., Sih, J. C. & Smith, M. W. (S)-(−)-4-[4-[2-(Isochroman-1-yl)ethyl]piperazin-1-yl]benzenesulfonamide, a selective dopamine D4 antagonist. J. Med. Chem. 39, 2435-2437 (1996).

Tsai, C.-C., Chuang, W.-T., Tsai, Y.-F., Li, J.-T., Wu, Y.-F. & Liao, C.-C. Intra- and intermolecular hydrogen bonds enhance the fluoride-responsiveness of functionalized glycolipid-based gelators. J. Mater. Chem. B 1, 819-827 (2013).

Wang, Y., Liu, Y., Zhang, D., Wei, H., Shi, M. & Wang, F. Enantioselective Rhodium-catalyzed deoamative arylation or alkenylation of quinolinium salts. Angew. Chem. Int. Ed. 55, 3776-3780 (2016).

Wang, Y., Wen, X., Cui, X. & Zhang, X. P. Enantioselective radical cyclization for construction of 5-membered ring structures by metalloradical C—H alkylation. J. Am. Chem. Soc. 140, 4792-4796 (2018).

Weldy, N. M., Schafer, A. G., Owens, C. P., Herting, C. J., Varela-Alvarez, A., Chen, S., Niemeyer, Z., Musaev, D. G., Sigman, M. S., Davies, H. M. L. & Blakey, S. B. Iridium(III)-bis(imidazolinyl)phenyl catalysts for enantioselective C—H functionalization with ethyl diazoacetate. Chem. Sci. 7, 3142-3146 (2016).

Wender, P. A., Deschamps, N. M. & Williams, T. J. Intermolecular dienyl Pauson-Khand reaction. Angew. Chem. Int. Ed. 43, 3076-3079 (2004).

Wu, W.-T, Yang, Z.-P. & You, S.-L. in Asymmetric Functionalization of C—H Bonds, ed. You, S.-L. (Royal Society of Chemistry, Cambridge, UK, 2015), chap. 1.

Xu, B., Li, M.-L., Zuo, X.-D., Zhu, S.-F. & Zhou, Q.-L. Catalytic asymmetric arylation of α-aryl-α-diazoacetates with aniline derivatives. J. Am. Chem. Soc. 137, 8700-8703 (2015).

Yadav, J. S., Reddy, B. V. S. & Hashim, S. R. A new and efficient synthesis of 2,2-disubstituted-3,4-dihydro-2H-1-benzopyrans. J. Chem. Soc., Perkin Trans. 1 0, 3082-3084 (2000).

Yang, J.-M., Cai, Y., Zhu, S.-F. & Zhou, Q.-L. Iron-catalyzed arylation of α-aryl-α-diazoesters. Org. Biomol. Chem. 14, 5516-5519 (2016).

Yin, G., Wu, Y. & Liu, G. Scope and mechanism of allylic C—H amination of terminal alkenes by the palladium/PhI(OPiv)2 catalyst system: insights into the effect of naphthoquinone. J. Am. Chem. Soc. 132, 11978-11987 (2010).

Yokoyama, K. & Lilla, E. A. C—C bond forming radical SAM enzymes involved in the construction of carbon skeletons of cofactors and natural products. Nat. Prod. Rep. 35, 660-694 (2018).

Zhang, J.-T., Qi, X.-L., Chen, J., Li, B.-S., Zhou, Y.-B. & Cao, X.-P. Total synthesis of malyngamides K, L, and 5″-epi-C and absolution configuration of malyngamide L. J. Org. Chem. 76, 3946-3959 (2011).

Zhang, L., Sun, B., Liu, Q. & Mo, F. Addition of diazo compounds ipso-C—H bond to carbon disulfide: Synthesis of 1,2,3-thiadiazoles under mild conditions. J. Org. Chem. 83, 4275-4278 (2018).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

VI. INFORMAL SEQUENCE LISTING

Truncated *B. megaterium* (strain ATCC) cytochrome P450 BM3-UniProt P14779

SEQ ID NO: 1

```
TIKEMPQPKTFGELKNLPLLNTDKPVQALMKIADELGEIFKFEAPGRVTR
YLSSQRLIKEACDESRFDKNLSQALKFVRDFAGDGLFTSWTHEKNWKKAH
NILLPSFSQQAMKGYHAMMVDIAVQLVQKWERLNADEHIEVPEDMTRLTL
DTIGLCGFNYRFNSFYRDQPHPFITSMVRALDEAMNKLQRANPDDPAYDE
NKRQFQEDIKVMNDLVDKIIADRKASGEQSDDLLTHMLNGKDPETGEPLD
DENIRYQIITFLIAGHETTSGLLSFALYFLVKNPHVLQKAAEEAARVLVD
PVPSYKQVKQLKYVGMVLNEALRLWPTAPAFSLYAKEDTVLGGEYPLEKG
DELMVLIPQLHRDKTIWGDDVEEFRPERFENPSAIPQHAFKPFGNGQRAC
IGQQFALHEATLVLGMMLKHFDFEDHTNYELDIKETLTLKPEGFVVKAKS
KKIPLGGIPSPSTEQSAKKVRKKAENAHNTPLLVLYGSNMGTAEGTARDL
ADIAMSKGFAPQVATLDSHAGNLPREGAVLIVTASYNGHPPDNAKQFVDW
LDQASADEVKGVRYSVFGCGDKNWATTYQKVPAFIDETLAAKGAENIADR
GEADASDDFEGTYEEWREHMWSDVAAYFNLDIENSEDNKSTLSLQFVDSA
ADMPLAKMHGAFST
```

*B. megaterium* (strain ATCC) cytochrome P450 BM3-UniProt P14779

SEQ ID NO: 2

```
TIKEMPQPKTFGELKNLPLLNTDKPVQALMKIADELGEIFKFEAPGRVTR
YLSSQRLIKEACDESRFDKNLSQALKFVRDFAGDGLFTSWTHEKNWKKAH
NILLPSFSQQAMKGYHAMMVDIAVQLVQKWERLNADEHIEVPEDMTRLTL
DTIGLCGFNYRFNSFYRDQPHPFITSMVRALDEAMNKLQRANPDDPAYDE
NKRQFQEDIKVMNDLVDKIIADRKASGEQSDDLLTHMLNGKDPETGEPLD
DENIRYQIITFLIAGHETTSGLLSFALYFLVKNPHVLQKAAEEAARVLVD
PVPSYKQVKQLKYVGMVLNEALRLWPTAPAFSLYAKEDTVLGGEYPLEKG
DELMVLIPQLHRDKTIWGDDVEEFRPERFENPSAIPQHAFKPFGNGQRAC
IGQQFALHEATLVLGMMLKHFDFEDHTNYELDIKETLTLKPEGFVVKAKS
```

KKIPLGGIPSPSTEQSAKKVRKKAENAHNTPLLVLYGSNMGTAEGTARDL

ADIAMSKGFAPQVATLDSHAGNLPREGAVLIVTASYNGHPPDNAKQFVDW

LDQASADEVKGVRYSVFGCGDKNWATTYQKVPAFIDETLAAKGAENIADR

GEADASDDFEGTYEEWREHMWSDVAAYFNLDIENSEDNKSTLSLQFVDSA

ADMPLAKMHGAFSTNVVASKELQQPGSARSTRHLEIELPKEASYQEGDHL

GVIPRNYEGIVNRVTARFGLDASQQIRLEAEEEKLAHLPLAKTVSVEELL

QYVELQDPVTRTQLRAMAAKTVCPPHKVELEALLEKQAYKEQVLAKRLTM

LELLEKYPACEMKFSEFIALLPSIRPRYYSISSSPRVDEKQASITVSVVS

GEAWSGYGEYKGIASNYLAELQEGDTITCFISTPQSEFTLPKDPETPLIM

VGPGTGVAPFRGFVQARKQLKEQGQSLGEAHLYFGCRSPHEDYLYQEELE

NAQSEGIITLHTAFSRMPNQPKTYVQHVMEQDGKKLIELLDQGAHFYICG

DGSQMAPAVEATLMKSYADVHQVSEADARLWLQQLEEKGRYAKDVWAG

B. megaterium P411-CHF
SEQ ID NO: 3
TIKEMPQPKTFGELKNLPLLNTDKPVQALMKIADELGEIFKFEAPGRVTR

YLSSQRLIKEACDESRFDKELSQPLKFLRDFLGDGLATSWTHEKNWKKAH

NILLPSFSQQAMKGYHAMMVDIAVQLVQKWERLNADEHIEVSEDMTRLTL

DTIGLCGFNYRFNSFYRDQPHPFIISLVRALDEVMNKLQRANPDDPAYDE

NKRQFQEDIKVMNDLVDKIIADRKARGEQSDDLLTQMLNGKDPETGEPLD

DGNIRYQIITFLYAGVEGTSGLLSFALYFLVKNPHVLQKVAEEEAARVLVD

PVPSYKQVKQLKYVGMVLNEALRLWPTVPYFSLYAKEDTVLGGEYPLEKG

DEVMVLIPQLHRDKTVWGDDVEEFRPERFENPSAIPQHAFKPFGNGQRAS

IGQQFALHEATLVLGMMLKHFDFEDHTNYELDIKELLTLKPKGFVVKAKS

KKIPLGGIPSPSTEQSAKKVRKKAENAHNTPLLVLYGSNMGTAEGTARDL

ADIAMSKGFAPQVATLDSHAGNLPREGAVLIVTASYNGHPPDNAKQFVDW

LDQASADEVKGVRYSVFGCGDKNWATTYQKVPAFIDETLAAKGAENIADR

GEADASDDFEGTYEEWREHMWSDVAAYFNLDIENSEDNKSTLSLQFVDSA

ADMPLAKMHGAFST

R. marinus nitric oxide dioxygenase-UniProt D0MGT2
SEQ ID NO: 4
MAPTLSEQTRQLVRASVPALQKHSVAISATMYRLLFERYPETRSLFELPE

RQIHKLASALLAYARSIDNPSALQAAIRRMVLSHARAGVQAVHYPLVWEC

LRDAIKEVLGPDATETLLQAWKEAYDFLAHLLSTKEAQVYAVLAE

M. infernorum Hell's Gate globin-UniProt B3DUZ7
SEQ ID NO: 5
MIDQKEKELIKESWKRIEPNKNEIGLLFYANLFKEEPTVSVLFQNPISSQ

SRKLMQVLGILVQGIDNLEGLIPTLQDLGRRHKQYGVVDSHYPLVGDCLL

KSIQEYLGQGFTEEAKAAWTKVYGIAAQVMTAE

C. jejuni globin-UniProt Q0P842
SEQ ID NO: 6
MTKEQIQIIKDCVPILQKNGEDLTNEFYKIMFNDYPEVKPMFNMEKQISG

EQPKALAMAILMAAKNIENLENMRSFVDKVAITHVNLGVKEEHYPIVGAC

LLKAIKNLLNPDEATLKAWEVAYGKIAKFYIDIEKKLYDK

V. stercoraria hemoglobin-UniProt P04252
SEQ ID NO: 7
MLDQQTINIIKATVPVLKEHGVTITTTFYKNLFAKHPEVRPLFDMGRQES

LEQPKALAMTVLAAAQNIENLPAILPAVKKIAVKHCQAGVAAAHYPIVGQ

ELLGAIKEVLGDAATDDILDAWGKAYGVIADVFIQVEADLYAQAVE

M. musculus neuroglobin-UniProt Q9ER97
SEQ ID NO: 8
MERPESELIRQSWRVVSRSPLEHGTVLFARLFALEPSLLPLFQYNGRQFS

SPEDCLSSPEFLDHIRKVMLVIDAAVTNVEDLSSLEEYLTSLGRKHRAVG

VRLSSFSTVGESLLYMLEKCLGPDFTPATRTAWSRLYGAVVQAMSRGWDG

E

H. sapiens neuroglobin-UniProt Q9NPG2
SEQ ID NO: 9
MERPEPELIRQSWRAVSRSPLEHGTVLFARLFALEPDLLPLFQYNCRQFS

SPEDCLSSPEFLDHIRKVMLVIDAAVTNVEDLSSLEEYLASLGRKHRAVG

VKLSSFSTVGESLLYMLEKCLGPAFTPATRAAWSQLYGAVVQAMSRGWDG

E

P. catodon myoglobin-UniProt P02185
SEQ ID NO: 10
MVLSEGEWQLVLHVWAKVEADVAGHGQDILIRLFKSHPETLEKFDRFKHL

KTEAEMKASEDLKKHGVTVLTALGAILKKKGHHEAELKPLAQSHATKHKI

PIKYLEFISEAIIHVLHSRHPGDFGADAQGAMNKALELFRKDIAAKYKEL

GYQG

H. sapiens cytoglobin-UniProt Q8WWM9
SEQ ID NO: 11
MEKVPGEMEIERRERSEELSEAERKAVQAMWARLYANCEDVGVAILVRFF

VNFPSAKQYFSQFKHMEDPLEMERSPQLRKHACRVMGALNTVVENLHDPD

KVSSVLALVGKAHALKHKVEPVYFKILSGVILEVVAEEFASDFPPETQRA

WAKLRGLIYSHVTAAYKEVGWVQQVPNATTPPATLSSGP

A. suum hemoglobin-UniProt P28316
SEQ ID NO: 12
MRSLLLLSIVFFVVTVSANKTRELCMKSLEHAKVDTSNEARQDGIDLYKH

MFENYPPLRKYFKNREEYTAEDVQNDPFFAKQGQKILLACHVLCATYDDR

ETFNAYTRELLDRHARDHVHMPPEVWTDFWKLFEEYLGKKTTLDEPTKQA

WHEIGREFAKEINKHGRHAVRHQCMRSLQHIDIGHSETAKQNGIDLYKHM

FENYPSMREAFKDRENYTAEDVQKDPFFVKQGQRILLACHLLCASYDDEE

TFHMYVHELMERHERLGVQLPDQHWTDFWKLFEEFLEKKSHLCEHTKHAW

AVIGKEFAYEATRHGKEHHEHKEEHKEEHKEEQH

B. subtilis group 2 truncated hemoglobin-UniProt O31607
SEQ ID NO: 13
MGQSFNAPYEAIGEELLSQLVDTFYERVASHPLLKPIFPSDLTETARKQK

QFLTQYLGGPPLYTEEHGHPMLRARHLPFPITNERADAWLSCMKDAMDHV

GLEGEIREFLFGRLELTARHMVNQTEAEDRSS

*M. acetivorans* protoglobin (strain ATCC 35395)-
UniProt Q8TLY9
SEQ ID NO: 14
MSVEKIPGYTYGETENRAPFNLEDLKLLKEAVMFTAEDEEYIQKAGEVLE
DQVEEILDTWYGFVGSHPLLYYFTSPDGTPNEKYLAAVRKRFSRWIIDT
CNRSYDQAWLDYQYEIGLRHHRTKKNQTDNVESVPNIGYRYLVAFIYPIT
ATMKPFLARKGHTPEEVEKMYQAWFKATTLQVALWSYPYVKYGDF

*A. pernix* protoglobin-UniProt Q9YFF4
SEQ ID NO: 15
MTPSDIPGYDYGRVEKSPITDLEFDLLKKTVMLGEKDVMYLKKACDVLKD
QVDEILDLWYGWVASNEHLIYYFSNPDTGEPIKEYLERVRARFGAWIIDT
TCRDYNREWLDYQYEVGLRHHRSKKGVTDGVRTVPHIPLRYLIAFIYPIT
ATIKPFLAKKGGSPEDIEGMYNAWFKSVVLQVAIWSHPYTKENDW

*P. ferrireducens* protoglobin-UniProt G7VHJ7
SEQ ID NO: 16
MREIPGYEFGKVPDAPISDEEFELLKKSVMWTEEDEKYRKLACEVLKGQV
EQILDLWYGWVGSNPHLVYYFGDRSGRPIPQYLEAVRKRFGQWILDTVCR
SYDRQWLNYVYEIGLRHHRTKKGKTDGVETVEHIPLRYMVAFIAPIGLTI
KPFLEKGGHPPDVVEKMWAAWIKSVVLQVAIWSHPYAKPGEW

*C. necator* nitric oxide dioxygenase-UniProt P39662
SEQ ID NO: 17:
MLTQKTKDIVKATAPVLAEHGYDIIKCFYQRMFEAHPELKNVFNMAHQEQ
GQQQQALARAVYAYAENIEDPNSLMAVLKNIANKHASLGVKPEQYPIVGE
HLLAAIKEVLGNAATDDIISAWAQAYGNLADVLMGMESELYERSAEQPGG
WKGWRTFVIREKRPESDVITSFILEPADGGPVVNFEPGQYTSVAIDVPAL
GLQQIRQYSLSDMPNGRSYRISVKREGGGPQPPGYVSNLLHDHVNVGDQV
KLAAPYGSFHIDVDAKTPIVLISGGVGLTPMVSMLKVALQAPPRQVVFVH
GARNSAVHAMRDRLREAAKTYENLDLFVFYDQPLPEDVQGRDYDYPGLVD
VKQIEKSILLPDADYYICGPIPFMRMQHDALKNLGIHEARIHYEVFGPDL

---

What is claimed is:

1. A reaction mixture for producing a C—H insertion product, the reaction mixture comprising a substrate having an sp³-hybridized C—H bond, a carbene precursor for modification of the carbon atom in the sp³-hybridized C—H bond, and a heme protein comprising an iron porphyrin, wherein the heme protein is selected from the group consisting of a truncated P450$_{BM3}$ comprising the amino acid sequence set forth in SEQ ID NO:1, or a variant thereof, a full-length P450$_{BM3}$ comprising the amino acid sequence set forth in SEQ ID NO:2, or a variant thereof, and a nitric oxide dioxygenase protein from *Rhodothermus marinus* or a variant thereof, and wherein the carbene precursor and the substrate having the sp$^{\alpha}$-hybridized C—H bond are separate compounds, or the carbene precursor is present in the same compound as the substrate having the sp$^{\alpha}$-hybridized C—H bond.

2. The reaction mixture of claim 1, wherein the substrate having the sp³-hybridized C—H bond is a compound according to Formula I:

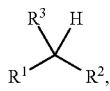

(I)

wherein:

$R^1$, $R^2$, and $R^3$ are independently selected from the group consisting of H, $C_{1-18}$ alkyl, $C_{2-18}$ alkenyl, $C_{2-18}$ alkynyl, 2- to 18-membered heteroalkyl, $C_{1-18}$ haloalkyl, $C_{1-18}$ alkoxy, $C_{3-10}$ cycloalkyl, $C_{6-10}$ aryl, 3- to 10-membered heterocyclyl, 5- to 10-membered heteroaryl, —SR$^8$, —C(O)R$^8$, —C(O)OR$^8$, —C(O)SR$^8$, —C(O)N(R$^8$)$_2$, —N(R$^9$)$_2$, —B(R$^{10}$)$_2$, —Si(R$^{10}$)$_3$, —P(R$^{10}$)$_3$, and —P(R$^{10}$)$_4$; or $R^1$ and $R^2$ are taken together to form $C_{3-10}$ cycloalkyl, $C_{6-10}$ aryl, 3- to 10-membered heterocyclyl, and 5- to 10-membered heteroaryl, each of which is optionally substituted;

each $R^8$, $R^9$, and $R^{10}$ is independently selected from the group consisting of H, $C_{1-18}$ alkyl, $C_{2-18}$ alkenyl, —OH, oxo, $C_{1-18}$ alkoxy, $C_{2-18}$ alkynyl, $C_{6-10}$ aryl, 5- to 10-membered heteroaryl, and 3- to 10-membered heterocyclyl; and each of $R^1$, $R^2$, $R^3$, $R^8$, $R^9$, and $R^{10}$ is optionally and independently substituted.

3. The reaction mixture of claim 2, wherein the substrate having the sp³-hybridized C—H bond is a compound according to Formula Ia:

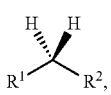
(Ia)

$R^1$ is selected from the group consisting of optionally substituted $C_{1-18}$ alkyl, 2- to 18-membered heteroalkyl, $C_{1-18}$ alkoxy, $C_{3-10}$ cycloalkyl, $C_{1-18}$ fluoroalkyl, substituted $C_{6-10}$ aryl, and substituted 5- to 10-membered heteroaryl; and $R^2$ is independently selected from the group consisting of H, $C_{1-18}$ alkyl, 2- to 18-membered heteroalkyl, $C_{1-18}$ alkoxy, $C_{3-10}$ cycloalkyl, $C_{1-18}$ fluoroalkyl, substituted $C_{6-10}$ aryl, and substituted 5- to 10-membered heteroaryl; or $R^1$ and $R^2$ are taken together to form $C_{3-10}$ cycloalkyl, $C_{6-10}$ aryl, 3- to 10-membered heterocyclyl, and 5- to 10-membered heteroaryl, each of which is optionally substituted.

4. The reaction mixture of claim 1, wherein the substrate having the sp³-hybridized C—H bond is selected from the group consisting of:

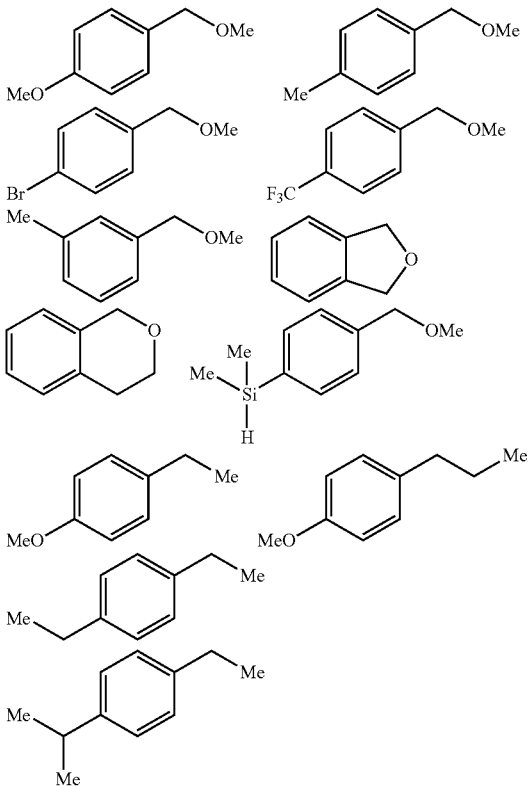

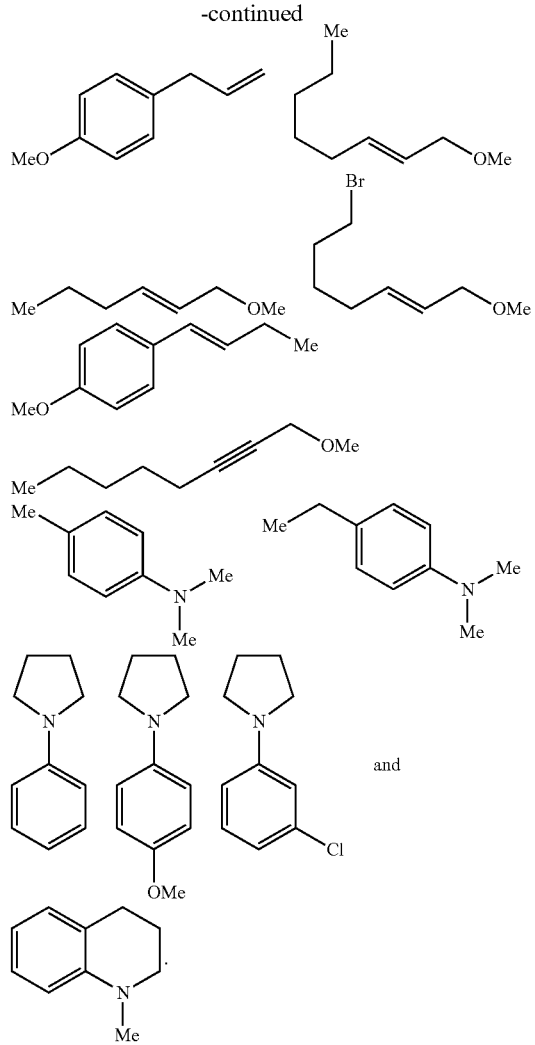

5. The reaction mixture of claim 1, wherein the carbene precursor reagent has a structure according to Formula II:

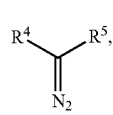
(II)

wherein:

$R^4$ is selected from the group consisting of H, —C(O)OR$^{4a}$, —C(O)R$^{4a}$, —C(O)N(R$^{4b}$)$_2$, —SO$_2$R$^{4a}$, —SO$_2$OR$^{4a}$, —P(O)(OR$^{4a}$)$_2$, —NO$_2$, —CN, $C_{1-18}$ alkyl, $C_{2-18}$ alkenyl, $C_{2-18}$ alkynyl, 2- to 18-membered heteroalkyl, $C_{1-18}$ haloalkyl, $C_{1-18}$ alkoxy, $C_{3-10}$ cycloalkyl, $C_{6-10}$ aryl, 3- to 10-membered heterocyclyl, and 5- to 10-membered heteroaryl;

each $R^{4a}$ is independently selected from the group consisting of H, $C_{1-18}$ alkyl, $C_{2-18}$ alkenyl, $C_{2-18}$ alkynyl, $C_{6-10}$ aryl, 3- to 10-membered heterocyclyl, and 5- to 10-membered heteroaryl;

each $R^{4b}$ is independently selected from the group consisting of H, $C_{1-18}$ alkyl, $C_{2-18}$ alkenyl, $C_{2-18}$ alkynyl, and $C_{1-18}$ alkoxy;

R[5] is an electron-withdrawing group selected from the group consisting of —C(O)OR[5a], —C(O)R[5a], —C(O)N(R[5b])$_2$, —SO$_2$R[5a], —SO$_2$OR[5a], —P(O)(OR[5a])$_2$, —NO$_2$, and —CN;

each R[5a] is independently selected from the group consisting of H, $C_{1-18}$ alkyl, $C_{2-18}$ alkenyl, $C_{2-18}$ alkynyl, $C_{6-10}$ aryl, 3- to 10-membered heterocyclyl, and 5- to 10-membered heteroaryl;

each R[5b] is independently selected from the group consisting of H, $C_{1-18}$ alkyl, $C_{2-18}$ alkenyl, $C_{2-18}$ alkynyl, and $C_{1-8}$ alkoxy; and R[4] and R[5] are optionally and independently substituted; or R[4] and R[5] are taken together to form $C_{3-10}$ cycloalkyl, $C_{6-10}$ aryl, 3- to 10-membered heterocyclyl, and 5- to 10-membered heteroaryl, each of which is optionally substituted.

6. The reaction mixture of claim 5, wherein:

R[4] is independently selected from the group consisting of H, —C(O)OR[4a], —C(O)R[4a], —SO$_2$R[4a], —SO$_2$OR[4a], substituted $C_{1-18}$ alkyl, 2- to 18-membered heteroalkyl, $C_{1-18}$ alkoxy, $C_{3-10}$ cycloalkyl, $C_{1-18}$ fluoroalkyl, substituted $C_{6-10}$ aryl, and substituted 5- to 10-membered heteroaryl;

R[4a] is $C_{1-8}$ alkyl;

R[5] is selected from the group consisting of —C(O)OR[5a], —C(O)R[5a], —SO$_2$R[5a], and —SO$_2$OR[5a]; and R[5a] is $C_{1-8}$ alkyl; or R[4] and R[5] are optionally taken together to form $C_{3-10}$ cycloalkyl, $C_{6-10}$ aryl, 3- to 10-membered heterocyclyl, and 5- to 10-membered heteroaryl, each of which is optionally substituted.

7. The reaction mixture of claim 1, wherein the carbene precursor is selected from the group consisting of:

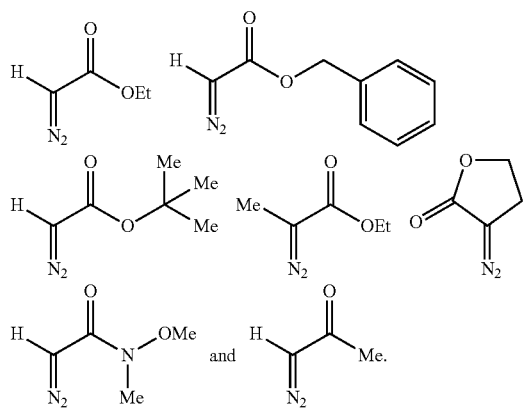

8. The reaction mixture of claim 1, wherein the substrate having the sp$^a$-hybridized C—H bond is a compound according to Formula III:

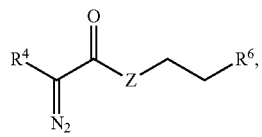

(III)

wherein:

Z is selected from the group consisting of C(R[7])$_2$, O, and NR[7];

R[4] is selected from the group consisting of H, —C(O)OR[4a], —C(O)R[4a], —C(O)N(R[4b])$_2$, —SO$_2$R[4a], —SO$_2$OR[4a], —P(O)(OR[4a])$_2$, —NO$_2$, —CN, $C_{1-18}$ alkyl, $C_{2-18}$ alkenyl, $C_{2-18}$ alkynyl, 2- to 18-membered heteroalkyl, $C_{1-18}$ haloalkyl, $C_{1-18}$ alkoxy, $C_{3-10}$ cycloalkyl, $C_{6-10}$ aryl, 3- to 10-membered heterocyclyl, and 5- to 10-membered heteroaryl, each of which is optionally substituted;

R[6] is selected from the group consisting of H, $C_{1-18}$ alkyl, $C_{2-18}$ alkenyl, $C_{2-18}$ alkynyl, 2 to 18-membered heteroalkyl, $C_{1-18}$ haloalkyl, $C_{1-18}$ alkoxy, $C_{3-10}$ cycloalkyl, $C_{6-10}$ aryl, 3- to 10-membered heterocyclyl, and 5- to 10-membered heteroaryl, each of which is optionally substituted; and each R[7] is independently selected from the group consisting of H and $C_{1-8}$ alkyl.

9. The reaction mixture of claim 1, wherein the reaction mixture further comprises a reducing agent.

10. The reaction mixture of claim 1, wherein the heme protein is selected from the group consisting of a truncated P450$_{BM3}$ comprising the amino acid sequence set forth in SEQ ID NO:1, or a variant thereof, and a full-length P450$_{BM3}$ comprising the amino acid sequence set forth in SEQ ID NO:2, or a variant thereof.

11. The reaction mixture of claim 1, wherein the heme protein contains one or more mutations at positions corresponding to residues N70, A74, V78, A82, F87, M118, P142, F162, T175, M177, A184, S226, H236, E252, I263, H266, T268, A290, T327, A328, A330, L353, I366, C400, I401, T436, L437, T438, E442 as determined with reference to SEQ ID NO:1.

12. The reaction mixture of claim 1, wherein the heme protein is a nitric oxide dioxygenase protein from *Rhodothermus marinus* or a variant thereof.

13. The reaction mixture of claim 12, wherein the nitric oxide dioxygenase protein from *Rhodothermus marinus* contains a mutation at the position Y32 as determined with reference to SEQ ID NO:4.

14. A method for producing a C—H insertion product, the method comprising:

(a) providing a substrate having an sp$^3$-hybridized C—H bond, a carbene precursor for modification of the carbon atom in the sp$^3$-hybridized C—H bond, and a heme protein comprising an iron porphyrin, wherein the heme protein is selected from the group consisting of a truncated P450$_{BM3}$ comprising the amino acid sequence set forth in SEQ ID NO:1, or a variant thereof, a full-length P450$_{BM3}$ comprising the amino acid sequence set forth in SEQ ID NO:2, or a variant thereof, and a nitric oxide dioxygenase protein from *Rhodothermus marinus* or a variant thereof; and (b) admixing the components of step (a) under conditions sufficient to produce the C—H insertion product.

15. The method of claim 14, wherein the heme protein is selected from the group consisting of a truncated P450$_{BM3}$ comprising the amino acid sequence set forth in SEQ ID NO:1, or a variant thereof, and a full-length P450$_{BM3}$ having the amino acid sequence set forth in SEQ ID NO:2, or a variant thereof.

16. The method of claim 14, wherein the heme protein comprises one or more mutations at positions corresponding to residues N70, A74, V78, A82, F87, M118, P142, F162, T175, M177, A184, S226, H236, E252, I263, H266, T268, A290, T327, A328, A330, L353, I366, C400, I401, T436, L437, T438, E442 as determined with reference to SEQ ID NO:1.

* * * * *